United States Patent [19]

Bridges et al.

[11] Patent Number: 5,340,833
[45] Date of Patent: Aug. 23, 1994

[54] UROKINASE INHIBITORS

[75] Inventors: Alexander Bridges; Bruce A. Littlefield, both of Andover; C. Eric Schwartz, Wakefield, all of Mass.

[73] Assignee: Eisai Co., Ltd., Tokyo, Japan

[21] Appl. No.: 877,664

[22] Filed: May 1, 1992

[51] Int. Cl.$^5$ .................. A61K 31/38; C07D 333/66
[52] U.S. Cl. .................. 514/443; 514/233.5; 514/307; 514/337; 544/146; 546/144; 546/274; 549/51; 549/57; 549/58
[58] Field of Search .................. 549/51, 57, 58; 514/445, 233.5, 307, 337; 544/146; 546/144, 274

[56] References Cited

U.S. PATENT DOCUMENTS

| | | | |
|---|---|---|---|
| 3,855,242 | 12/1974 | Chapman et al. | 549/58 |
| 3,971,814 | 7/1976 | Stoss et al. | 549/55 |
| 4,025,504 | 5/1977 | Hamanaka et al. | 260/239.1 |
| 4,025,506 | 4/1977 | Hamanaka et al. | 260/239.1 |
| 4,929,636 | 5/1990 | Redpath et al. | 514/433 |
| 5,026,724 | 6/1991 | Logan et al. | 514/443 |
| 5,118,680 | 6/1992 | Muller et al. | 549/55 |

FOREIGN PATENT DOCUMENTS

| | | |
|---|---|---|
| 0158380 | 10/1985 | European Pat. Off. . |
| 0352832 | 1/1990 | European Pat. Off. . |
| 0403885 | 12/1990 | European Pat. Off. . |
| 2258036 | 5/1974 | Fed. Rep. of Germany . |

OTHER PUBLICATIONS

Yang et al., J. Med. Chem. 33:2956–2961, 1990.
Avery et al., Arch. Ophthalmol. 108:1474–1476, 1990.
Kleyman et al., J. Membrane Biol. 105:1–21, 1988.
Kellen et al., Anticancer Research 8:1373–1376, 1988.
Vassalli et al., FEBS Lett. 214:187–191, 1987.
Geratz et al., Archives of Biochemistry and Biophysics 197:551–559, 1979.
Geratz et al., Thrombosis Research 24:73–83, 1981.
Tidwell et al., Journal of Medicinal Chemistry 21:613–623, 1978.
Sturzebecher et al., Pharmazie 33:599–602, 1978.
Tidwell et al., Biochimica et Biophysica Acta 445:729–738, 1976.
Geratz et al., Journal of Medicinal Chemistry 19:634–639, 1976.
Shepard et al., Journal of Heterocyclic Chemistry 13:1219–1224, 1976.
Geratz et al., Journal of Medicinal Chemistry, 18:477–481, 1975.
Geratz et al, Thrombos. Diathes, Haemorrh. (Stuttg.) 33:230–243, 1975.
Dann et al., Liebigs Ann. Chem. 760:37–87, 1972.

*Primary Examiner*—Richard L. Raymond
*Attorney, Agent, or Firm*—Fish & Richardson

[57] ABSTRACT

Disclosed are benzothiophene and thienothiophene derivatives useful for inhibiting urokinase activity.

15 Claims, 4 Drawing Sheets

UROKINASE INHIBITORS

BACKGROUND OF THE INVENTION

This invention relates to urokinase inhibitors.

Urokinase (urinary-type plasminogen activator or uPA; International Union of Biochemistry classification number: EC 3.4.21.31) is a proteolytic enzyme which is highly specific for a single peptide bond in plasminogen. Cleavage of this bond by urokinase ("plasminogen activation") results in formation of the potent general protease plasmin. Many cell types use urokinase as a key initiator of plasmin-mediated proteolytic degradation or modification of extracellular support structures such as extracellular matrix (ECM) and basement membrane (BM). Cells exist, move, and interact with each other in tissues and organs within the physical framework provided by ECM and BM. Movement of cells within ECM or across BM requires local proteolytic degradation or modification of these structures, allowing cells to "invade" into adjacent areas which were previously unavailable to the cells.

Cellular invasiveness intiated by urokinase is central to a wide variety of normal and disease-state physiological processes (reviewed in: Blasi, F., Vassalli, J. D., and Danø, K. *J. Cell Biol.* 104:801–804, 1987; Danø, K., Anderson, P.A., Grøndahl-Hansen, J., Kristensen, P., Nielsen, L.S., and Skriver, L. *Adv. Cancer Res.* 44:139–266.1985; Littlefield, B. A. *Ann. N. Y. Acad. Sci.* 622:167–175, 1991; Saksela, O. *Biochim. Biophys. Acta* 823:35–65, 1985; Testa, J. E. and Quigley, J. P. *Cancer Metast. Rev.* 9:353–367, 1990). Such processes include, but are not limited to, angiogenesis (neovascularization), bone restructuring, embryo implantation in the uterus, infiltration of immune cells into inflammatory sites, ovulation, spermatogenesis, tissue remodelling during wound repair and organ differentiation, fibrosis, local invasion of tumors into adjacent areas, metastatic spread of tumor cells from primary to secondary sites, and tissue destruction in arthritis. Inhibitors of urokinase therefore have mechanism-based anti-angiogenic, anti-arthritic, anti-inflammatory, anti-invasive, anti-metastatic, anti-osteoporotic, anti-retinopathic (for angiogenesis-dependent retinopathies), contraceptive, and tumoristatic activities.

Beneficial effects of urokinase inhibitors have been reported using anti-urokinase monoclonal antibodies and certain other known urokinase inhibitors. For instance, anti-urokinase monoclonal antibodies have been reported to block tumor cell invasiveness in vitro (Hollas, W., Blasi, F. and Boyd, D. *Cancer Res.* 51:3690–3695, 1991; Meissauer, A., Kramer, M. D., Hofmann, M., Erkell, L. J., Jacob, E., Schirrmacher, V. and Brunner, G. *Exp. Cell Res.* 192:453–459, 1991), tumor metastasis and invasion in vivo (Ossowski, L. *J. Cell Biol.* 107:2437–2445, 1988; Ossowski, L., Russo-Payne, H. and Wilson, E. L. *Cancer Res.* 51:274–81, 1991), and angiogenesis in vivo (Jerdan, J. A., Gilliam, K., Ransey, C. and Glaser, B. *J. Cell Biol.* 115[3 Pt 2]:402a, 1991). In addition, amiloride, a known urokinase inhibitor of only moderate potency, has been reported to inhibit tumor metastasis in vivo (Kellen, J. A., Mirakian, A. and Kolin, A. *Anticancer Res.* 8:1373–1376, 1988) and angiogenesis/capillary network formation in vitro (Alliegro, M. A., Alliegro, M. C. and Glaser, B. M. *J. Cell Biol.* 115[3 Pt 2]:402a, 1991).

Central to the ability of urokinase to mediate cellular invasiveness is the existence of specific high affinity urokinase receptors which concentrate urokinase on the cell surface, leading to the generation of locally high plasmin concentrations between cells and ECM or BM (Blasi, F., Vassalli, J.-D., and Danø, K. *J. Cell Biol.* 104:801–804, 1987; Roldan, A. L., Cubellis, M. V., Masucci, M. T., Behrendt, N., Lund, L. R., Danø, K, Appella, E., and Blasi, F. *EMBO J.* 9:467–74, 1990). High plasmin concentrations between invasive cells and ECM or BM are necessary in order to overcome inhibitory effects of ubiquitous plasmin inhibitors, such as $\alpha_2$-antiplasmin and $\alpha_2$-macroglobulin. Thus, it is cell surface receptor-bound urokinase, and not simply free urokinase secreted by cells, which plays the predominant role in initiating cellular invasiveness.

SUMMARY OF THE INVENTION

In general, the invention features a compound of the formula:

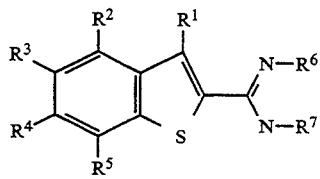

wherein $R^1$ is H, $NH_2$, or a halogen;

each $R^2$–$R^5$, independently, is a H, OH, halogen, amino, nitro or organic group, provided that at least one $R^2$–$R^5$ is an organic group which includes 5 carbons or greater, an organic group which contains a sulfur atom or hydroxy, an unsaturated organic group, or a cyclic organic group; and each $R^6$ and $R^7$, independently, is H or a straight chain alkyl group of between 1 and 6 carbons.

The invention also features a compound of the formula:

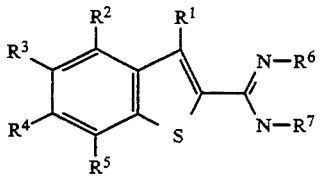

wherein $R^1$ is H, $NH_2$, or a halogen;

each $R^2$–$R^5$, independently, is a H, OH, halogen, amino, nitro, or organic group, provided that at least one of $R^2$–$R^5$ is a group other than H, OH, $NO_2$, CN, a halogen, an alkyl group of between 1 and 4 carbons, an alkoxy group of between 1 and 4 carbons, a haloalkyl group of between 1 and 4 carbons, a haloalkoxy group of between 1 and 4 carbons, an amino group, an amino group substituted with an alkyl group of between 1 and 4 carbons, a nitrile group, or a carboxamidine group, and further provided that no two adjacent $R^2$–$R^5$ groups together form a methylenedioxy group; and each $R^6$ and $R^7$, independently, is H or a straight chain alkyl group of between 1 and 6 carbons.

The invention also features a compound of formula:

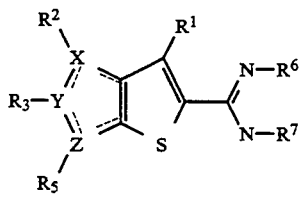

wherein at least one of X, Y, or Z must be C; at least one of X, Y, or Z must be O, N, or S; and, if more than one of X, Y, or Z is O, N, or S, then at least one of those groups is N;

$R^1$ is H, $NH_2$, or a halogen;

each $R^2$, $R^3$, or $R^5$, independently, is H, a halogen, or an organic group; and each $R^6$ and $R^7$, independently, is H or a straight chain alkyl group of between 1 and 6 carbons.

Through their investigation of the benzothiophene and thienothiophene compounds described herein, applicants have determined that maximum urokinase inhibitory activity and/or selectivity is conferred by the following:

(a) an $R^1$ group which is NH or, most preferably, H;

(b) an $R^2$ group which is of a large size, for example, an $R^2$ group which includes less than or equal to 40 carbon atoms, with larger groups than 4 carbon atoms being preferred (i.e., potency initially increases with increasing sidechain size);

(c) an $R^2$ group which is planar;

(d) an $R^2$ group which is saturated or, if unsaturated, which contains a double or triple bond at the 1 position (and which may contain double or triple bonds elsewhere in the sidechain); an alkene with an E double bond at the 1 position is preferred among unsaturated $R^2$ groups; such unsaturated sidechains preferably include an aromatic ring;

(e) an $R^2$ group which does not include a heteroatom directly bonded to the ring, unless that heteroatom is a halogen or sulfur;

(f) an $R^2$ group which is an aromatic ring (preferably, a furan ring) optionally substituted;

(g) an $R^3$ group which is substituted; potency generally increases with the size of the $R^3$ sidechain, but to a lesser degree than is observed with $R^2$ groups; $R^3$ preferably includes less than or equal to 20 carbon atoms;

(h) an $R^4$ and an $R^5$ group which is H or, less preferably, an alkyl group of less than or equal to 20 carbon atoms; substituents at this site are generally detrimental; and (i) an $R^6$ and an $R^7$ group which is H; substituents at these sites generally decrease activity; a methyl or an ethyl would be expected to have a small negative effect on activity; and a larger alkyl, an OH, or an $NH_2$, or an aromatic group would be expected to have a larger negative effect on activity.

In other preferred embodiments, the benzothiophene and thienothiophene backbones shown above are preferably substituted as follows:

$R^1$ is H, $NH_2$, or a halogen;

each $R^2$, $R^3$, $R^4$, or $R^5$, independently, is:

a straight chain alkyl group of between 5 and 10 carbons;

a straight chain alkenyl group of between 1 and 10 carbons with an E or Z double bond (preferably at the 1 position);

a straight chain alkynyl group of between 1 and 10 carbons (preferably with a triple bond at the 1 position);

a straight chain alkyl group of between 1 and 10 carbons substituted with at least one $R^8$ group, except halogen when the chain is 4 carbons or less;

a straight chain alkoxy group of between 1 and 10 carbons substituted with at least one $R^8$ group, except halogen when the chain is 4 carbons or less;

a straight chain alkenyl group of between 2 and 10 carbons with an E or Z double bond (preferably at the 1 position) substituted with at least one $R^8$ group;

a straight chain alkynyl group of between 2 and 10 carbons (preferably with a triple bond at the 1 position) substituted with at least one $R^8$ group;

a cycloalkyl group of between 3 and 10 carbons;

a cycloalkenyl group of between 3 and 10 carbons;

a bicycloalkyl group of between 6 and 12 carbons;

a bicycloalkenyl group of between 7 and 12 carbons;

a cycloalkyl-alkyl group of between 4 and 20 carbons;

a cycloalkyl-alkenyl group of between 5 and 20 carbons;

a cycloalkyl-alkynyl group of between 5 and 20 carbons;

a cycloalkenyl-alkyl group of between 4 and 20 carbons;

a cycloalkenyl-alkenyl group of between 5 and 20 carbons;

a cycloalkenyl-alkynyl group of between 5 and 20 carbons;

a thioalkyl group of between 1 and 10 carbons;

a sulfinylalkyl group of between 1 and 10 carbons;

a sulfonylalkyl group of between 1 and 10 carbons;

a thioalkyl group of between 1 and 10 carbons substituted with at least one $R^8$ group;

a sulfinylalkyl group of between 1 and 10 carbons substituted with at least one $R^8$ group;

a sulfonylalkyl group of between 1 and 10 carbons substituted with at least one $R^8$ group;

a thioalkenyl group of between 1 and 10 carbons;

a sulfinylalkenyl group of between 1 and 10 carbons;

a sulfonylalkenyl group of between 1 and 10 carbons;

a thioalkenyl group of between 1 and 10 carbons substituted with at least one $R^8$ group;

a sulfinylalkenyl group of between 1 and 10 carbons substituted with at least one $R^8$ group;

a sulfonylalkenyl group of between 1 and 10 carbons substituted with at least one $R^8$ group;

a thiocycloalkyl group of between 3 and 6 carbons;

a sulfinylcycloalkyl group of between 3 and 6 carbons;

a sulfonylcycloalkyl group of between 3 and 6 carbons;

a thiocycloalkenyl group of between 3 and 6 carbons;

a sulfinylcycloalkenyl group of between 3 and 6 carbons;

a sulfonylcycloalkenyl group of between 3 and 6 carbons;

a phenyl group;

a phenyl group substituted with at least one $R^9$ group;

a 2- or 3-furanyl group; a 2- or 3-thienyl group; a 2- or 3- or 4-pyridyl group; a pyrimidyl group; an oxazolo group; an isoxazolo group; a thiazolo group; an isothiazolo group; a pyrazolo group; an imidazolo group; a pyrazino group; a pyridazino group;

a bicyclic aromatic group chosen from a naphthyl group, a benzothienyl group, an indolyl group, a benzofuranyl group, a naphthyridinyl group, a quinoxalinyl group, a quinazolinyl group, a quinolinyl group, an isoquinolinyl group, a benzimidazoyl group, a benzoxazoyl group, or a benzothiozoyl group, or any of said bicyclic aromatic groups substituted with at least one $R^9$ group;

a biaryl group consisting of any two aromatic groups, the same or different, described above linked directly together or at least one one of the aromatic groups substituted with at least one $R^9$ group;

a tetrahydrofuranyl group;

a cycloalkoxy group of between 3 and 8 carbons a cycloalkenoxy group of between 3 and 8 carbons an oxyaryl group; an oxyaryl group substituted with at least one $R^9$ group;

an oxyheteroaryl group; an oxyheteroaryl group substituted with at least one $R^9$ group;

a thioaryl group; a sulfinylaryl group; a sulfonylaryl group;

a thioheteroaryl group; a sulfinylheteroaryl group; a sulfonylheteroaryl group;

a thioaryl group substituted with at least one $R^9$ group;

a sulfinylaryl group substituted with at least one $R^9$ group;

a sulfonylaryl group substituted with at least one $R^9$ group;

a thioheteroaryl group substituted with at least one $R^9$ group;

a sulfinylheteroaryl group substituted with at least one $R^9$ group;

a sulfonylheteroaryl group substituted with at least one $R^9$ group;

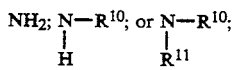

or $R^2$ and $R^3$, taken together, form an aryl ring chosen from a phenyl group, a 2- or 3-furanyl group, a 2- or 3-thienyl group, a 2- or 3- or 4-pyridyl group, a pyrimidyl group, an oxazolo group, an isoxazolo group, a thiazolo group, an isothiazolo group, a pyrazolo group, an imidazolo group, a pyrazino group, or a pyridazino group, or any of said aryl ring groups substituted with at least one $R^9$ group or with at least one $R^{12}$ group; or $R^4$, taken with $R^3$ or $R^5$, forms an aryl ring chosen from a phenyl group, a 2- or 3-furanyl group, a 2- or 3-thienyl group, a 2- or 3- or 4-pyridyl group, a pyrimidyl group, an oxazolo group, an isoxazolo group, a thiazolo group, an isothiazolo group, a pyrazolo group, an imidazolo group, a pyrazino group, or a pyridazino group, or any of said aryl ring groups substituted with at least one $R^9$ group or with at least one $R^{12}$ group; and each $R^6$ and $R^7$, independently, is H or an alkyl chain of between 1 and 6 carbons;

wherein each $R^8$, independently, is:

a straight chain alkyl group of between 1 and 6 carbons;

a cycloalkyl ring of between 3 and 6 carbons;

an alkoxy group of between 1 and 6 carbons;

an alkylthio group of between 1 and 6 carbons; an alkylthio group of between 1 and 6 carbons with the S oxidized;

a hydroxy group; a halogen group;

a phenyl group; a phenyl group substituted with at least one $R^9$ group;

a 2- or 3-furanyl group; a 2- or 3-thienyl group; a 2- or 3- or 4-pyridyl group; a pyrimidyl group; an oxazolo group; an isoxazolo group; a thiazolo group; an isothiazolo group; a pyrazolo group; an imidazolo group; a pyrazino group; a pyridazino group;

a bicyclic aromatic group chosen from a naphthyl group, a benzothienyl group, an indolyl group, a benzofuranyl group, a naphthyridinyl group, a quinoxalinyl group, a quinazolinyl group, a quinolinyl group, an isoquinolinyl group, a benzimidazoyl group, a benzoxazoyl group, or a benzothiazoyl group, or any of said bicyclic aromatic groups substituted with at least one $R^9$ group;

tetrahydrofuranyl; or tetrahydrothiofuranyl; and wherein each $R^9$, independently, is:

a straight chain alkyl group of between 1 and 6 carbons; an alkoxy group of between 1 and 6 carbons; an acyloxy group of between 1 and 6 carbons; a methylenedioxy group; an ethylenedioxy group; a hydroxymethyl group; an alkoxymethyl group of between 1 and 6 carbons; a halo group; a hydroxy group; a nitro group; a cyano group; an acyl group of between 1 and 6 carbons; an alkylthio group of between 1 and 6 carbons; an alkylthio group of between 1 and 6 carbons with an oxidized S; a carboxylic acid group; a carboxylate ester group; or a carboxamidino group, a carboxamido group, or an amino group, wherein the nitrogen group is $NH_2$,

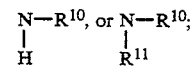

and wherein each $R^{10}$ and $R^{11}$ is:

a straight chain alkyl group of between 1 and 6 carbons; a cycloalkyl group of between 3 and 6 carbons; a phenyl group; or a phenyl group substituted with at least one $R^9$ group; or wherein $R^{10}$ and $R^{11}$, taken together, form a pyrrolidinyl, a piperidinyl, a morpholino, or an N-substituted piperazino ring; and wherein each $R^{12}$, independently, is:

an alkenoxymethyl group of between 1 and 6 carbons;

an alkynoxymethyl group of between 1 and 6 carbons;

an arylalkenyl group;

an arylalkenyl group, wherein said aryl is phenyl, 2- or 3-furanyl, 2- or 3-thienyl, 2- or 3- or 4-pyridyl, pyrimidyl, oxazolo, isoxazolo, thiazolo, isothiazolo, pyrazolo, imidazolo, pyrazino, or pyradazino, or any of said aryl groups substituted with at least one $R^9$ group;

an arylalkynyl group; or an arylalkynyl group, wherein said aryl is phenyl, 2- or 3-furanyl, 2- or 3-thienyl, 2- or 3- or 4-pyridyl, pyrimidyl, oxazolo, isoxazolo, thiazolo, isothiazolo, pyrazolo, imidazolo, pyrazino, or pyradazino, or any of said aryl groups substituted with at least on $R^9$ group.

If at least one of $R^2$–$R^5$ fits the above definitions, then the others may be independently, H, halogen, an alkyl or haloalkyl of between 1 and 4 carbons, an alkoxy or haloalkoxy of between 1 and 4 carbons, a cyano group or a carboxamidino group.

More preferably, the benzothiophene and thienothiophene backbones shown above are substituted as follows:

(i) $R^1$ and $R^4$–$R^7$ are H; and one of $R^2$ or $R^3$ is H or halogen, the other is an organic group of 5 or more carbons, an organic group which includes a sulfur atom, unsaturation, or $R^8$ substitution, an aryl group, or a heteroaryl group as described above; or (ii) $R^1$ is H;

$R^2$ and $R^3$, taken together, form:

an aryl ring chosen from a phenyl group, a 2- or 3-furanyl group, a 2- or 3-thienyl group, a 2- or 3- or 4-pyridyl group, a pyrimidyl group, an oxazolo group, an isoxazolo group, a thiazolo group, an isothiazolo group, a pyrazolo group, an imidazolo group, a pyrazino group, or a pyridazino group, or any of said aryl ring groups substituted with at least one $R^9$ group or with at least one $R^{12}$ group; and each $R^4, R^5, R^6$, and $R^7$ is H;

wherein each $R^9$, independently, is:

a straight chain alkyl group of between 1 and 6 carbons; an alkoxy group of between 1 and 6 carbons; an acyloxy group of between 1 and 6 carbons; a methylenedioxy group; an ethylenedioxy group; a hydroxymethyl group; an alkoxymethyl group of between 1 and 6 carbons; a halo group; a hydroxy group; a nitro group; a cyano group; an acyl group of between 1 and 6 carbons; an alkylthio group of between 1 and 6 carbons; an alkylthio group of between 1 and 6 carbons with an oxidized S; a carboxylic acid group; a carboxylate ester group; or a carboxamidino group, a carboxamido group, or an amino group, wherein the nitrogen group is $NH_2$,

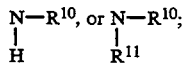

and wherein each $R^{10}$ and $R^{11}$ is:

a straight chain alkyl group of between 1 and 6 carbons; a cycloalkyl group of between 3 and 6 carbons; a phenyl group; or a phenyl group substituted with at least one $R^9$ group; or wherein $R^{10}$ and $R^{11}$, taken together, form a pyrrolidinyl, a piperidinyl, a morpholino or an N-substituted piperazino ring; and wherein each $R^{12}$, independently, is:

an alkenoxymethyl group of between 1 and 6 carbons;

an alkynoxymethyl group of between 1 and 6 carbons;

an arylalkenyl group;

an arylalkenyl group, wherein said aryl is phenyl, 2- or 3-furanyl, 2- or 3-thienyl, 2- or 3- or 4-pyridyl, pyrimidyl, oxazolo, isoxazolo, thiazolo, isothiazolo, pyrazolo, imidazolo, pyrazino, or pyradazino, or any of said aryl groups substituted with at least one $R^9$ group;

an arylalkynyl group; or an arylalkynyl group, wherein said aryl is phenyl, 2- or 3-furanyl, 2- or 3-thienyl, 2- or 3- or 4-pyridyl, pyrimidyl, oxazolo, isoxazolo, thiazolo, isothiazolo, pyrazolo, imidazolo, pyrazino, or pyradazino, or any of said aryl groups substituted with at least one $R^9$ group; or (iii) $R^1$ is H;

$R^2$ is an appropriate organic group, organic group including a sulfur atom, aryl group, or heteroaryl group as described above:

$R^3$ and $R^4$, taken together, form:

an aryl ring chosen from a phenyl group, a 2- or 3-furanyl group, a 2- or 3-thienyl group, a 2- or 3- or 4-pyridyl group, a pyrimidyl group, an oxazolo group, an isoxazolo group, a thiazolo group, an isothiazolo group, a pyrazolo group, an imidazolo group, a pyrazino group, or a pyridazino group, or any of said aryl ring groups substituted with at least one $R^9$ group or with at least one $R^{12}$ group; and each $R^5, R^6$, and $R^7$ is H;

wherein each $R^9$, independently, is:

a straight chain alkyl group of between 1 and 6 carbons; an alkoxy group of between 1 and 6 carbons; an acyloxy group of between 1 and 6 carbons; a methylenedioxy group; an ethylenedioxy group; a hydroxymethyl group; an alkoxymethyl group of between 1 and 6 carbons; a halo group; a hydroxy group; a nitro group; a cyano group; an acyl group of between 1 and 6 carbons; an alkylthio group of between 1 and 6 carbons; an alkylthio group of between 1 and 6 carbons with an oxidized S; a carboxylic acid group; a carboxylate ester group; or a carboxamidino group, a carboxamido group, or an amino group, wherein the nitrogen group is $NH_2$,

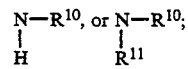

and wherein each $R^{10}$ and $R^{11}$ is:

a straight chain alkyl group of between 1 and 6 carbons; a cycloalkyl group of between 3 and 6 carbons; a phenyl group; or a phenyl group substituted with at least one $R^9$ group; or wherein $R^{10}$ and $R^{11}$, taken together, form a pyrrolidinyl, a piperidinyl, a morpholino, or an N-substituted piperazino ring; and wherein each $R^{12}$, independently, is:

an alkenoxymethyl group of between 1 and 6 carbons;

an alkynoxymethyl group of between 1 and 6 carbons;

an arylalkenyl group;

an arylalkenyl group, wherein said aryl is phenyl, 2- or 3-furanyl, 2- or 3-thienyl, 2- or 3- or 4-pyridyl, pyrimidyl, oxazolo, isoxazolo, thiazolo, isothiazolo, pyrazolo, imidazolo, pyrazino, or pyradazino, or any of said aryl groups substituted with at least one $R^9$ group;

an arylalkynyl group; or an arylakynyl group, wherein said aryl is phenyl, 2- or 3-furanyl, 2- or 3-thienyl, 2- or 3- or 4-pyridyl, pyrimidyl, oxazolo, isoxazolo, thiazolo, isothiazolo, pyrazolo, imidazolo, pyrazino, or pyradazino, or any of said aryl groups substituted with at least one $R^9$ group.

Most preferably, the benzothiophene and thienothiophene backbones shown above are substituted as follows:

(i) $R^1, R^3, R^4, R^5, R^6$ and $R^7$ are each H groups; and $R^2$ is:

a straight chain alkyl group of between 5 and 8 carbons; a 3-methylbutyl group; a 2-phenylethyl group; a 2-cyclopropylethyl group; an allyl group; a straight chain alkenyl group of between 3 and 6 carbons with an E or Z double bond at the 1 position; a 3-methyl-1-butenyl group; a 3-methyl-2-butenyl group; an E,4-methylpent-1-enyl group; an E,4-methylhex-1-enyl group; an E,4-ethylhex-1-enyl group; an E,5-hydroxypent-1-enyl group; an E,2-phenylethenyl group; an E,2-furan-2-ylethenyl group; an E,3-pyridyl-2-ylethenyl group; an E,2-benzothien-5-ylethenyl group; an E,2-(2-carboxamidinobenzothien-4-yl)ethenyl group; an E,2-(3,4-methylenedioxyphenyl)ethenyl group; an E,2-(3,4-dimethoxyphenyl)ethenyl group; an E,2-(3,4-ethylenedioxyphenyl)ethenyl group; an E/Z,2-cyclopropylethenyl group; an E,2-cyclohexylethenyl group; an E,3-phenylprop-1-enyl group; an E,5-phenylpent-1-enyl group; an ethynyl group; a 3-methylbut-1-ynyl group; a 3,3-dimethylbut-1-ynyl group; a 3-hydroxy-3,3-dimethylbut-1-ynyl group; a (3,4-methylenedioxy)phenylethynyl group; a furan-2-ylethynyl group; a cyclohexylethynyl group; a phenyl group; a 2-furanyl group; a 2-benzofuranyl group; a 2-thienyl group; a 3-pyridyl group; a hydroxymethyl group; a methylthio group; a 2-tetrahydrofuranyl group; a 5-(4-carboxamidinophenyl)furan-2-yl group; a 5-phenylfuran-2-yl group; a 5-(6-carboxamidinonaphth-2-yl)furan-2-yl group; or a [5-(4-carboxamidinophenyl)furan-2-yl]ethynyl group; or (ii) $R^1$, $R^2$, $R^4$, $R^5$, $R^6$ and $R^7$ are $R^3$ is:

a phenyl group; a 2-furanyl group; a 2-benzothienyl group; a straight chain alkenyl of between 2 and 6 carbons with an E or Z double bond at the 1 position; a 2-methyl-1-butenyl group; an E/Z,2-cyclopropylethenyl group; or an E,2-(4-carboxamidinophenyl)ethenyl group; or (iii) $R^1$, $R^4$, $R^5$, $R^6$ and $R^7$ are each H groups; $R^2$ is an $SCH_3$ group; and $R^3$ is a vinyl group; or (iv) $R^1$, $R^4$, $R^5$, $R^6$ and $R^7$ are each H groups; and $R^2$ and $R^3$, taken together, form a $(CH)_4$ ring; or (v) $R^1$, $R^2$, $R^5$, $R^6$ and $R^7$ are each H groups; and $R^3$ and $R^4$, taken together, form a $(CH)_4$ ring; or (vi) $R^1$, $R^4$, $R^5$, $R^6$ and $R^7$ are each H groups; and $R^2$ and $R^3$, taken together, form an $SC(CH_2OR^{13})CH$ ring, wherein $R^{13}$ is H, $CH_3$, or an allyl group; or (vii) $R^1$, $R^4$, $R^5$, $R^6$ and $R^7$ are each H groups; and $R^2$ and $R^3$, taken together, form an $SC(CH=CH-[4-carboxamidinophenyl]CH)$ group.

Any of the compounds of the invention is preferably formulated as a hydrochloride salt, although the free bases and salts of other pharmaceutically acceptable acids are also useful; preferably the therapeutic compounds of the invention inhibit urokinase activity.

In a related aspect, the invention features a therapeutic composition essentially comprising a compound of the invention formulated in a physiologically-acceptable carrier.

In a final aspect, the invention features methods for treating urokinase-mediated cellular invasion in a mammal. The methods involve administering to the mammal a urokinase-inhibiting amount of a compound of formula:

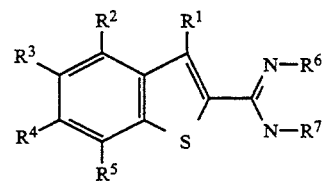

wherein $R^1$ is H, OH, $NH_2$, or a halogen;

each $R^2$-$R^5$, independently, is a H, halogen, or organic group; and each $R^6$ and $R^7$, independently, is H or a straight chain alkyl group of between 1 and 6 carbons;

or of formula:

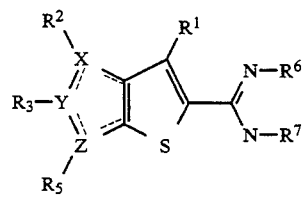

wherein at least one of X, Y, or Z must be C; at least one of X, Y, or Z must be O, N, or S; and, if more than one of X, Y, or Z is O, N, or S, then at least one of those groups is N;

$R^1$ is H, OH, $NH_2$, or a halogen;

each $R^2$, $R^3$, or $R^5$, independently, is a H, halogen, or organic group; and each $R^6$ and $R^7$, independently, is H or a straight chain alkyl group of between 1 and 6 carbons.

The compounds described herein inhibit urokinase enzymatic activity in a reversible competitive manner, with high selectivity for urokinase relative to certain other important proteases, including the fibrinolytic enzymes tissue-type plasminogen activator (tPA) and plasmin. In particular, as measured in a plasminogen-linked assay, most of the claimed compounds have $IC_{50}$ values against urokinase of 40 nM to 5 μM. In addition, they are generally 60–800-fold more active at inhibiting urokinase than tPA and are generally 400–10,000-fold selective for urokinase over plasmin. Of 144 benzothiophene derivatives tested to date, 141 exhibit potent and selective urokinase activity and of the 3 available thienothiophene compounds, all exhibit such activity. Accordingly, these compounds provide potent therapeutics for the treatment or prevention of urokinase-mediated disorders. Moreover, because the urokinase inhibitors are synthesized chemically, they are relatively inexpensive to prepare and are of unusually high purity and defined chemical composition, resulting in low immunoreactivity and minimal side effects.

The selectivity of the instantly-claimed compounds for inhibition of urokinase over inhibition of other proteases such as tPA and plasmin and the fact that they inhibit reversibly prevents them from having thrombogenic properties.

The utility of such potent and specific urokinase inhibitors is highlighted by the broad range of invasive biological processes mediated by urokinase. These processes include, but are not limited to, angiogenesis (neovascularization), bone restructuring, embryo implantation in the uterus, infiltration of immune cells into inflammatory sites, ovulation, spermatogenesis, tissue remodelling during wound repair and organ differentiation, fibrosis, local invasion of tumors into adjacent areas, metastatic spread of tumor cells from primary to secondary sites, and tissue destruction in arthritis.

BRIEF DESCRIPTION OF THE DRAWINGS

The drawings will first briefly be described.

Drawings

Figure 1B:
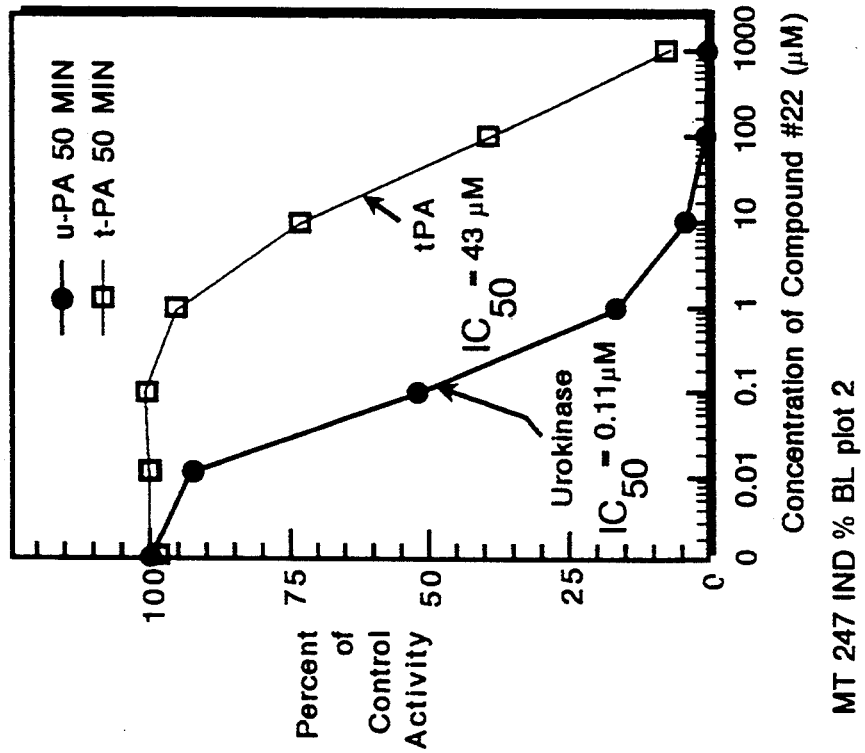
FIGS. 1A–C show inhibition of urokinase and tPA by compounds of the invention.

There now follows a description of the synthesis and characterization of sample urokinase inhibitors according to the invention. These examples are provided for the purpose of illustrating the invention, and should not be construed as limiting.

EXAMPLE 1

SYNTHESIS OF BENZOTHIOPHENE AMIDINE AND THIENOTHIOPHENE AMIDINE UROKINASE INHIBITORS

General Approach

Because very few 2-substituted benzothiophenes are commercially available, most were prepared using two novel synthetic routes for producing benzothiophenes from benzene derivatives. The major route (shown in Scheme 1). involves selective α-lithiation of a suitably substituted fluorobenzene derivative, followed by formylation with DMF to produce a 2-fluorobenzaldehyde derivative. By judicious control of lithiating conditions, this reaction is rather general and can accommodate a very useful range of functional groups. By careful control of conditions in the next step (which involves treatment of this benzaldehyde with methyl thioglycollate and base), the fluorine can be displaced with sulfur. Next, in a single step, an aldol condensation between the carbonyl of the aldehyde and the α-position of the ester is performed, followed by an elimination of water to aromatize the newly formed five membered ring. This process yields the desired 2, X,(Y)-di-(tri)-substituted benzothiophene in two steps from the fluoroaromatic precursor. In one particular example described in more detail below, this two step preparation provided the benzothiophene ester in 75% overall yield.

Scheme 1. Major Route to Benzothiophene-2-carboxamidines

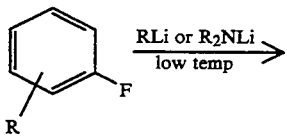

-continued
Scheme 1. Major Route to Benzothiophene-2-carboxamidines

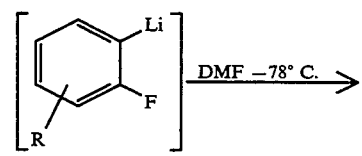

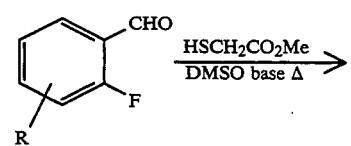

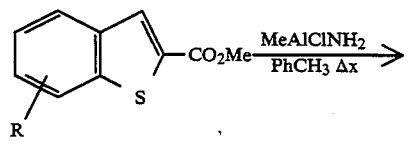

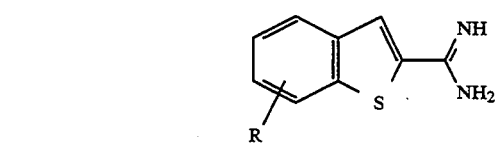

Because not all compounds according to the invention have simple fluorobenzene precursors directly available, a second route (shown in Scheme 2) was developed. Two compounds are used as synthetic intermediates, upon which sidechains (for example, long carbon sidechains) are added to the iodo and aldehyde groups. For the iodo compounds, Pd-catalyzed coupling reactions were utilized, mainly with stannanes and boranes; for the aldehyde compounds, organometallics and Wittig reagents were utilized.

Scheme 2. Elaboration of Carbon based Substituents from Readily Available Benzothiophenes.

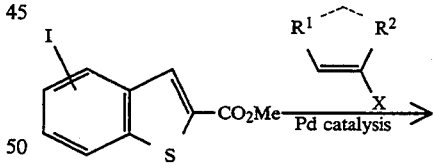

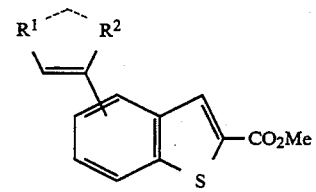

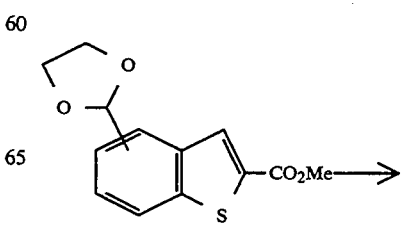

-continued
Scheme 2. Elaboration of Carbon based Substituents from Readily Available Benzothiophenes.

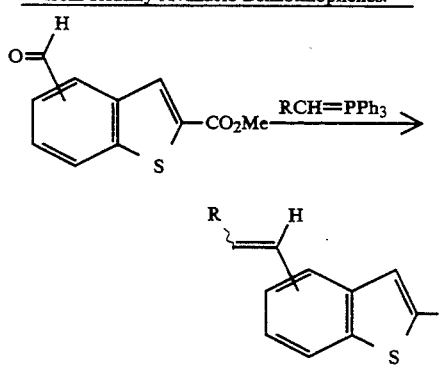

Once the desired benzothiophene 2-ester, acid, or nitrile was prepared, three different prior art methods were used for their conversion to amidines. Generally, an ester, nitrile or acid chloride (derived from the corresponding acid and thionyl chloride) is treated with "CH$_3$AlClNH$_2$", a reagent derived from Me$_3$Al and NH$_4$Cl in an aromatic hydrocarbon solvent. (For the amidination of esters: Basha, A.; Lipton, M.; Weinreb, S. M. *Tetrahedron Lett.* 1977, 4171. For the amidination of nitriles: Garigipati, R. M. *Tetrahedron Lett.* 1990, 31, 1969). Nitrile precursors are converted to amidines by treatment with NH$_3$/NH$_4$Cl at elevated temperature in a pressure bomb, or by treatment with LiN(SiCH$_3$)$_2$ in ether at 25° C., followed by aqueous HCl (Boere, R. T.; Oakley, R. T.; Reed, R. W. *J. Organomet. Chem.*, 1987, 331, 161). All of these methods yield the amidines as their hydrochloride salts, which is the form used for characterization of inhibitory potential and which would be the first form examined for therapeutic use.

Reagents and General Experimental Methods

Most compounds were purchased from Lancaster Synthesis or the Aldrich Chemical Co. and were used without further purification. THF was redistilled from Na/benzophenone. DMSO was kept over CaH$_2$. Toluene was Aldrich anhydrous grade, and xylenes were Fisher HPLC grade. Silica gel was E. Merck 70-230 mesh, and preparative chromatography plates were Analtech 20×20 cm silca gel plates of 0.1 or 0.2 cm thickness. $^1$H NMR spectra were taken at 400 MHz on a JEOL GSX400 or a Bruker AMX-400 spectrometer (NMR abbreviations: s=singlet, d=doublet, t=triplet, br=broad, sl=slightly). Melting points were taken on an Electrothermal IA9100 and are uncorrected.

LDA refers to lithium diisopropylamide, which was prepared from 1.0 equivalent of n-butyl lithium and 1.05 equivalents of undistilled Aldrich "Gold Label" diisopropylamine in THF at 0° C. LiTMP refers to lithium 2,2,6,6-tetramethylpiperidide, which was prepared from 1.0 equivalents of n-butyl lithium and 1.05 equivalents of Aldrich or Fluka 2,2,6,6-tetramethylpiperidine, (which was kept under a septum in the presence of Sumitomo "Sumistabiliser" anti-oxidant) in THF at 0° C.

All catalytic hydrogenations were deoxygenated by evacuation/argon atmosphere cycles and were carried out under 1 atmosphere of hydrogen using a balloon.

Large Scale Experimental Method

Preparation of 6-Fluoro-2-iodobenzaldehyde, Methyl 4-iodobenzo[b]thiophene-2-carboxylate, and 4-Iodobenzo[b]thiophene-2-carboxamidine hydrochloride (Compound 5)

Lithium diisopropylamide solution, (prepared at 0° C. under N$_2$ from n-butyl lithium (2.5M in hexanes, 105 mL, 0.263 mol) and diisopropylamine (27.8 g, 0.275 mol) in THF (200 mL) was added dropwise over 100 min, via catheter, to a solution of 3-fluoroiodobenzene (55.5 g, 0.25 mol) in THF (250 mL) stirred mechanically under N$_2$ at −78° C. After a further 15 min at −78° C., DMF (23.2 mL, 0.30 mol) was added dropwise over 15 min, producing a thick precipitate by the end of the addition. After a further 10 min the reaction was quenched at −78° C., by the rapid, sequential, addition of glacial acetic acid (60 mL) and water (500 mL). The phases were separated, and the aqueous phase was extracted with ether (2×250 mL). The combined organic extracts were washed with dilute hydrochloric acid (0.5M, 250 mL), water (2×250 mL), saturated brine (200 mL) and were dried (MgSO$_4$). The solvent was removed under reduced pressure to give 6-fluoro-2-iodobenzaldehyde (57.63 g, 92%) as a yellow-brown oil which spontaneously crystallised on standing: $^1$H NMR (CDCl$_3$). δ 10.14 (1H,d,J=0.9 Hz), 7.81 (1H,dt,J$_d$=7.3 Hz,J$_t$=1.2 Hz), 7.23, 7.18 (1H,1H,ABq of dd,J$_{AB}$=8.2 Hz,J$_d$=7.3,5.8; 9.5, 1.2 Hz).

Methyl thioglycollate (23 mL, 0.253 mol) was added over 1 min to a solution of 6-fluoro-2-iodobenzaldehyde (57.63 g, 0.23 mol) in DMSO (200 mL) stirred under N$_2$ at 25° C. A moderate exotherm was noted. Triethylamine (50.0 g, 0.5 mol) was added, and the mixture was heated to 60° C. for 90 min. The reaction mixture was poured slowly onto vigorously stirred ice-water (2L). After 30 min of stirring the light yellow precipitate was collected by Buchner filtration, and was rinsed with water (2×250 mL), and dried in a vacuum oven to give crude methyl 4-iodobenzo[b]thiophene-2-carboxylate (69.70 g, 95%), which was estimated by $^1$H NMR analysis to be ≧90% pure. A 10 g sample was most conveniently purified by stirring in MeOH (50 mL), cooling to −20° C., collecting the solid by Buchner filtration, rinsing with cold MeOH (2×20 mL) and air drying to give 8.66 g of ester (≧97% purity, 82% purified yield): $^1$H NMR (CDCl$_3$) δ 8.12 (1H,s), 7.82 (2H,d,J=8 Hz), 7.15 (1H,t,J=7.9 Hz), 3.97 (3H,s).

Trimethylaluminum (2.0M in toluene, 50 mL, 100 mmol) was added dropwise over 30 min to a slurry of ammonium chloride (5.35 g, 100 mmol) in toluene (50 mL), stirred under N$_2$ at 0° C. Trimethylaluminum is extremely reactive, and large amounts of gas are evolved during this experiment. Reactions should be carried out in flasks no more than 30% filled, and heating should be carried out slowly, and under careful scrutiny even on the scale described here. When gas evolution moderated, the mixture was stirred at 25° C. for 30 min, when most of the solid had dissolved. Methyl 4-iodobenzo[b]thiophene-2-carboxylate (8.66 g, 27.2 mmol) was added in one portion, dissolving to form a clear yellow solution. This solution was heated to reflux in stages over 1 h, vigorous gas evolution being seen in the 60°-100° C. range. After 2.5 h of reflux, the reaction mixture was allowed to cool to 25° C., and was poured onto a vigorously stirred slurry of silica gel (50 g) in CHCl$_3$ (500 mL). Mild exotherm and gas evolution were observed. After 20 min the solids were collected on a Buchner funnel, and washed with MeOH (3×250 mL). The combined filtrates were evaporated to dryness, and the residual yellow solid (10.75 g) was purified by flash chromatography on silica gel (800 g), eluting with 10%, then 20%, then 25% MeOH in CHCl$_3$. The yellow residue was dissolved in refluxing MeOH (100 mL) treated with activated charcoal (2 g) and filtered through a pad of Celite. The solvent was rigorously removed under reduced pressure at 65° C. to give 4-iodobenzo[b]thiophene-2-carboxamidine hydrochloride (Compound 5) (6.79 g, 74%) as a pale yellow, crystalline solid: $^1$H NMR (DMSO d$_6$) δ 9.67 (4H,br s), 8.40 (1H,s), 8.22 (1H,d,J=8.2 Hz), 7.96 (1H,d,J=7.6 Hz), 7.32 (1H,t,J=7.9 Hz).

These methods (as generally described for the synthesis of Compound 5) are utilized for the preparation of compounds described below.

Small Scale Experimental Method

Preparation of 2-(3-Fluorophenyl)-1,3-dioxolane, 2-(1,3-Dioxolan-2-yl)-6-fluorobenzaldehyde, Methyl 4-(1,3-dioxolan-2-yl)benzo[b]thiophene-2-carboxylate, Methyl 4-formylbenzo[b]thiophene-2-carboxylate, Methyl 4-(E/Z-3-methylbut-1-enyl)benzo[b]thiophene-2-carboxylate, and 4-(E/Z-3-Methylbut-1-enyl)benzo[b]thiophene-2-carboxamidine hydrochloride (Compound 22).

A solution of 3-fluorobenzaldehyde (12.41 g, 100 mmol), ethane-1,2-diol (6.82 g, 110 mmol) and tosic acid monohydrate (0.19 g, 1 mmol) in toluene (50 mL) was refluxed in a Dean-Stark apparatus under N$_2$ for 18 h. On cooling, the reaction mixture was washed with saturated NaHCO$_3$ solution (50 mL), water (2×50 mL), saturated brine (50 mL) and dried (MgSO$_4$). The solvent was rigorously removed under reduced pressure to give 2-(3-fluorophenyl)-1,3-dioxolane (15.46 g, 92%) as a light yellow oil: $^1$H NMR (CDCl$_3$) δ 7.35 (1H,dt,J$_d$=5.5 Hz,J$_t$=7.9 Hz), 7.25 (1H,dt,J$_d$=7.6 Hz,J$_t$=1.5 Hz), 7.20 (1H,ddd,J=1.5,2.4,9.5 Hz), 7.05 (1H,dd of t,J$_d$=1,2.4 Hz,J$_t$=8.4 Hz), 5.81 (1H,s), 4.15-4.00 (4H,m).

n-Butyl lithium (2.3M in hexanes, 4.4 mL, 10.1 mmol) was added dropwise over 5 min to a solution of 2-(3-fluorophenyl)-1,3-dioxolane (1.68 g, 10 mmol) and N,N,N',N'-tetramethylethylene diamine (TMEDA, 1.16 g, 10 mmol) in THF (20 mL), stirred under N$_2$ at −78° C. After 5 h at that temperature, DMF (0.86 g, 12 mmol) was added dropwise over 2 min. After a further 10 min the −78° C. mixture was quenched by the rapid addition of glacial acetic acid (2 mL), and the reaction was poured onto water (50 mL) and extracted with ether (3×20 mL). The combined organic extracts were washed with water (2×20 mL), saturated brine (20 mL) and dried (MgSO$_4$). The solvent was removed under reduced pressure to give crude 2-(1,3-dioxolan-2-yl)-6-fluorobenzaldehyde (1.80 g, 91%) as a light yellow oil: $^1$H NMR (CDCl$_3$) δ 7.61-7.56 (2H,m), 7.22 (1H,m) 6.50 (1H,s), 4.13-4.04 (4H,m).

Methyl thioglycollate (0.81 mL, 9 mmol) was added dropwise over 10 min to a stirred suspension of hexane-washed NaH (60% oil suspension, 493 mg, 12.3 mmol) in DMSO (5 mL) at 10° C. under N$_2$. When gas evolution died down, the light yellow solution was stirred at 25° C. for 10 min, and 2-(1,3-dioxolan-2-yl)-6-fluorobenzaldehyde (1.80 g 9 mmol) in DMSO (5 mL) was added over 1 min. There was gas evolution, a strong exotherm and the reaction mixture became a bright orange red solution. After a further 2 min, the reaction mixture was slowly poured onto vigorously stirred ice-water (100 mL). After 15 min the mixture was Buchner filtered, and the residue was rinsed with water (2×20 mL) and air dried to give methyl 4-(1,3-dioxolan-2-yl)benzo[b]thiophene-2-carboxylate (1.35 g, 56%) as a cream colored powder: $^1$H NMR (CDCl$_3$) δ 8.34 (1H,d,J=0.7 Hz), 7.88 (1H,d,J=8.1 Hz), 7.57 (1H,dd,J=7.1,0.7 Hz), 7.46 (1H,dd,J=7.1,8.1 Hz), 6.20 (1H,s), 4.23-4.10 (4H,m), 3.95 (3H,s).

A solution of methyl 4-(1,3-dioxolan-2-yl)benzo[b]thiophene-2-carboxylate (528.2 mg, 2.0 mmol) in acetonitrile/acetone/water (4.5, 2.5, 0.5 mL) containing trifluoroacetic acid (15 drops) was stirred under N$_2$ at 25° C. for 2.5 h. The heavily precipitated mixture was cooled to 0° C. for 30 min, and the solid was collected by Buchner filtration, rinsed with water, (2×10 mL) and air dried to give methyl 4-formylbenzo[b]thiophene-2-carboxylate (330 mg, 75%) as fine, off-white needles: $^1$H NMR (CDCl$_3$) δ 10.24 (1H,s), 9.03 (1H,d,J=0.6 Hz), 8.14 (1H,dd,J=1,8 Hz) 7.91 (1H,dd,J=1,7.1 Hz) 7.66 (1H,dd,J=7,8 Hz), 3.98 (3H,s).

A solution of potassium t-butoxide in THF (0.54M, 0.60 mL, 0.32 mmol) was added dropwise to a slurry of iso-butyltriphenylphosphonium bromide (140.8 mg, 0.35 mmol) in THF (5 mL), stirred under N$_2$ at −78° C. After 1 h at −78° C., a solution of 4-formylbenzo[b]thiophene-2-carboxylate (64.7 mg, 0.29 mmol) in THF (5 mL) was added slowly. After 10 min the reaction mixture allowed to warm up to 25° C. for 20 min, and was passed through a silica gel plug (7 g) eluting with 10% MeOH/CHCl$_3$. The solvent was removed under reduced pressure, and the residue was purified by preparative thin layer chromatography (tlc), eluting with 0.6% MeOH/CHCl$_3$. The solvent was removed under reduced pressure to give methyl 4-(E/Z-3-methylbut-1-enyl)benzo[b]thiophene-2-carboxylate (51.2 mg, 67%, Z/E=3:2) as a colorless syrup: $^1$H NMR (CDCl$_3$) E-isomer: δ 8.29 (1H,s), 7.68 (1H,d,J=8 Hz), 7.48 (1H,d,J=8 Hz), 7.38 (1H,t,J=8 Hz), 6.83 (1H,d,J=16 Hz), 6.32 (1H,dd,J=16,7 Hz), 3.96 (3H,s), 2.56 (1H,m), 1.15 (6H,d,J=7 Hz); Z-isomer: δ 8.14 (1H,s), 7.74 (1H,d,J=8 Hz), 7.41 (1H,t,J=7.5 Hz), 7.27 (1H,d,J=7 Hz), 6.63 (1H,d,J=11 Hz), 5.70 (1H,dd,J=11,10 Hz), 3.94 (3H,s), 2.69 (1H,m), 1.01 (6H,d,J=6.5 Hz).

Trimethylaluminium (2.0M in toluene, 0.5 mL, 1 mmol) was added dropwise to a slurry of ammonium chloride (53 mg, 1 mmol) in xylene (2 mL), stirred under N$_2$ at 0° C. When gas evolution moderated, the mixture was stirred at 25° C. for 30 min, and was then added to a solution of 4-(E/Z-3-methylbut-1-enyl)benzo[b]thiophene-2-carboxylate (51.2 mg, 0.2 mmol) in xylene (2 mL). The mixture was refluxed for 3 h under N$_2$, and allowed to cool to 25° C. It was poured onto a vigorously stirred slurry of silica gel (2 g) in CHCl$_3$ (15 mL). After 20 min the mixture was Buchner filtered, and the residue was washed with MeOH (30 mL). The combined filtrates were evaporated to dryness, and the residual yellow solid was purified by flash chromatography on silica gel (6 g), eluting with 15% MeOH/CHCl$_3$. The desired fractions were concentrated under reduced pressure, dissolved up in water, and lyophilised to give 4-(E/Z-3-methylbut-1-enyl)benzo[b]thiophene-2-carboxamidine hydrochloride (40.0 mg, 72%, E/Z=1:1) as a fluffy yellow solid: $^1$H NMR (CD₃OD) E-isomer: δ 8.56 (1H,d,J=1.0 Hz), 7.87 (1H,d,J=8.1 Hz), 7.64 (1H,d,J=7.6 Hz), 7.53 (1H,t,J=7.8 Hz), 6.94 (1H,d,J=15.9 Hz), 6.48 (1H,dd,J=15.9,7.1 Hz), 4.91 (3H, br s), 2.60 (1H,m), 1.18 (6H,d,J=6.8 Hz); Z-isomer: δ 8.35 (1H,s), 7.92 (1H,d,J=8.1 Hz), 7.57 (1H,t,J=7.8 Hz), 7.40 (1H,d,J=7.3 Hz), 6.74 (1H,d,J=11.6 Hz), 5.78 (1H,dd,J=11.6,10.1 Hz), 4.91 (3H,br s), 2.74 (1H,m), 1.03 (6H,d,J=6.5 Hz).

These methods (as generally described for the synthesis of Compound 5) are utilized for the preparation of compounds described below.

Compound 1

Benzo[b]thiophene-2-carboxamidine hydrochloride

Benzothiophene-2-carboxylic acid was converted to the corresponding acid chloride by refluxing for 90 min in neat SOCl₂, and 1 mmol of the acid chloride was treated with 4 equivalents of Me₃Al/NH₄Cl in refluxing toluene for 2 h, to give, after workup and purification, benzo[b]thiophene-2-carboxamidine hydrochloride (188.8 mg, 89%) as an offwhite solid: ¹H NMR (DMSO d₆) δ 9.52 (4H,br s), 8.44 (1H,s), 8.20 (1H,d,J=7.6 Hz), 8.07 (1H,d,J=7.6 Hz), 7.60 (1H,dt,J_d=1.2 Hz,J_t=7.6 Hz), 7.54 (1H,dt,J_d=1.2 Hz,J_t=7.6 Hz).

Compound 2

4-Fluorobenzo[b]thiophene-2-carboxamidine hydrochloride 2,6-Difluorobenzaldehyde was reacted with methyl thioglycollate and NaH in DMSO to give methyl 4-fluorobenzo[b]thiophene-2-carboxylate in 84% yield. Amidination of this (0.7 mmol) was carried out with 4 equivalents of Me₃Al/NH₄Cl in toluene at 90° C. for 4 h to give, after workup and purification, 4-fluorobenzo[b]thiophene-2-carboxamidine hydrochloride hexahydrate (237 mg, 97%) as a light yellow solid: ¹H NMR (CD₃OD) δ 8.36 (1H,d,J=0.7 Hz), 7.87 (1H,d,J=8.3 Hz), 7.61 (1H,dt,J_d=5.1 Hz,J_t=8.2 Hz), 7.26 (1H,ddd,J=0.7,8.1,10.1 Hz), 4.91 (16H, br s).

Compound 3

4-Chlorobenzo[b]thiophene-2-carboxamidine hydrochloride

Prepared in the usual fashion from 2-chloro-6-fluorobenzaldehyde, the ester being obtained in 70% yield, and 4-chlorobenzo[b]thiophene-2-carboxamidine hydrochloride trihydrate (210.6 mg, quantitative yield) obtained as a light yellow solid: ¹H NMR (CD₃OD) δ 8.42 (1H, d,J=0.7 Hz), 8.01 (1H,m), 7.59–7.54 (2H,m), 4.90 (10H,br s).

Compound 4

4-Bromobenzo[b]thiophene-2-carboxamidine hydrochloride

1-Bromo-3-fluorobenzene was formylated with LDA and DMF (cf Compound 5) in 75% yield. This benzaldehyde was converted into the the benzothiophene ester in 45% yield, and was amidinated, as described for Compound 2, to give 4-bromobenzo[b]thiophene-2-carboxamidine hydrochloride hexahydrate (194.4 mg, 88%) as a light yellow solid: ¹H NMR (CD₃OD) δ 8.40 (1H,d,J=0.7 Hz), 8.05 (1H,d,J=8.3 Hz), 7.75 (1H,dd,J=7.6,0.7 Hz), 7.49 (1H,t,J=7.9 Hz), 4.90 (16H,br,s).

Compound 6

4-Methylbenzo[b]thiophene-2-carboxamidine hydrochloride

Methyl 4-methylbenzo[b]thiophene-2-carboxylate was isolated as the major product from the attempted palladium-mediated coupling of methyl 4-iodobenzo[b]thiophene-2-carboxylate and 1-(trimethylstannyl)naphthalene. The stannane was prepared in quantitative yield by treatment of 1-bromonaphthalene (1.51 mmol) with t-butyl lithium (2.02 equiv, THF, −78° C., 15 min) followed by addition of chlorotrimethyltin (1.12 equiv, −78° C. to 0° C.) and aqueous workup.

A mixture of the stannane (234.3 mg, 0.80 mmol), the iodide (209.4 mg, 0.66 mmol, Compound 5), bis(triphenylphosphine)palladium(II) chloride (28.3 mg, 0.04 mmol), and powdered, anhydrous LiCl (89.0 mg, 2.09 mmol) in DMF (5 mL) was heated at 80° C. for 5.3 hr. An additional 15 mg of the Pd(II) catalyst was added, and the reaction mixture heated for 22 hr. After cooling to room temperature, the reaction mixture was diluted with EtOAc, washed with water (2×), 10% aq. NH₄OH, saturated brine, and dried (MgSO₄). After filtration and solvent removal, the residue was purified by flash chromatography (5% EtOAc/hexane) to provide 29.1 mg of methyl 4-methylbenzo[b]thiophene-2-carboxylate as a white, crystalline solid.

This ester (72.1 mg, 0.35 mmol) was treated with 5.2 equiv of Me₃Al/NH₄Cl (xylene, 130° C., 5 hr) to afford, after workup and silica gel chromatography (15% MeOH/CHCl₃), 4-methylbenzo[b]thiophene-2-carboxamidine hydrochloride (32.2 mg, 41%) as an offwhite solid: ¹H NMR (CD₃OD) δ 8.46 (1H,s), 7.89 (1H,d,J=8.3 Hz), 7.53 (1H,t,J=8.0 Hz), 7.37 (1H,d,J=8.0 Hz), 4.96 (4H,br s), 2.74 (3H,s).

Compound 7

4-Ethylbenzo[b]thiophene-2-carboxamidine hydrochloride

A mixture of 4-ethenylbenzo[b]thiophene-2-carboxamidine hydrochloride (30.1 mg, 0.13 mmol, Compound 17) and 10% Pd/C (ca. 50 mg) in MeOH (5 mL) was stirred under an atmosphere of H₂ for 80 minutes. The catalyst was filtered off through a Celite plug which was then washed with further MeOH. The filtrates were evaporated to dryness, and the crude orange solid was purified by preparative tlc (20% CH₃OH/CHCl₃) to afford 4-ethylbenzo[b]thiophene-2-carboxamidine hydrochloride (5.8 mg, 19%) as light yellow glass: ¹HNMR (CD₃OD) δ 8.54 (1H,s), 7.87 (1H,d,J=8.0 Hz), 7.54 (1H,t,J=8.0 Hz), 7.31 (1H,d,J=8.0 Hz), 4.91 (4H,br s), 3.06 (2H,q,J=7.0 Hz), 1.37 (3H,t,J=7.0 Hz).

Compound 8

4-(1-Methylethyl)benzo[b]thiophene-2-carboxamidine hydrochloride

To a solution of methyl 4-formylbenzo[b]thiophene-2-carboxylate (743.4 mg, 3.4 mmol, Compound 22) in THF (10 mL) at −78° C. was added methylmagnesium bromide (3M, 1.75 mL, 5.25 mmol). The reaction was quenched after 35 minutes with saturated NaHCO₃ solution and extracted into Et₂O (2×). The combined organic layers were dried (MgSO₄). Filtration and solvent removal followed by step gradient flash chromatography (CHCl₃ then 2% CH₃OH/CHCl₃) yielded methyl 4-(1-hydroxyethyl)benzo[b]thiophene-2-carboxylate (798.4 mg, 100%) as clear, colorless syrup.

To a solution of oxalyl chloride (182 µL, 2.1 mmol) in $CH_2Cl_2$ (8 mL) at −78° C. was added DMSO (297 µL, 4.2 mmol). After 5 min a solution of methyl 4-(1-hydroxyethyl)benzo[b]thiophene-2-carboxylate (411.8 mg, 1.7 mmol) in $CH_2Cl_2$ (3 mL) was added via cannula. After an additional 10 minutes $Et_3N$ (972 µL, 7.0 mmol) was added. The reaction mixture was warmed to 25° C. over 10 minutes and then diluted with $CHCl_3$ and washed with saturated aqueous $NaHCO_3$ solution. The organic layer was dried ($MgSO_4$), filtered, and evaporated to dryness to afford methyl 4-acetylbenzo[b]thiophene-2-carboxylate (401.8 mg, 98%) as light beige solid.

To a stirred suspension of methyltriphenylphosphonium iodide (381.5 mg, 0.94 mmol) in THF (5 mL) at −78° C. was added potassium tert-butoxide in THF (0.54M, 1.67 mL). After 50 min a solution of methyl 4-acetylbenzo[b]thiophene-2-carboxylate (201.0 mg, 0.86 mmol) in THF (5 mL) was added. The reaction was warmed to 25° C. over 30 min and the brown mixture was filtered through a silica gel plug with 10% $CH_3OH/CHCl_3$. The crude material obtained after solvent removal was purified by preperative tlc (0.7% $CH_3OH/CHCl_3$) to afford methyl 4-(1-methylethenyl)benzo[b]thiophene-2-carboxylate (136.4 mg, 68%) as a clear, colorless syrup.

A mixture of this material (61.6 mg, 0.27 mmol) and 10% Pd/C (ca. 100 mg) in THF (2 mL) was stirred under an atmosphere of $H_2$ for 15.5 h. Celite filtration and solvent removal provided methyl 4-(1-methylethyl)benzo[b]thiophene-2-carboxylate (58.5 mg, 94%) as pale golden syrup.

To a solution of this material (58.5 mg, 0.25 mmol) in xylenes (5 mL) was added a solution of $Me_3Al/NH_4Cl$ (0.5M, 2.1 mL) in toluene. The mixture was heated to 115° C. for 4 h to afford after the usual workup 4-(1-methylethyl)benzo[b]thiophene-2-carboxamidine hydrochloride (48.1 mg, 76%) as a pale yellow film: $^1H$ NMR ($CD_3OD$) δ 8.55 (1H,s), 7.89 (1H,d,J=8.2 Hz), 7.60 (1H,t,J=7.98 Hz), 7.48 (1H,d,J=7.3 Hz), 4.95 (4H,br s), 3.62 (2H,m,), 1.45 (6H,d,J=6.9 Hz).

Compound 9

4-Propylbenzo[b]thiophene-2-carboxamidine hydrochloride

A mixture of 4-(prop-2-enyl)benzo[b]thiophene-2-carboxamidine.hydrochloride hydrochloride (42.4 mg, 0.16 mmol, Compound 19) and 10% Pd/C (39.4 mg) in MeOH (4 mL) was stirred under an atmosphere of $H_2$ for 1.2 hr. celite filtration and solvent removal provided 4-propylbenzo[b]thiophene-2-carboxamidine hydrochloride (36.2 mg, 85%) as an offwhite solid: $^1H$ NMR ($CD_3OD$) δ 8.53 (1H,s), 7.89 (1H,d,J=8.0 Hz), 7.54 (1H,t,J=7.8 Hz), 7.36 (1H,d,J=7.3 Hz), 5.02 (4H,br s), 3.04 (2H,t,J=7.6 Hz), 1.81 (2H,sextet,J=7.3 Hz), 1.05 (3H,t,J=7.3 Hz).

Compound 10

4-Butylbenzo[b]thiophene-2-carboxamidine hydrochloride

A mixture of 4-(E/Z-1-butenyl)benzo[b]thiophene-2-carboxamidine hydrochloride (59.0 mg, 0.22 mmol, Compound 20) and 10% Pd/C (ca. 50 mg) in MeOH (2 mL) was stirred under an atmosphere of $H_2$ for 2.5 h. The reaction mixture was filtered through Celite, the residue washed with MeOH, and the filtrate was evaporated to dryness. Analysis by $^1H$ NMR (d$_6$-DMSO) showed the presence of starting material so the crude mixture was resubmitted to hydrogenation under the same conditions as above for 5 h. Celite iltration and solvent removal under reduced pressure afforded 4-butylbenzo[b]thiophene-2-carboxamidine hydrochloride (41.9 mg, 70%) as a pale beige solid: $^1HNMR$ ($CD_3OD$) δ 8.49 (1H,s), 7.90 (1H,d,J=8.0 Hz), 7.55 (1H,t,J=7.4 Hz), 7.39 (1H,d,J=7.4 Hz), 4.96 (4H,br s), 3.09 (2H,t,J=7.7 Hz), 1.78 (2H,m), 1.50 (2H,m), 1.03 (3H,t,J=7.3 Hz).

Compound 11

4-([R/S]-2-Methylbutyl)benzo[b]thiophene-2-carboxamidine hydrochloride

A mixture of 4-(E/Z-2-methylbut-1-enyl)benzo[b]thiophene-2-carboxamidine hydrochloride (3.3 mg, 0.012 mmol, Compound 21) and 10% Pd/C (ca. 10 mg) in MeOH (1 mL) was stirred under an atmosphere of $H_2$ for 19 h. Celite filtration and solvent removal provided 4-([R,S]-2-methylbutyl)benzo[b]thiophene-2-carboxamidine hydrochloride (3.9 mg, quant.) as a white glass: $^1HNMR$ ($CD_3OD$) δ 8.44 (1H,s), 7.90 (1H,d,J=8.0 Hz), 7.55 (1H,t,J=7.4 Hz), 7.35 (1H,d,J=7.3 Hz), 4.96 (4H,br s), 3.10 (1H,dd,J=13.6,6.3 Hz), 2.84 (1H,dd,J=13.5,8.5 Hz), 1.87 (1H,m), 1.53 (1H,m), 1.32 (1H,m), 1.01 (3H,t,J=7.5 Hz), 0.95 (3H,d,J=6.5 Hz).

Compound 12

4-(3-Methylbutyl)benzo[b]thiophene-2-carboxamidine hydrochloride

A mixture of 4-(E/Z-3-methylbut-1-enyl)benzo[b]thiophene-2-carboxamidine hydrochloride (32.6 mg, 0.12 mmol, Compound 22) and 10% Pd/C (ca. 30 mg) in MeOH (5 mL) was stirred under an atmosphere of $H_2$ for 17 h. Celite filtration and solvent removal provided 4-(3-methylbutyl)benzo[b]thiophene hydrochloride (28.1 mg, 86%) as yellow film which was dissolved in water (10 mL) and evaporated to dryness to give a light beige fluffy solid: $^1H$ NMR ($CD_3OD$) δ 8.47 (1H,s), 7.91 (1H,d,J=8.0 Hz), 7.55 (1H,t,J=8.0 Hz), 7.39 (1H,d,J=8.0 Hz), 4.95 (4H,br s), 3.09 (2H,t,J=7.9 Hz), 1.78–1.62 (3H,m), 1.06 (6H,d,J=6.3 Hz).

Compound 13

4-(Hexyl)benzo[b]thiophene-2-carboxamidine hydrochloride

A mixture of 4-(E/Z-hex-1-enyl)benzo[b]thiophene-2-carboxamidine hydrochloride (32.3 mg, 0.11 mmol, Compound 29) and 10% Pd/C (ca. 50 mg) in MeOH (5 mL) was stirred under an atmosphere of $H_2$ for 22.5 h. Celite filtration and solvent removal provided 4-hexylbenzo[b]thiophene-2-carboxamidine hydrochloride (27.4 mg, 84%) as a yellow film: $^1H$ NMR ($CD_3OD$) δ 8.45 (1H,s), 7.84 (1H,d,J=8.1 Hz), 7.49 (1H,t,J=7.3 Hz), 7.32 (1H,d,J=7.2 Hz), 4.95 (4H,br s), 3.02 (2H,t,J=7.8 Hz), 1.73 (2H,m), 1.26–1.40 (6H,m), 0.89 (3H,t,J=5.0 Hz).

Compound 14

4-(2-Cyclopropylethyl)benzo[b]thiophene-2-carboxamidine hydrochloride

A mixture of 4-(E/Z-2-cyclopropylethenyl)benzo[b]thiophene-2-carboxamidine hydrochloride (27.7 mg, 0.10 mmol, Compound 33) and 10% Pd/C (ca. 30 mg) in MeOH (4 mL) was stirred under an atmosphere of $H_2$ for 23 h. Celite filtration and solvent removal provided 4-(2-cyclopropylethyl)benzo[b]thiophene-2-carboxamidine hydrochloride (25.0 mg, 89%) as a pale orange film: $^1$HNMR (CD$_3$OD) δ 8.50 (1H,s), 7.90 (1H,d,J=8.2,7.3 Hz), 7.41 (1H,d,J=8.0 Hz), 4.96 (4H,br s), 1.69 (2H,dd,J=7.9,7.2 Hz), 0.81 (1H,m), 0.49 (2H,m), 0.12 (2H,m).

Compound 15

4-(2-Phenylethyl)benzo[b]thiophene-2-carboxamidine hydrochloride

A mixture of 4-(E/Z-2-phenylethenyl)benzo[b]thiophene-2-carboxamidine hydrochloride (28.3 mg, 0.09 mmol, Compound 63) and 10% Pd/C in MeOH (5 mL) was stirred under an atmosphere of $H_2$ for 29 hr. Celite filtration and solvent removal provided 4-(2-phenylethyl)benzo[b]thiophene-2-carboxamidine hydrochloride (23.9 mg, 84%) as an offwhite solid: $^1$H NMR (CD$_3$OD) δ 8.37 (1H,s), 7.88 (1H,d,J=8.3 Hz), 7.49 (1H,dd,J=7.8,7.6 Hz), 7.30 (1H,d,J=7.3 Hz), 7.24 (2H,d,J=7.3 Hz), 7.20–7.18 (3H,m), 5.00 (4H,br s), 3.35 (2H,br t,J=7.8 Hz), 3.06 (2H,br t,J=7.8 Hz).

Compound 16

4-(1-Phenylethyl)benzo[b]thiophene-2-carboxamidine hydrochloride

To a stirring solution of 4-formylbenzo[b]thiophene-2-carboxylate (247.3 mg, 1.1 mmol) in THF (15 mL) at −78° C. was added a solution of phenylmagnesium bromide (3M, 374 μL) in Et$_2$O. After 20 min the reaction was quenched with saturated NaHCO$_3$ solution, filtered, and evaporated to dryness to afford after flash chromatography (2% CH$_3$OH/CHCl$_3$) methyl 4-(1-phenylhydroxymethyl) benzo[b]thiophene-2-carboxylate (388.8 mg, 94%) as a colorless syrup.

To this material (122.8 mg, 0.41 mmol) was added a solution of NH$_4$Cl/Me$_3$Al (0.43M, 7.6 mL). The mixture was heated at 125° C. for 18 h and then poured onto a vigorously stirred slurry of silica gel in CHCl$_3$. The slurry was filtered, the residue was washed with MeOH, and the filtrate was concentrated under reduced pressure. The crude solid was purified by preparative tlc (20% CH$_3$OH/CHCl$_3$) to provide 4-(1-phenylethyl)-benzo[b]thiophene-2-carboxamidine hydrochloride (37.7 mg, 29%) as a beige solid. $^1$H NMR (DMSO d$_6$) δ 10.34 (4H,v br s), 9.65 (1H,s), 8.83 (1H,d,J=8.2 Hz), 8.37 (1H,t,J=7.8 Hz), 8.26 (1H,d,J=7.3 Hz), 8.21 (2H,d,J=8.0 Hz), 8.09 (2H,t,J=7.6 Hz), 7.98 (1H,t,J=7.3 Hz), 5.59 (1H,q,J=7.1 Hz), 2.51 (3H,d,J=7.0 Hz).

Compound 17

4-Ethenylbenzo[b]thiophene-2-carboxamidine hydrochloride

To a stirred suspension of methyltriphenylphosphonium iodide (384.0 mg, 0.95 mmol) in THF (10 mL) at −78° C. was added a solution of potassium tert-butoxide in THF (0.54M, 1.7 mL). After 30 min a solution of methyl 4-formylbenzo[b]thiophene-2-carboxylate (190.2 mg, 0.91 mmol, Compound 22) in THF (5 mL) was added via cannula. The reaction was stirred at 0° C. for 1 h, after which time the mixture was filtered through a silica plug with 10% CH$_3$OH/CHCl$_3$ and evaporated to dryness under reduced pressure. The crude material was purified by flash chromatography (20% EtOAc/Hexanes) to yield methyl 4-ethenylbenzo[b]thiophene-2-carboxylate (171.3 mg, 91%) as a light yellow, wet-looking solid.

To this material (171.5 mg, 0.79 mmol) was added a solution of Me$_3$Al/NH$_4$Cl (0.67M, 10 mL) in xylenes. The mixture was heated to 125° C. for 2 h, cooled to 25° C. and then poured onto a vigorously stirred slurry of silica gel in CHCl$_3$ (30 mL). The slurry was filtered, the residue was washed with 10% aq. MeOH, and the filtrate was concentrated under reduced pressure, and the crude solid was chromatographed (30% MeOH/CHCl$_3$). Analysis by $^1$H NMR (d$_6$-DMSO) showed there to be 2 molar equiv of NH$_4$Cl in the isolated product. The material was dissolved in water, the pH was raised to 12 with NaOH solution(0.2M), the solution was evaporated to dryness, reacidified with dilute hydrochloric acid, and evaporated to dryness. Flash chromatography on silica gel (30% CH$_3$OH/CHCl$_3$) yielded 4-ethenylbenzo[b]thiophene-2-carboxamidine hydrochloride trihydrate (115.2 mg, 50%) as an orange solid: $^1$H NMR (DMSO d$_6$) δ 9.55 (2H,br s), 9.22 (2H,br s), 8.77 (1H,s), 8.14 (1H,d,J=7.5 Hz), 7.60 (1H,t,J=7.9 Hz), 7.31 (1H,dd,J=16.0,8.0 Hz), 6.10 (1H,d,J=16.0 Hz), 5.59 (1H,d,J=8.0 Hz), 2.77 (6H,br s).

Compound 18

4-(1-Methylethenyl)benzo[b]thiophene-2-carboxamidine hydrochloride

To a solution of methyl 4-(1-methylethenyl)benzo[b]thiophene-2-carboxylate (74.8 mg, 0.32 mmol, Compound 8) in xylenes (5 mL) was added a solution of Me$_3$Al/NH$_4$Cl (0.6M, 2.7 mL) in xylenes. The reaction was heated to 115° C. for 3.5 h then cooled to 25° C. to yield, after workup and flash chromatography (15% MeOH/CHCl$_3$), 4-(1-methylethenyl)benzo[b]thiophene-2-carboxamidine hydrochloride (62.7 mg, 77%) as a slightly yellow solid: $^1$H NMR (DMSO-d$_6$) δ 9.59 (2H,br.s), 8.54 (1H,s), 8.48 (1H,d,J=8.2 Hz), 8.10 (1H,t,J=7.0 Hz), 7.56 (1H,d,J=7.5 Hz), 7.42 (1H,d,J=7.4 Hz), 5.44 (1H,s), 5.26 (1H,s), 2.21 (3H,s).

Compound 19

4-(Prop-2-enyl)benzo[b]thiophene-2-carboxamidine hydrochloride

A mixture of methyl 4-iodobenzo[b]thiophene-2-carboxylate (204.5 mg, 0.64 mmol, Compound 5), allytri-n-butyltin (220 μl, 0.71 mmol), bis(triphenylphosphine)-palladium(II) chloride (21.8 mg, 0.03 mmol) and LiCl (83.1 mg, 1.96 mmol) in DMF (5 mL) was heated at 90° C. for 1.25 h. Workup and chromatographic purification (8% EtOAc/hexane) afforded methyl 4-(prop-2-enyl)benzo[b]thiophene-2-carboxylate (113.4 mg, 76%) as an oil. This material (113.4 mg, 0.49 mmol) was treated with 5.3 equiv of Me$_3$Al/NH$_4$Cl (xylene, 130° C., 3.5 hr) to provide, after workup and chromatographic purification (15% MeOH/CHCl$_3$), 4-(prop-2-enyl)benzo[b]thiophene-2-carboxamidine hydrochloride (118.8 mg, 94%) as an offwhite solid containing ca. 4% of 4(E-prop-1-enyl)benzo[b]thiophene-2-carboxamidine hydrochloride (as estimated by $^1$H NMR integration): $^1$H NMR (CD$_3$OD) δ 8.48 (1H,s), 7.94 (1H,d,J=8.3 Hz), 7.58 (1H,t,J=7.8 Hz), 7.40 (1H,d,J=7.3 Hz), 6.14 (1H,ddt,J$_d$=17.5,9.8 Hz, J$_t$=6.3 Hz), 5.16 (1H,d,J=9.8 Hz), 5.15 (1H,d,J=17.5 Hz), 5.15 (4H,br s), 3.85 (2H,d,J=6.3 Hz).

Compound 20

4-(E/Z-But-1-enyl)benzo[b]thiophene-2-carboxamidine hydrochloride n-Propyltriphenylphosphonium bromide was reacted with potassium tert-butoxide and methyl 4-formylbenzo[b]thiophene-2-carboxylate, as described in Compound 17, to afford methyl 4-(E/Z-but-1-enyl)benzo[b]thiophene-2-carboxylate (75.8 mg. 73%) as a golden syrup after preparative tlc purification (0.6% MeOH/CHCl$_3$).

To a solution of this ester (75.8 mg, 0.31 mmol) in xylenes (3 mL) was added a solution of Me$_3$Al/NH$_4$Cl (0.5M, 3.1 mL) in xylenes. The mixture was heated to 140° C. for 2.75 h to afford, after workup and flash chromatography (15% CH$_3$OH/CHCl$_3$) 4-(E/Z-but-1-enyl)benzo[b]thiophene-2-carboxamidine hydrochloride decahydrate (79.2 mg, 58%, E/Z=2:3) as an orange solid: $^1$H NMR (CD$_3$OD) E-and Z-isomers δ 8.62 (1H,s), 8.40 (1H,s), 7.97 (1H,d,J=8.2 Hz), 7.92 (1H,d, J=7.7 Hz), 7.69 (1H,d,J=7.4 Hz), 7.57–7.64 (2H,m), 7.45 (1H,d,J=7.6 Hz), 7.03 (1H,d. J=16.4 Hz), 6.88 (1H,d,J=11.3 Hz), 6.59 (1H,dt,J$_d$=15.6 Hz,J$_t$=7.0 Hz), 6.03 (1H,dt, J$_d$=11.3 Hz,J$_t$=7.2 Hz), 4.95 (24H,br s), 2.42 (2H,m), 2.30 (2H,m), 1.24 (3H,t,J=6.0 Hz), 1.09 (3H,t,J=6.0 Hz).

Compound 21

4-(E/Z-2-Methylbut-1-enyl)benzo[b]thiophene-2-carboxamidine hydrochloride

2-Butyltriphenylphosphonium bromide (131.0 mg, 0.33 mmol) was reacted with potassium tert-butoxide and methyl 4-formylbenzo[b]thiophene-2-carboxylate, as described in Compound 17, to afford, after preparative tlc (13% EtOAc/hexanes), methyl 4-(E/Z-2-methyl-but-enyl)benzo[b]thiophene-2-carboxylate (18.6 mg, 26%) as a yellow syrup.

To a solution of this ester (18.6 mg, 0.07 mmol) in xylenes (3 mL) was added a solution of Me$_3$Al/NH$_4$Cl in xylenes (0.5M, 1.1 mL). The mixture was refluxed for 4.5 h to afford, after workup and chromatography (15% MeOH/CHCl$_3$), 4-(E/Z-2-methybutenyl)benzo[b]thiophene-2-carboxamidine hydrochloride (5.8 mg, 29% E/Z=1:1) as a clear film: $^1$H NMR (CD$_3$OD) E-isomer δ 8.37 (1H,s), 7.92 (1H,d,J=8.2 Hz), 7.60 (1H,t,J=8.3 Hz), 7.39 (1H,d,J=7.3 Hz), 4.95 (4H,br s), 2.37 (2H,q,J=7.5 Hz), 1.84 (3H,m), 1.26 (3H,t,J=7.4 Hz); Z-isomer δ 8.37 (1H,s), 7.92 (1H,d,J=8.2 Hz), 7.60 (1H,t,J=8.3 Hz), 7.36 (1H,d,J=8.0 Hz), 4.95 (4H,br s), 2.22 (2H,q,J=7.9 Hz), 2.05 (3H,s), 1.10 (3H,t,J=7.0 Hz).

Compound 23

4-(E-3-Methylbut-1-enyl)benzo[b]thiophene-2-carboxamidine hydrochloride 4-(E/Z-3-Methylbut-1-enyl)benzo[b]thiophene-2-carboxamidine. HCl (Compound 22) was purified by hplc on a C18 reverse phase column eluting isocratically with 25% acetonitrile/water containing 0.15% TFA. The E-isomer eluted more slowly, and the Z-isomer was largely converted into the E-isomer by the chromatography. For spectrum, see Compound 22.

Compound 24

4-(3-Methylbut-2-enyl)benzo[b]thiophene-2-carboxamidine hydrochloride

Dry DMF (0.5 mL) was added to a mixture of methyl 4-(trimethylstannyl)benzo[b]thiophene-2-carboxylate (88.3 mg, 0.25 mmol, see Compound 67), 3-methylbut-2-en-1-yl acetate (48.9 mg, 0.38 mmol) palladium (dba)$_2$, (8.6 mg, 0.015 mmol) and LiCl (57.1 mg, 1.33 mmol), and stirred under N$_2$ at 25° C. There was an immediate mild exotherm, and an initial reddish-brown coloration, which soon faded to a green-grey slurry. After 3.5 h the reaction mixture was purified directly by preparative tlc (10% EtOAc/hexanes) to give after ether extraction of the major band and evaporation of the solvent under reduced pressure, 4-(3-methylbut-2-enyl)benzo[b]thiophene-2-carboxylate (19.9 mg, 31%) containing a 12% unidentified byproduct. This ester was amidinated with 12 equivalents of NH$_4$Cl/Me$_3$Al in refluxing toluene to give, after the usual workup and purification by flash chromatography (10%, then 20% CH$_3$OH/CH$_2$Cl$_2$), 4-(3-Methylbut-2-enyl)benzo[b]thiophene-2-carboxamidine hydrochloride monohydrate (5.6 mg, 26%) as an orange brown glass: $^1$H NMR (CD$_3$OD) δ 8.41 (1H,s), 7.85 (1H,d,J=8.2 Hz), 7.50 (1H,t,J=7.7 Hz), 7.31 (1H,d,J=7.2 Hz), 5.40 (1H,br t,J=7.0 Hz), 4.91 (6H,br s), 3.75 (2H,d,J=6.8 Hz), 1.79, 1.76 (3H,3H,2s).

Compound 25

4-(E-Pent-1-enyl)benzo[b]thiophene-2-carboxamidine hydrochloride n-Butyltriphenylphosphonium bromide (131.0 mg, 0.33 mmol) was reacted with potassium tert-butoxide and methyl 4-formylbenzo[b]thiophene-2-carboxylate, as described in Compound 17, to afford, after preparative tlc (CHCl$_3$), methyl 4-(E/Z-pent-1-enyl)benzo[b]thiophene-2-carboxylate (32.9 mg, 55%) as a yellow syrup.

To a solution of this ester (32.9 mg, 0.13 mmol) in xylenes was added a solution of Me$_3$Al/NH$_4$Cl (0.5M, 1.3 mL) in xylenes. The mixture was heated under N$_2$ at 145° C. for 30 min then at 125° C. for 16 h to afford, after workup and column chromatography (15% MeOH/CHCl$_3$), 4-(E-pent-1-enyl)benzo[b]thiophene-2-carboxamidine hydrochloride (21.0 mg, 59%) as a light yellow solid: $^1$H NMR (CD$_3$OD) δ 8.60 (1H,s), 7.92 (1H,d,J=8.3 Hz), 7.69 (1H,d,J=7.4 Hz), 7.58 (1H,t,J=7.8 Hz), 7.03 (1H,d,J=15.5 Hz), 6.55 (1H,dt,J$_d$=15.8 Hz,J$_t$=8.0 Hz), 4.95 (4H,br s), 1.64 (2H, sextet,J=7.5 Hz), 1.06 (3H,t,J=7.4 Hz).

Compound 26

4-(E-4-Methylpent-1-enyl)benzo[b]thiophene-2-carboxamidine hydrochloride iso-Amyltriphenylphosphonium bromide (131.0 mg, 0.33 mmol) was reacted with potassium tert-butoxide and methyl 4-formylbenzo[b]thiophene-2-carboxylate, as described in Compound 17, to afford, after preparative tlc (CHCl$_3$), methyl 4-(E/Z-4-methylpent-1-enyl)-benzo[b]thiophene-2-carboxylate (32.7 mg, 51%) as a yellow syrup.

To a solution of this ester (32.7 mg, 0.12 mmol) in xylenes was added a solution of Me$_3$Al/NH$_4$Cl (0.5M, 1.2 mL) in xylenes. The mixture was heated under N$_2$ for at 145° C. for 35 min then at 125° C. for 17 h to afford, after workup and column chromatography (15% MeOH/CHCl₃), 4-(E-4-methylpent-1-enyl)benzo[b]thiophene-2-carboxamidine hydrochloride (20.3 mg, 58%) as a light yellow solid: ¹H NMR (CD₃OD) δ 8.60 (1H,s), 7.92 (1H,d,J=8.2 Hz), 7.70 (1H,d,J=7.4 Hz), 7.59 (1H,t,J=8.0 Hz), 7.03 (1H,d,J=15.5 Hz), 6.55 (1H,dt,$J_d$=15.6 Hz,$J_t$=7.7 Hz), 4.95 (4H,br s), 2.41 (2H,q,J=7.0 Hz), 1.87 (1H,m), 1.05 (6H,d,J=6.7 Hz).

Compound 27

4-([R/S]-E-4-Methylpent-1-enyl)benzo[b]thiophene-2-carboxamidine hydrochloride

To a solution of methyl 4-formylbenzo[b]thiophene-2-carboxylate (0.60 g, 2.7 mmol, Compound 22) stirred under N₂ in THF at 0° C. was added a solution of BH₃.THF (1M, 2.7 mL, 2.7 mmol) in THF. After 10 min the reaction was quenched with excess MeOH, poured onto a saturated aqueous NaHCO₃ solution, and extracted into Et₂O. The organic layer was dried (MgSO₄), filtered, and evaporated to dryness to afford 4-hydroxymethylbenzo[b]thiophene-2-carboxylate (0.60 g, 99%) as a white solid.

To a mixture of triphenylphosphine (0.79 g, 3.0 mmol) and carbon tetrabromide (0.98 g, 3.0 mmol) in THF (15 mL), stirred under N₂ at 25° C., was added a solution of methyl 4-hydroxymethylbenzo[b]thiophene-2-carboxylate (0.60 g, 2.7 mmol) via cannula and the mixture was allowed to stir for 16.5 h. Addition of Et₂O, followed by filtration of solids and concentration of the filtrate under reduced pressure, yielded a yellow syrup, which after flash chromatography (CHCl₃) afforded methyl 4-bromomethylbenzo[b]thiophene-2-carboxylate (675.1 mg, 88%) as a pale beige solid.

A solution of this bromide (675.1 mg, 2.4 mmol) and triphenylphosphine (745.1 mg, 2.8 mmol) in toluene (8 mL) was stirred under N₂ at 80° C. for 15 h, cooled to 25° C., and the precipitate was filtered, washed with hexanes, and air dried to afford (2-carboxymethylbenzo[b]thien-4-yl)methyltriphenylphosphonium bromide (1.276 g, 98%) as a white solid.

To a suspension of this phosphonium salt (301.1 mg, 0.6 mmol) in THF (5 mL) stirred under N₂ at 0° C. was added potassium tert-butoxide (0.54M, 970 μL). After 20 min the reaction was cooled to −78° C. and neat 2-methylbutanal (43.1 mg, 54 μL, 0.5 mmol) was added. There was no reaction at −78° C. nor at 25° C. so the reaction was heated to 50° C. for 1 h, cooled to 25° C. and then poured onto saturated aqueous NaHCO₃ solution, and extracted into Et₂O. The organic layer was washed with water and saturated brine, dried (MgSO₄), filtered, and evaporated to dryness under reduced pressure to afford, after column chromatography (5% EtOAc/hexanes), methyl 4-([R/S]-E/Z-3-methylpent-1-enyl)benzo[b]thiophene-2-carboxylate (79.0 mg, 58%) as a clear, colorless syrup.

To a solution of the above ester (79.0 mg, 0.28 mmol) in xylenes (3 mL) was added Me₃Al/NH₄Cl solution (0.5M, 2.9 mL) and the mixture was heated under N₂ to 145° C. for 2.5 h to afford, after workup and column chromatography (15%MeOH/CHCl₃), 4-([R,S]-E-3-methylpent-1-enyl)benzo[b]thiophene-2-carboxamidine hydrochloride (81.8 mg, 96%) as a yellow solid: ¹H NMR (CD₃OD) δ 8.61 (1H,s), 7.92 (1H,d,J=8.0 Hz), 7.70 (1H,d,J=7.2 Hz), 7.59 (1H,t,J=7.5 Hz), 7.01 (1H,d,J=15.9 Hz), 6.43 (1H,dd,J=16.0,8.0 Hz), 5.00 (4H,br s), 2.40 (1H,m), 1.56 (2H,m), 1.21 (3H,d,J=6.8 Hz), 1.02 (3H,t,J=7.3 Hz).

Compound 28

4-(E-3-ethylpent-1-enyl)benzo[b]thiophene-2-carboxamidine hydrochloride

To a suspension of (2-carboxymethylbenzo[b]thien-4-yl)methyltriphenylphosphonium bromide (360.7 mg, 0.66 mmol, Compound 27) in THF (8 mL) stirred under N₂ at 0° C. was added potassium tert-butoxide (0.54M, 1.2 mL). After 20 min the reaction was cooled to −78° C. and a solution of 2-ethylbutanal (60.0 mg, 0.60 mmol) in THF was added via cannula. There was no reaction at −78° C. nor at 25° C. so the reaction was heated to reflux for 15 h, and then poured onto saturated aqueous NaHCO₃ solution, and extracted with Et₂O. The organic layer was washed with water and saturated brine, dried (MgSO₄), filtered, and evaporated to dryness afford, after column chromatography on silica gel (5% EtOAc/hexanes), methyl 4-(E/Z-3-methylpent-1-enyl)-benzo[b]thiophene-2-carboxylate (11.7 mg, 7%) as a light oil.

To a solution of the above ester (11.7 mg, 0.04 mmol) in xylenes (2 mL) was added Me₃Al/NH₄Cl solution (0.5M, 810 μL) and the mixture was refluxed under N₂ for 2.5 h then heated at 125° C. for 16 h to afford, after workup and column chromatography (15%MeOH/CHCl₃), 4-(E-3-ethylpent-1-enyl)benzo[b]thiophene-2-carboxamidine hydrochloride (6.2 mg, 49%) as a light yellow solid,: ¹H NMR (CD₃OD) δ 8.59 (1H,s), 7.92 (1H,d,J=8.3 Hz), 7.72 (1H,d,J=7.5 Hz), 7.59 (1H,d,J=7.6 Hz), 7.01 (1H,d,J=15.5 Hz), 6.28 (1H,dd,J=15.8, 9.0 Hz), 4.96 (4H,br s), 2.15 (1H,m), 1.65 (2H,m), 1.50 (2H,m), 1.00 (6H,t,J=7.4 Hz).

Compound 29

4-(E/Z-Hex-1-enyl)benzo[b]thiophene-2-carboxamidine hydrochloride n-Pentyltriphenylphosphonium iodide (131.0 mg, 0.33 mmol) was reacted with potassium tert-butoxide and methyl 4-formylbenzo[b]thiophene-2-carboxylate, as described in Compound 17, and purified by preparative tlc (1% CH₃OH/CHCl₃) to afford methyl 4-(E/Z-hex-1-enyl)benzo[b]thiophene-2-carboxylate (40.3 mg, 53%) as a yellow syrup.

To a solution of this ester (40.3 mg, 0.15 mmol) in xylenes (1.5 mL) was added a solution of Me₃Al/NH₄Cl (0.5M, 730 μL) in xylenes. The mixture was heated under N₂ to 135° C. for 1 h to afford, after workup and flash chromatography (15% CH₃OH/CHCl₃) 4-(E/Z-hex-1-enyl)benzo[b]thiophene-2-carboxamidine hydrochloride (40.5 mg, 93%, initialE/Z=1:1, >80% E on standing) as a yellow solid: ¹H NMR (CD₃OD) E-isomer only δ 8.60 (1H,s), 7.92 (1H,d,J=8.0 Hz), 7.69 (1H,d,J=7.5 Hz), 7.58 (1H,t,J=7.9 Hz), 7.03 (1H,d,J=15.7 Hz), 6.56 (1H,dt,$J_d$=15.7 Hz, $J_t$=7.2 Hz), 4.96 (4H,br s), 1.59 (2H,m), 1.49 (2H,m), 1.02 (3H,d,J=7.3 Hz).

Compound 30

4-(E-Oct-1-enyl)benzo[b]thiophene-2-carboxamidine hydrochloride n-Heptyltriphenylphosphonium bromide (131.0 mg, 0.33 mmol) was reacted with potassium tert-butoxide and methyl 4-formylbenzo[b]thiophene-2-carboxylate, as described in Compound 17, and purified by preparative tlc (CHCl₃) to afford methyl 4-(E/Z-oct-1-enyl)- benzo[b]thiophene-2-carboxylate (24.6 mg. 28%) as a yellow syrup.

To a solution of this ester (35.1 mg, 0.12 mmol) in xylenes (3 mL) was added a solution of Me$_3$Al/NH$_4$Cl (0.5M, 1.2 mL) in xylenes. The mixture was heated under N$_2$ to 145° C. for 6.25 h after which time the reaction was incomplete. More Me3Al/NH4Cl (0.6 mL) was added and the temperature was reduced to 114° C. for 17.5 h to afford, after workup and flash chromatography (15% CH$_3$OH/CHCl$_3$), 4-(E-oct-1-enyl)benzo[b]thiophene-2-carboxamidine hydrochloride (18.5 mg, 49%) as an orange solid: $^1$H NMR (CD$_3$OD) δ 8.60 (1H,s), 7.92 (1H,d,J=7.8 Hz), 7.69 (1H,d,J=6.8 Hz), 7.58 (1H,t,J=7.5 Hz), 7.03 (1H,d, J=14.4 Hz), 6.58 (1H,m), 4.95 (4H,br s), 2.39 2H,m), 1.61 (2H,m), 1.55–1.27 (6H,m), 0.96 (3H,m).

Compound 31

4-(E-Dec-1-enyl)benzo[b]thiophene-2-carboxamidine hydrochloride n-Nonyltriphenylphosphonium bromide (131.0mg, 0.33 mmol) was reacted with potassium tert-butoxide and methyl 4-formylbenzo[b]thiophene-2-carboxylate, as described in Compound 17, and purified by preparative thin layer chromatography (CHCl$_3$) to afford methyl 4-(E/Z-dec-1-enyl)benzo[b]thiophene-2-carboxylate (24.6 mg. 28%) as a yellow syrup.

To a solution of this ester (24.6 mg, 0.07 mmol) in xylenes (3 mL) was added a solution of Me$_3$Al/NH$_4$Cl (0.5M, 750 μL) in xylenes. The mixture was heated under N$_2$ to 145° C. for 6.25 h to afford, after workup and flash chromatography (20% CH$_3$OH/CHCl$_3$), 4-(E-dec-1-enyl)benzo[b]thiophene-2-carboxamidine hydrochloride (8.6 mg, 33%) as an orange solid: $^1$H NMR (CD$_3$OD) δ 8.60 (1H,s), 7.92 (1H,d,J=7.8 Hz), 7.69 (1H,d,J=7.0 Hz), 7.58 (1H,t,J=8.0 Hz), 7.03 (1H,d,J=16.3 Hz), 6.55 (1H,dd, J=15.4,7.5 Hz), 4.95 (4H,br s), 2.40 (2H,m), 1.61 (2H,m), 1.36 (8H,m), 0.94 (3H,m).

Compound 32

4-(E-5-Hydroxypent-1-enyl)benzo[b]thiophene-2-carboxamidine hydrochloride

Pent-4-yn-1-ol (10.7 mmol) was converted to the corresponding tert-butyldimethylsilyl ether (1.05 equiv t-butyldimethylsilylchloride, 1.13 equiv imidazole, CH$_2$Cl$_2$, 0° C. to room temp) in 99% yield. This alkyne (2.02 mmol) was treated with catecholborane (1.07 equiv, neat, 70° C., 1 hr) to afford the corresponding E-5-(t-butyldimethylsilyloxy)pent-1-enylboronic ester which was used without purification. A mixture of this alkenylboronic ester (365.5 mg, 1.14 mmol), 4-iodobenzo[b]thiophene-2-carbonitrile (243.7 mg, 0.85 mmol, Compound 42), and bis(triphenylphosphine)palladium-(II) chloride (33.3 mg, 0.04 mmol) in benzene (6 mL) and 2M aq. NaOH (0.5 mL) was heated at reflux for 8.6 h. The mixture was cooled to 25° C., tetra-n-butylammonium fluoride (TFBA; 2 mL, 1M in THF) was added, and the mixture was stirred for 14 h. The reaction mixture was diluted with EtOAc, washed with water, 10% aqueous HCl, saturated brine, and dried (MgSO$_4$). After filtration and solvent removal, $^1$H NMR analysis of the residue showed that the silyl ether was still intact. The crude residue was dissolved in THF (5 mL) and TBAF (2 mL) was added. After stirring at room temperature for 2.75 h the mixture was worked up as above, and the residue purified by flash chromatography (40% EtOAc/hexane) to afford 4-(E-5-hydroxy-pent-1-enyl)benzo[b]thiophene-2-carbonitrile (104.1 mg, 50%) as a viscous oil.

This material (104.1 mg, 0.43 mmol) was dissolved in Et$_2$O (5 mL) under N$_2$ at 25° C., and lithium hexamethyldisilazide (LiHMDS; 1.3 mL, 1.0M in hexane, 1.43 mmol) was added, with the immediate formation of a white precipitate, which slowly disslolved up. After 3 h, 10% aqueous HCl (5 mL) was added and the biphasic mixture was stirred for an additional 3 h. The layers were separated, and the aqueous phase was evaporated. The residue was purified by flash chromatography (15% MeOH/CHCl$_3$) to afford 4-(E-5-hydroxypent-1-enyl)benzo[b]thiophene-2-carboxamidine hydrochloride (105.9 mg, ca. 83%, ≧90% pure) as an offwhite solid: $^1$H NMR (CD$_3$OD) δ 8.59 (1H,s), 7.87 (1H,d,J=8.1 Hz), 7.63 (1H,d,J=7.4 Hz), 7.53 (1H,t,J=7.7 Hz), 7.01 (1H,br d,J=15.7 Hz), 6.51 (1H,dt,J$_d$=15.7 Hz,J$_t$=6.8 Hz), 4.92 (5H,br s), 3.65 (2H,t,J=6.4 Hz), 2.42 (2H,q,J=7.2 Hz), 1.78 (2H,pent,J=6.7 Hz).

Compound 33

4-(7-Amidino-E-hept-1-enyl)benzo[b]thiophene-2-carboxamidine bishydrochloride

Hex-5-yn-1-ol (16.1 mmol) was converted to the corresponding mesylate (2.0 equiv mesyl chloride, 3.0 equiv NEt$_3$, CH$_2$Cl$_2$, 0° C.), and the crude material, after aqueous workup, was treated with NaI (1.42 g, 9.47 mmol) and LiCN (38 mL, 0.5 M in DMF). The homogeneous mixture was heated at 80° C. for 20 h, cooled to 25° C., diluted with EtOAc, washed with water (5×), brine, and dried (MgSO$_4$). After filtration and solvent removal, the residue was purified by bulb-to-bulb distillation (ca. 0.75 mm Hg, ca. 70° C.) to afford hept-6-ynenitrile (812.1 mg, 84%) as a clear, colorless oil. A mixture of the alkyne (1.89 mmol), tri-n-butyltin hydride (2.08 mmol), and AIBN (ca. 5 mg) in toluene (4 mL) was heated at 90° C. for 4 h. After cooling to 25° C. and solvent removal, the residue was purified by flash chromatography (4% EtOAc/hexane) to provide 7-(tri-n-butylstannyl)-6-heptenenitrile (682.9 mg, 91%, E/Z ratio not determined) as a clear, colorless oil.

A mixture of these alkenylstannanes (295.0 mg 0.74 mmol), methyl 4-iodobenzo[b]thiophene-2-carboxylate (214.6 mg, 0.67 mmol, Compound 5), bis(triphenylphosphine)palladium(II) chloride (21.1 mg, 0.03 mmol), and LiCl (93.2 mg, 2.19 mmol) in DMF (5 mL) was heated at 80° C. for 2 h. Workup and flash chromatography (30% EtOAc/hexane) gave methyl 4-(E/Z-6-cyanohex-1-enyl)benzo[b]thiophene-2-carboxylate 169.4 mg, 84%, E/Z=5 as determined by $^1$H NMR integration). Treatment of this ester (169.4 mg, 0.56 mmol) with 8.1 equiv of Me$_3$Al/NH$_4$Cl (xylene, 130° C., 23 h) provided, after workup and chromatography (25% MeOH/CHCl$_3$), 4-(E/Z-7-amidino-hept-1-enyl)benzo[b]thiophene-2-carboxamidine bis-hydrochloride (223.6 mg, quant., E/Z=9) as a fluffy, light yellow solid: $^1$H NMR (CD$_3$OD) E-isomer δ 8.37 (1H,s), 7.94 (1H,d,J=8.0 Hz), 7.88 (1H,d,J=8.0 Hz), 7.64 (1H,t,J=7.4 Hz), 7.05 (1H,br d,J=15.8 Hz), 6.51 (1H,dt,J$_d$=15.8 Hz,J$_t$=6.9 Hz), 4.90 (8H,br s), 2.52 (2H,t,J=7.6 Hz), 2.42 (2H,q,J=7.2 Hz), 1.81 (2H,pent,J=7.8 Hz), 1.67 (2H,pent,J=8.4 Hz).

Compound 34

4-(E/Z-2-Cyclopropylethenyl)benzo[b]thiophene-2-carboxamidine. hydrochloride Cyclopropylmethyltriphenylphosphonium bromide (131.0 mg, 0.33 mmol) was reacted with potassium tert-butoxide and methyl 4-formylbenzo[b]thiophene-2-carboxylate, as described in Compound 17, and purified by preparative tlc (3% EtOAc/hexanes) to afford methyl 4-(E/Z-2-cyclopropylethenyl)benzo[b]thiophene-2-carboxylate (24.6 mg. 28%) as a yellow syrup.

To a solution of this ester (42.6 mg, 0.16 mmol) in xylenes (2 mL) was added a solution of $Me_3Al/NH_4Cl$ (0.5M, 1.23 mL) in xylenes. The mixture was heated under $N_2$ to 140° C. for 4 h to afford, after workup and flash chromatography (15% $CH_3OH/CHCl_3$) 4-(E/Z-2-cyclopropylethenyl)benzo[b]thiophene-2-carboxamidine hydrochloride (39.9 mg, 87%, E/Z=1:2) as an orange solid: $^1H$ NMR ($CD_3OD$) E-isomer δ 8.62 (1H,s), 7.88 (1H,d,J=8.0 Hz), 7.64 (1H,t,J=7.0 Hz), 7.56 (1H,d,J=7.9 Hz), 7.10 (1H,d,J=15.7 Hz), 6.07 (1H,dd,J=16.0, 8.0 Hz), 4.96 (4H,br s), 1.76 (1H,m), 0.95 (2H,m), 0.67 (2H,m); Z-isomer δ 8.46 (1H,s), 7.91 (1H,d,J=8.0 Hz), 7.68 (1H,t,J=8.0 Hz), 7.63 (1H,t,J=8.0 Hz), 5.42 (1H,t,J=11 Hz), 4.96 (4H,br s), 1.76 (1H,m), 0.89 (2H,m), 0.59 (2H,m).

Compound 35

4-(E-2-Cyclohexylethenyl)benzo[b]thiophene-2-carboxamidine hydrochloride

A mixture of cyclohexylacetylene (7.65 mmol) and catecholborane (7.69 mmol) was heated at 70° C. for 4.5 h. After cooling to room temperature, the E-2-cyclohexylethenylboronic ester was used without purification. A mixture of this boronic ester (278.1 mg, 1.22 mmol), methyl 4-iodobenzo[b]thiophene-2-carboxylate (250.5 mg, 0.78 mmol, Compound 5), and bis(triphenylphosphine)palladium(II) chloride (17.1 mg, 0.02 mmol) in benzene (5 mL) and 2M aq. NaOH (0.5 mL) was heated at reflux for 16 h. Aqueous workup and chromatographic purification (7% EtOAc/hexane) afforded methyl 4-(E-2-cyclohexylethenyl)benzo[b]thiophene-2-carboxylate (145.2 mg, 61%). Treatment of this ester (145.2 mg, 0.48 mmol) with 5.0 equiv $Me_3Al/NH_4Cl$ (xylene, 130° C., 5 h) gave, after workup and chromatographic purification (15% $MeOH/CHCl_3$), 4-(E-2-cyclohexylethenyl)benzo[b]thiophene-2-carboxamidine hydrochloride (112.1 mg, 72%) as an offwhite solid: $^1H$ NMR ($CD_3OD$) δ 8.56 (1H,s), 7.86 (1H,d J=8.2 Hz), 7.63 (1H,d,J=7.4 Hz), 7.53 (1H,t, J=7.8 Hz), 6.94 (1H,br d,J=15.8 Hz), 6.44 (1H,dd, J=15.8,7.1 Hz), 4.86 (4H,brs), 2.28–2.26 (1H,m), 1.89 (2H,brd,J=12.0 Hz), 1.82 (2H,brd,J=12.6 Hz), 1.73 (1H,brd,J=12.6 Hz), 1.44–1.24 (5H,m).

Compound 36

4-(E-3-Phenylprop-2-enyl)benzo[b]thiophene-2-carboxamidine hydrochloride n-BuLi (1.1 mL, 2.5M in hexane) was added dropwise to a 0° C. solution of hexamethylditin (987.7 mg, 3.01 mmol) in THF (5 mL). After 20 min the reaction was cooled to −78° C. and $Et_2AlCl$ (1.5 mL, 1.8M in hexane) was added. After stirring 60 min, a solution of tetrakis(triphenylphosphine)palladium (100.3 mg, 0.08 mmol) in THF (2 mL) was added via cannula followed by a solution of cinnamyl acetate (0.3 mL, 1.79 mmol) in THF (2 mL). After 1 h, the cold-bath was removed and the reaction mixture was allowed to warm to 25° C. The mixture was cooled to 0° C. and quenched with aq. $NH_4OH$, diluted with $Et_2O$, washed with water (2x), brine, and dried ($MgSO_4$). After filtration and solvent removal, the residue was purified by flash chromatography (1% $Et_3N$/hexane) to give cinnamyl(trimethyl)stannane (263.8 mg, 52%) as a clear, colorless oil.

A solution of this stannane (263.8 mg, 0.94 mmol), methyl 4-iodobenzo[b]thiophene-2-carboxylate (272.0 mg, 0.85 mmol, Compound 5), bis(triphenylphosphine)palladium(II) chloride (34.3 mg, 0.05 mmol), and LiCl (114.6 mg, 2.70 mmol) in DMF (6 mL) was heated at 90° C. for 2 h. An additional 15 mg of catalyst was added, and the reaction was heated for 1 h. Workup and chromatographic purification (8% EtOAc/hexane) provided 153.4 mg of impure product. A second flash column (4% EtOAc/hexane) gave 64.0 mg of less impure product, and recrystallization of this material from hexane afforded pure methyl 4-(E-3-phenylprop-2-enyl)-benzo[b]thiophene-2-carboxylate (43.6 mg, 16%) as white crystals. Treatment of this ester (0.14 mmol) with 5.1 equiv $Me_3Al/NH_4Cl$ (xylene, 130° C., 4.5 h) gave, after workup and chromatographic purification (15% $MeOH/CHCl_3$), 4-(E-3-phenylprop-2-enyl)benzo[b]thiophene-2-carboxamidine hydrochloride (32.8 mg, 71%) as a white solid: $^1H$ NMR ($CD_3OD$)δ 8.51 (1H,s), 7.88 (1H,d,J=8.2 Hz), 7.52 (1H,t,J=7.8 Hz), 7.38 (1H,d,J=7.3 Hz), 7.32 (2H,d,J=7.4 Hz), 7.24 (2H,t,J=7.5 Hz), 7.15 (1H,t,J=7.3 Hz), 6.50–6.40 (2H,m), 4.98 (4H,br s), 3.93 (2H, d,J=4.8 Hz).

Compound 37

4-(E-5-Phenylpent-1-enyl)benzo[b]thiophene-2-carboxamidine hydrochloride.

To a suspension of pyridinium chlorochromate (35.72 mmol) and Celite (7 g) in $CH_2Cl_2$ (50 mL) was added a solution of 4-phenylbutan-1-ol (32.45 mmol) in $CH_2Cl_2$ (10 mL). After 1.5 h, $Et_2O$ (100 mL) was added and the mixture stirred for 1 h. After filtration through a plug of Celite and solvent evaporation, the residue was purified by bulb-to-bulb distillation to afford 4-phenylbutan-1-al (3.25 g, 68%) as a clear, colorless liquid. A solution of triphenylphosphine (28.58 mmol) in $CH_2Cl_2$ (15 mL) was added via cannula to a 0° C. solution of $CBr_4$ (14.59 mmol) in $CH_2Cl_2$ (10 mL). After stirring for 5 min, a solution of 4-phenylbutanal (7.16 mmol) in $CH_2Cl_2$ (5 mL) was added dropwise via cannula. After stirring 35 min, the reaction mixture was transfered to an Erlenmeyer flask with $CHCl_3$ and hexane (50 mL) was added. The heterogeneous mixture was stirred for several min, and filtered. The solids were rinsed with hexane, and the combined organics were evaporated. Hexane (100 mL) was added to the residue with stirring. Filtration, evaporation, a third precipitation with hexane, followed by filtration and evaporation gave a clear, colorless liquid which was dissolved in THF (50 mL) and cooled to −78° C. n-BuLi (6.2 mL, 2.5M in hexanes, 15.5 mmol) was added dropwise by syringe and the dark mixture was stirred for 1 h. The reaction was warmed to 0° C. for 1 h. The reaction was quenched by the addition of water, and extraction with $Et_2O$. The organic phase was washed with water (3×), brine, and dried ($MgSO_4$). After filtration and solvent removal, the residue was purified by bulb-to-bulb distillation (ca. 1.5 mm Hg, ca. 100° C.) to provide 5-phenylpent-1-yne (791.2 mg, 77%) as a clear, colorless liquid.

A mixture of 5-phenylpent-1-yne (2.01 mmol) and catecholborane (2.11 mmol) was heated at 75° C. under N$_2$ for 1.25 h. A solution of this boronic ester (530 mg, 2.00 mmol), methyl 4-iodobenzo[b]thiophene-2-carboxylate (325.4 mg, 1.02 mmol, Compound 5), and bis(-triphenylphosphine)palladium(II) chloride (15.4 mg, 0.02 mmol) in benzene (6 mL) and 2M aq NaOH (1 mL) was heated at reflux under N$_2$ for 18.5 h. The reaction mixture was cooled to 25° C., diluted with EtOAc, washed with water, saturated aqueous NaHCO$_3$ solution, water, saturated brine, and dried (MgSO$_4$). After filtration and solvent removal, the residue was purified by flash chromatography (5% EtOAc/hexane) to provide 305.2 mg of impure methyl 4-(E-5-phenylpent-1-enyl)benzo[b]thiophene-2-carboxylate. A second column (3% EtOAc/hexane) afforded 105.7 mg of less impure material, which was treated with 5.1 equiv of Me$_3$Al/NH$_4$Cl (xylene, 130° C., 4 h) to give, after workup and purification by flash chromatography (15% MeOH/CHCl$_3$), 4-(E-5-phenylpent-1-enyl)benzo[b]thiophene-2-carboxamidine hydrochloride (49.2 mg, ca. 80% pure). Recrystallization of this material from EtOH increased the purity to ca. 90% (20.0 mg): $^1$H NMR (CD$_3$OD) δ 8.54 (1H,s), 7.86 (1H,d,J =8.0 Hz), 7.62 (1H,d,J=7.5 Hz), 7.52 (1H,t,J=7.8 Hz), 7.26 (2H,t,J=7.3 Hz), 7.20 (2H,d,J=6.9 Hz), 7.14 (1H,t,J=7.3 Hz), 6.97 (1H,d,J=15.7 Hz), 6.50 (1H,dt,J$_d$=15.7 Hz, J$_t$=7.0 Hz), 4.90 (4H,br s), 2.70 (2H,t,J=7.6 Hz), 2.36 (2H,q,J=6.9 Hz), 1.86 (2H,pent,J=7.6 Hz).

Compound 38

4-(2,2-Dibromoethenyl)benzo[b]thiophene-2-carboxamidine hydrochloride

To a mixture of triphenylphosphine (378.2 mg, 1.4 mmol) and carbon tetrabromide (239.1 mg, 0.72 mmol) in CH$_2$Cl$_2$ (8 mL) stirred under N$_2$ at 0° C. was added solid methyl 4-formylbenzo[b]thiophene-2-carboxylate (79.4 mg, 0.36 mmol, Compound 22). The reaction was stirred for 10 min, diluted with hexanes, and filtered through a silica gel plug with 20% EtOAc/hexanes to yield, after solvent removal, methyl 4-(2,2-dibromoethenyl)benzo[b]thiophene-2-carboxylate (127.1 mg, 94%) as a white solid.

To this ester (127.1 mg, 0.34 mmol) was added a Me$_3$Al/NH$_4$Cl solution (0.25M, 6.9 mL) in xylenes and the mixture was heated under to 110° C. for 2.5 h and at 130° C. for 2 h to afford, after workup and column chromatography (15% MeOH/CHCl$_3$), 4-(2,2-dibromoethenyl)benzo[b]thiophene-2-carboxamidine hydrochloride trihydrate (82.1 mg, 54%) as a beige solid: $^1$H NMR (DMSO-d$_6$) δ 9.50 (2H,br s), 9.22 (2H, br s), 8.51 (1H,s), 8.24 (1H,d,J=7.9 Hz), 8.16 (1H,s), 7.73 (1H,d,J=7.4 Hz), 7.66 (1H,t,J=7.9 Hz).

Compound 39

4-Ethynylbenzo[b]thiophene-2-carboxamidine hydrochloride

Potassium t-butoxide (0.37M in THF, 1.35 mL, 0.50 mmol) was added dropwise over 2 min to a solution of di-O-methyldiazomethylphosphonate (DAMP) (75.3 mg, 0.50 mmol) in THF (2 mL), stirred under Ar at −78° C. After 5 minutes methyl 4-formylbenzo[b]thiophene-2-carboxylate (110.3 mg, 0.50 mmol, Compound 22) in THF (2 mL) was added dropwise over 2 min. After 14 h at −78° C. the reaction mixture was stirred at 25° C. for 20 min, and worked up by pouring onto saturated NaHCO$_3$ solution (10 mL), and extracting with CH$_2$Cl$_2$ (3×10 mL). The combined extracts were washed with water (2×10 mL), saturated brine (10 mL), and dried (MgSO$_4$). The solvent was removed under reduced pressure, and the residual oil was purified by preparative tlc, eluting with 10% EtOAc in hexanes. The major band was extracted with ether and evaporated to dryness to give methyl 4-ethynylbenzo[b]thiophene-2-carboxylate (54.9 mg, 51%) as a white crystalline solid. This material was amidinated in the usual fashion to give 4-ethynylbenzo[b]thiophene-2-carboxamidine hydrochloride (42.7 mg, 72%) as a light yellow-brown solid: $^1$H NMR (DMSO-d$_6$) δ 9.50 (4H,br s), 8.50 (1H,s), 8.27 (1H,d,J=8.2 Hz), 7.69 (1H,d,J=6.7 Hz), 7.60 (1H,t,J=7.4 Hz). 4.81 (1H,s).

Compound 40

4-(3-Methylbut-1-ynyl)benzo[b]thiophene-2-carboxamidine hydrochloride

A solution of methyl 4-iodobenzo[b]thiophene-2-carboxylate (105.2 mg, 0.33 mmol, Compound 5), 3-methylbutyne (60 μl), bis(triphenylphosphine)palladium(II) chloride (6.8 mg, 0.009 mmol), and CuI (2.0 mg, 0.01 mmol) in Et$_3$N (1 mL) was stirred at room temperature for 20.6 h. The reaction mixture was diluted with EtOAc, washed with 10% aqueous HCl, water (2×), brine, and dried (MgSO$_4$). After filtration and solvent removal, the residue was purified by flash chromatography (7% EtOAc/hexane) to afford methyl 4-(3-methylbutynyl)benzo[b]thiophene-2-carboxylate (64.9 mg, 76%) as a yellow solid. Treatment of this ester (0.25 mmol) with 4.0 equiv Me$_3$Al/NH$_4$Cl (toluene, 110° C., 27 h) followed by addition of 4 equiv Me$_3$Al/NH$_4$Cl (17.5 h) gave, after workup and column chromatography (15% MeOH/CHCl$_3$), followed by preparative tlc (20% MeOH/CHCl$_3$), 4-(3-methylbutynyl)benzo[b]thiophene-2-carboxamidine hydrochloride (19.6 mg, 28%) as a yellow solid: $^1$H NMR (CD$_3$OD) δ 8.44 (1H,d,J=0.7 Hz), 8.00 (1H,ddd,J=4.9,4.2,0.7 Hz), 7.57 (1H,d,J=4.9 Hz), 7.56 (1H,d,J=4.2 Hz), 4.95 (4H,br s), 2.98 (1H,hept,J=6.9 Hz), 1.39 (6H,d,J=6.9 Hz).

Compound 41

4-(3,3-Dimethylbut-1-ynyl)benzo[b]thiophene-2-carboxamidine hydrochloride

A solution of methyl 4-iodobenzo[b]thiophene-2-carboxylate (203.0 mg, 0.64 mmol, Compound 5), 3,3-dimethylbutyne (0.32 mL, 2.59 mmol), bis(triphenylphosphine)palladium(II) chloride (10.1 mg, 0.01 mmol), and CuI (4.8 mg, 0.02 mmol) in Et$_3$N (2 mL) was stirred at room temperature for 15.6 h. Workup and purification by flash chromatography (7% EtOAc/hexane) afforded methyl 4-(3,3-dimethylbut-1-ynyl)benzo[b]thiophene-2-carboxylate (174.9 mg, 100%) as a light yellow solid. Treatment of this ester (0.64 mmol) with 5.0 equiv Me$_3$Al/NH$_4$Cl (xylene, 130° C., 4.5 h) gave, after workup and chromatographic purification (15% MeOH/CHCl$_3$), 4-(3,3-dimethylbut-1-ynyl)benzo[b]thiophene-2-carboxamidine hydrochloride (192.1 mg, 100%) as an offwhite solid: $^1$H NMR (DMSO-d$_6$) δ 9.75 (2H,br s), 9.46 (2H,br s), 8.37 (1H,s), 8.17 (1H,d,J=7.4 Hz), 7.55 (1H,t,J=7.4 Hz), 7.54 (1H,d,J=7.3 Hz), 1.39 (9H,s).

Compound 42

4-(3-Hydroxy-3-methylbut-1-ynyl)benzo[b]thiophene-2-carboxamidine hydrochloride Methyl 4-iodobenzo[b]thiophene-2-carboxylate (15.91 g, 50 mmol, Compound 5) in liquid ammonia (25 mL) was heated to 80° C. in a stainless steel bomb for 14 h. Evaporation of the volatiles gave 4-iodobenzo[b]thiophene-2-carboxamide (14.67 g, 97%) as a pale khaki solid.

$TiCl_4$ (2.0 mL, 22 mmol) in $CCl_4$ (5 mL) was added dropwise to THF (20 mL), stirred under $N_2$ at 0° C., forming a bright yellow slurry. 4-Iodobenzo[b]thiophene-2-carboxamide (3.03 g, 10 mmol) in THF (35 mL) was added dropwise over 20 min. After a further 1 h, $Et_3N$ (5.05 g, 50 mmol) was added dropwise. After a further 1 h at 0° C. and 3 h at 25° C., the dark brown slurry was poured onto ice-water (100 mL), and was extracted with EtOAc (75, 50 mL). The combined extracts were rinsed with saturated aqueous $NaHCO_3$ solution (50 mL), saturated brine (50 mL) and dried ($MgSO_4$). The solvent was removed under reduced pressure, and the residue was recrystallised from EtOAc at 0° C. to give 4-iodobenzo[b]thiophene-2-carbonitrile (1.88 g, 66%) as glistening bronze needles.

A slurry of 4-iodobenzothiophene-2-carbonitrile (142.4 mg, 0.5 mmol), 2-methylbut-3-yn-2-ol (48.9 mg, 0.58 mmol), CuI (1.9 mg, 0.01 mmol) and bis (triphenylphosphine)palladium dichloride (7.0 mg, 0.01 mmol) in $Et_3N$ (1.0 mL) was stirred under $N_2$ at 25° C. for 2 h. The volatiles were stripped under reduced pressure, and the residue was purified by preparative tlc, eluting with 30% EtOAc/hexanes. The major band was extracted with ether, and the solvent was removed under reduced pressure to give 4-(3-hydroxy-3-methylbut-1-ynyl)benzo[b]thiophene-2-carbonitrile (121.7 mg, 100%) as a light orange solid.

Lithium hexamethyldisilazide (1.0M in hexanes 0.40 mL, 0.4 mmol) was added dropwise to a solution of the nitrile (24.6 mg, 0.10 mmol) in ether (2 mL), and the mixture was stirred under $N_2$ at 25° C. There was an immediate precipitate, which dissolved up within 30 min. After 1 h, dilute hydrochloric acid (0.4M, 5 mL) was added, and the mixture was stirred vigorously for 1 h. Ether (5 mL) was added and the aqueous layer was removed, and stripped to dryness under reduced pressure. The residue was purified by flash chromatography eluting with 20% $MeOH/CHCl_3$. The compound was concentrated, and dried in vacuo over $P_2O_5$ to give 4-(3-hydroxy-3-methylbut-1-ynyl)benzo[b]thiophene-2-carboxamidine hydrochloride dihydrate (21.4 mg, 68%) as an off-white solid: $^1H$ NMR ($CD_3OD$) δ 8.44 (1H,s), 8.02 (1H,dd,J=2.0,6.9 Hz), 7.58 (1H,dd,J=7.2,2.0 Hz), 7.55 (1H,t,J=7.1 Hz), 4.90 (12H,br s), 1.65 (6H,s).

Compound 43

4-(Cyclohexylethynyl)benzo[b]thiophene-2-carboxamidine hydrochloride

A solution of methyl 4-iodobenzo[b]thiophene-2-carboxylate (250.6 mg, 0.79 mmol, Compound 5), phenylacetylene (115 μl, 0.88 mmol), bis(triphenylphosphine)-palladium(II) chloride (11.5 mg, 0.02 mmol), and CuI (6.4 mg, 0.03 mmol) in $Et_3N$ (2 mL) was stirred at 25° C. for 2 h. Workup and purification by flash chromatography (8% EtOAc/hexane) afforded 198.2 mg of a mixture of the product and starting iodide. This mixture was resubmitted to the reaction conditions (100 μl cyclohexylacetylene, 10 mg Pd(II), 6 mg CuI, 17 h). Workup and chromatographic purification provided pure methyl 4-(cyclohexylethynyl)benzo[b]thiophene-2-carboxylate (211.4 mg, 90%). Treatment of this ester (0.42 mmol) with 4.3 equiv $Me_3Al/NH_4Cl$ (xylene, 130° C., 4.5 h) gave, after workup and chromatographic purification (15% $MeOH/CHCl_3$), 4-(cyclohexylethynyl)benzo[b]thiophene-2-carboxamidine hydrochloride (37.3 mg, 28%) as a light yellow solid: $^1H$ NMR ($CD_3OD$) δ 8.43 (1H,s), 7.99 (1H,t,J=4.6 Hz), 7.55 (2H,d,J=4.4 Hz), 5.01 (4H,br s), 2.81–2.73 (1H,m), 2.11–1.97 (2H,m), 1.92–1.76 (2H,m), 1.72–1.55 (3H,m), 1.54–1.38 (3H,m).

Compound 44

4-Phenylbenzo[b]thiophene-2-carboxamidine hydrochloride

A solution of methyl 4-iodobenzo[b]thiophene-2-carboxylate (152.3 mg, 0.48 mmol, Compound 5), dimethyldiphenyltin (168.5 mg, 0.55 mmol), bis(triphenylphosphine)palladium(II) chloride (20.2 mg, 0.03 mmol), and LiCl (65.7 mg, 1.55 mmol) in DMF (4 mL) was heated at 80° C. for 6.5 h. Workup and chromatography (8% EtOAc/hexane) gave 117.0 mg of a mixture of the product and the starting iodide (ca. 86:14 as determined by $^1H$ NMR integration). This mixture was recrystallized from EtOH to afford methyl 4-phenylbenzo[b]thiophene-2-carboxylate (63.9 mg, 50%) as white crystals. Treatment of this ester (0.24 mmol) with 4.2 equiv $Me_3Al/NH_4Cl$ (toluene, 100° C., 14.5 h) gave, after workup and chromatographic purification (15% $MeOH/CHCl_3$), 4-phenylbenzo[b]thiophene-2-carboxamidine hydrochloride (50.0 mg, 73%) as a light yellow solid: $^1H$ NMR ($CD_3OD$) δ 8.35 (1H,s), 8.07 (1H,d,J=7.6 Hz), 7.70 (1H,t,J=6.8 Hz), 7.66–7.49 (6H,m), 4.94 (4H,br s).

Compound 45

4-(4-Methoxyphenyl)benzo[b]thiophene-2-carboxamidine hydrochloride

4-Methoxyphenyltrimethyltin was prepared in 88% yield by treatment of 4-bromoanisole (2.11 mmol) with t-butyl lithium (2.09 equiv, THF, −78° C., 15 min) followed by addition of chlorotrimethyltin (1.12 equiv, −78° C. to 0° C.) and aqueous workup. A solution of the stannane (254.3 mg, 0.94 mmol), methyl 4-iodobenzo[b]thiophene-2-carboxylate (199.5 mg, 0.63 mmol, Compound 5), bis(triphenylphosphine)palladium(II) chloride (22.2 mg, 0.03 mmol), and LiCl (83.3 mg, 1.96 mmol) in DMF (6 mL) was heated at 105° C. under $N_2$ with stirring for 4 h. Workup and chromatography (8% EtOAc/hexane) gave methyl 4-iodobenzo[b]thiophene-2-carboxylate (38.0 mg, 19%) along with methyl 4-(4-methoxyphenyl)benzo[b]thiophene-2-carboxylate (114.1 mg, 61% yield). Treatment of the latter ester (0.38 mmol) with 5.2 equiv $Me_3Al/NH_4Cl$ (toluene, 105° C., 23 hr) gave, after workup and chromatographic purification (15% $MeOH/CHCl_3$), 4-(4-methoxyphenyl)benzo[b]thiophene-2-carboxamidine hydrochloride (111.4 mg, 91%) as a light yellow solid: $^1H$ NMR ($CD_3OD$) δ 8.37 (1H,s), 8.01 (1H,d,J=8.1 Hz), 7.66 (1H,t,J=7.5 Hz), 7.55 (2H,d,J=8.1 Hz), 7.50 (1H,d,J=7.3 Hz), 7.13 (2H,d,J=8.1 Hz), 4.96 (4H,br s), 3.91 (3H,s).

Compound 46

4-(4-Nitrophenyl)benzo[b]thiophene-2-carboxamidine hydrochloride

4-Nitrophenol (11.32 mmol) was converted to the corresponding triflate (1.05 equiv trifluoromethanesulfonic anhydride, pyridine, 0° to 25° C.) in 83% recrystallized yield. Reaction of the aryl triflate (2.47 mmol) with hexamethylditin (2.81 mmol) and tetrakis(triphenylphosphine)palladium (0.15 mmol) in dioxane (90° C., 4 h) gave, after aqueous workup and recrystallization from EtOH, 4-nitrophenyltrimethyltin in ca. 20% yield. A solution of this stannane (178.2 mg, 0.62 mmol), methyl 4-iodobenzo[b]thiophene-2-carboxylate (176.6 mg, 0.55 mmol, Compound 5), bis(triphenylphosphine)palladium(II) chloride (26.8 mg, 0.04 mmol), and LiCl (83.6 mg, 1.97 mmol) in DMF (5 mL) was heated at 80° C. under $N_2$ with stirring for 3 h. Workup and chromatography (12% EtOAc/hexane) gave 68.0 mg of impure product. Recrystallization of this material from EtOH provided methyl 4-(4-nitrophenyl)benzo[b]thiophene-2-carboxylate (55.2 mg, ca. 80% pure, ca. 25% yield). Treatment of this ester (0.17 mmol) with 5.0 equiv $Me_3Al/NH_4Cl$ (xylene, 130° C., 5 h) gave, after workup and column chromatography (15% MeOH/CHCl$_3$), followed by preparative tlc (30% EtOAc/hexane) 4-(4-nitrophenyl)benzo[b]thiophene-2-carboxamidine hydrochloride (11.6 mg, ca. 80–85% pure) as a light yellow solid: $^1$H NMR (CD$_3$OD) δ 8.46 (2H,d,J=8.8 Hz), 8.35 (1H,s), 8.17 (1H,d,J=8.3 Hz), 7.91 (2H,d, J=8.8 Hz), 7.76 (1H,t,J=7.8 Hz), 7.66 (1H,t,J=7.3 Hz), 4.97 4H,br s).

Compound 47

4-(4-Carboxamidinophenyl)benzo[b]thiophene-2-carboxamidine bis-hydrochloride A solution of methyl 4-(trimethylstannyl)benzo[b]thiophene-2-carboxylate (100.1 mg, 0.28 mmol, Compound 67), 4-bromobenzonitrile (61.4 mg, 0.33 mmol), bis(triphenylphosphine)palladium (II) chloride (9.9 mg, 0.01 mmol),, and LiCl (35.7 mg, 0.84 mmol) in DMF (4 mL) was heated under $N_2$ with stirring at 90° C. for 4.5 h. Workup and chromatography (10% EtOAc/hexane) gave 56.1 mg of a 3:1 mixture of methyl 4-(4-cyanophenyl)benzo[b]thiophene-2-carboxylate and an unidentified impurity, which was not removed by recrystallization from EtOH. Treatment of this mixture (ca. 0.19 mmol) with $Me_3Al/NH_4Cl$ (ca. 6.1 equiv, xylene, 130° C., 20 h) gave, after workup and chromatographic purification (30% MeOH/CHCl$_3$), pure 4-(4-carboxamidinophenyl)benzo[b]thiophene-2-carboxamidine bis-hydrochloride (11.9 mg, 17%) as a light yellow solid: $^1$H NMR (CD$_3$OD) δ 8.41 (1H,d,J=0.7 Hz), 8.24 (1H, d,J=8.3 Hz), 8.18 (2H,d,J=8.4 Hz), 7.94 (2H,d,J=8.4 Hz), 7.77 (1H,dd,J=8.3, 8.1 Hz), 7.66 (1H,dd,J=7.3, 0.9 Hz), 4.94 (8H, br s).

Compound 48

4-(Pyrid-3-yl)benzo[b]thiophene-2-carboxamidine bis-hydrochloride

A solution of methyl 4-(trimethylstannyl)benzo[b]thiophene-2-carboxylate (205.1 mg, 0.58 mmol, Compound 67), 3-bromopyridine (67 μl, 0.69 mmol), bis(triphenylphosphine)palladium(II) chloride (22.6 mg, 0.03 mmol),, and LiCl (80.6 mg, 1.90 mmol) in DMF (6 mL) was heated under $N_2$ with stirring at 85° C. for 7 h. Workup and chromatography (10% EtOAc/hexane, then 60% EtOAc/hexane) gave methyl 4-(pyrid-3-yl)benzo[b]thiophene-2-carboxylate (69.8 mg, 45%). Treatment of this ester (0.26 mmol) with 5.0 equiv $Me_3Al/NH_4Cl$ (xylene, 130° C., 6.5 h) gave, after workup and chromatographic purification (30% MeOH/CHCl$_3$), followed by recrystallization from EtOH, 4-(pyrid-3-yl)benzo[b]thiophene-2-carboxamidine bis-hydrochloride (7.0 mg) as an offwhite solid: $^1$H NMR (CD$_3$OD) δ 9.07 (1H,br s), 8.89 (1H,br s), 8.58 (1H,d,J=7.8 Hz), 8.41 (1H,s), 8.25 (1H,d,J=8.3 Hz), 8.03 (1H,br s), 7.81 (1H,t,J=7.8 Hz), 7.71 (1H,d,J=7.3 Hz), 4.95 (5H,br s).

Compound 49

4-(Furan-2-yl)benzo[b]thiophene-2-carboxamidine hydrochloride

Tri-n-butyl(furan-2-yl)tin was prepared in quantitative yield from furan (3.57 mmol) by treatment with n-BuLi (1.1 equiv, THF, −78° C., 2 h) followed by addition of HMPA (1 mL), and tri-n-butyltin chloride (0.83 equiv, −78° C. to 0° C.). A solution of this stannane (360.1 mg, 0.98 mmol), methyl 4-iodobenzo[b]thiophene-2-carboxylate (199.4 mg, 0.63 mmol, Compound 5), bis(triphenylphosphine)palladium(II) chloride (24.2 mg, 0.03 mmol), and LiCl (80.4 mg, 1.89 mmol) in DMF (6 mL) was heated at 80° C. under $N_2$ for 1 h. Workup and chromatography (8% EtOAc/hexane) followed by recrystallization from EtOH provided methyl 4-(furan-2-yl)benzo[b]thiophene-2-carboxylate (70.6 mg, 43% yield). Treatment of this ester (0.27 mmol) with 5.1 equiv $Me_3Al/NH_4Cl$ (xylene, 130° C., 3 h) gave, after workup and chromatographic purification (15% MeOH/CHCl$_3$), 4-(furan-2-yl)benzo[b]thiophene-2-carboxamidine hydrochloride (110.7 mg, 100%, contains ca. 45% by weight of an undetermined inorganic impurity): $^1$H NMR (CD$_3$OD) δ 8.95 (1H,d,J=0.7 Hz), 8.02 (1H,d,J=8.3 Hz), 7.90 (1H,dd,J=7.5,0.7 Hz), 7.82 (1H,dd,J=1.9,0.5 Hz), 7.67 (1H,dd,J=8.0,7.5 Hz), 7.12 (1H,dd,J=3.4,0.5 Hz), 6.71 (1H,dd,J=3.4,1.9 Hz), 4.95 (4H,br s).

Compound 50

4-(Thien-2-yl)benzo[b]thiophene-2-carboxamidine hydrochloride

Trimethyl(thien-2-yl)tin was prepared in 81% yield from thiophene (2.06 mmol) by treatment with n-BuLi (1.06 equiv, THF, −78° C., 1.5 h) followed by addition of trimethyltin chloride (1.03 equiv, −78° C. to 0° C.). A solution of this stannane (218.0 mg, 0.88 mmol), methyl 4-iodobenzo[b]thiophene-2-carboxylate (195.0 mg, 0.61 mmol, Compound 5), bis(triphenylphosphine)palladium(II) chloride (23.1 mg, 0.03 mmol), and LiCl (81.9 mg, 1.93 mmol) in DMF (4 mL) was heated at 80° C. under $N_2$ for 30 min. Workup and chromatography (8% EtOAc/hexane) gave methyl 4-(thien-2-yl)benzo[b]thiophene-2-carboxylate (156.8 mg, 93%). Treatment of this ester (0.45 mmol) with 5.2 equiv $Me_3Al/NH_4Cl$ (toluene, 110° C., 19.5 h) gave, after workup and chromatographic purification (15% MeOH/CHCl$_3$), 4-(thien-2-yl)benzo[b]thiophene-2-carboxamidine hydrochloride (94.5 mg, 70%) as a yellow foam: $^1$H NMR (CD$_3$OD) δ 8.64 (1H,br s), 8.09–8.05 (1H,m), 7.69–7.67 (2H,m), 7.64 (1H,dd,J=5.1,0.9 Hz), 7.54 (1H,dd,J=3.6,0.7 Hz), 7.29 (1H,dd,J=5.1,3.6 Hz), 4.95 (4H,br s).

Compound 51

4-(Benzo[b]furan-2-yl)benzo[b]thiophene-2-carboxamidine hydrochloride (Benzo[b]furan-2-yl)trimethyltin was prepared in quantitative yield from benzo[b]furan (4.53 mmol) by treatment with n-BuLi (1.06 equiv, THF, −78° C., 2 h) followed by addition of trimethyltin chloride (1 equiv, −78° to 25° C.). A solution of this stannane (233.1 mg, 0.83 mmol), methyl 4-iodobenzo[b]thiophene-2-carboxylate (235.6 mg, 0.74 mmol, Compound 5), bis(triphenylphosphine)palladium(II) chloride (29.0 mg, 0.04 mmol), and LiCl (101.3 mg, 2.38 mmol) in DMF (5 mL) was heated at 80° C. under $N_2$ with stirring for 1 h. Workup and chromatography (8% EtOAc/hexane) gave methyl 4-(benzo[b]furan-2-yl)benzo[b]thiophene-2-carboxylate (211.4 mg, 92%). Treatment of this ester (0.68 mmol) with 5.2 equiv $Me_3Al/NH_4Cl$ (xylene, 130° C., 4.5 h) gave, after workup and chromatographic purification (15% $MeOH/CHCl_3$), 4-(benzo[b]furan-2-yl)benzo[b]thiophene-2-carboxamidine hydrochloride (57.6 mg, 25%) as a yellow solid: $^1H$ NMR ($CD_3OD$) δ 9.06 (1H,d,J=0.7 Hz), 8.13 (1H,dd,J=8.0,0.7 Hz), 8.12 (1H,dd,J=8.5,0.9 Hz), 7.75 (1H,br d,J=7.6 Hz), 7.75 (1H,t,J=7.9 Hz), 7.71 (1H,dd,J=8.0,0.7 Hz), 7.54 (1H,d,J=0.7 Hz), 7.43 (1H,ddd,J=7.3,7.1,1.2 Hz), 7.35 (1H,ddd,J=7.8,7.8,0.9 Hz), 4.95 (4H,br s).

Compound 52

Bis-(2-carboxamidinobenzo[b]thien-4-yl) bis-hydrochloride

Dimethyl bis-(2-carboxybenzo[b]thien-4-yl) was isolated as the major, unexpected product from the attempted palladium-mediated coupling of methyl 4-(trimethylstannyl)benzo[b]-thiophene-2-carboxylate and the diethyl enol phosphonate of norcamphor. The latter compound was prepared by treatment of norcamphor (4.13 mmol) with LDA (1.08 equiv, THF, −78° C., 1.5 h) under $N_2$ followed by addition of HMPA (1 mL) and chlorodiethylphosphonate (1.1 equiv, −78° to 25° C.). Workup and purification by flash chromatography (25% EtOAc/hexane) gave the enol phosphonate in 48% yield.

A solution of the phosphonate (79.8 mg, 0.32 mmol), methyl 4-(trimethylstannyl)benzo[b]thiophene-2-carboxylate (103.3 mg, 0.29 mmol, Compound 67), bis(triphenylphosphine)palladium(II) (11.3 mg, 0.02 mmol), and LiCl (42.3 mg, 0.99 mmol) in DMF (5 mL) was heated at 80° C. under $N_2$ with stirring for 3.5 h. Workup and purification by flash chromatography (10% EtOAc/hexane) gave 14.8 mg of slightly impure methyl 4-methylbenzo[b]thiophene-2-carboxylate(ca. 24%) and 11.4 mg (20%) of methyl bis-(2-carboxybenzo[b]thien-4-yl) as a white, crystalline solid. Treatment of the latter ester (0.04 mmol) with 10.3 equiv $Me_3Al/NH_4Cl$ (xylene, 130° C., 24 h) under $N_2$, followed by addition of 5 equiv $Me_3Al/NH_4Cl$ (20 hr) gave, after workup, bis-(2-carboxamidinobenzo[b]thien-4-yl).bis-HCl contaminated with $NH_4Cl$. To this mixture was added aqueous. NaOH solution (1M), the solution was evaporated under vacuum, 10% aqueous HCl was added to the solid residue, and the solution was evaporated to dryness. The residue was eluted down a silica gel plug (30% $MeOH/CHCl_3$) to remove NaCl, and the solvents were removed to afford bis-(2-carboxamidinobenzo[b]thien-4-yl) bis-hydrochloride (20.3 mg, >90% pure, ca. 90% yield) as a light yellow solid: $^1H$ NMR ($CD_3OD$) δ 8.23 (2H,d,J=8.0 Hz), 8.08 (2H,s), 7.83 (2H,t,J=7.8 Hz), 7.69 (2H,d,J=6.6 Hz), 4.98 (8H, br s).

Compound 53

4-[5-(4-carboxamidinophenyl)fur-2-yl]benzo[b]thiophene-2-carboxamidine bis-hydrochloride A solution of tri-n-butyl(furan-2-yl)tin (Compound 49, 447.4 mg, 1.22 mmol), 4-iodobenzo[b]thiophene-2-carbonitrile (Compound 42, 325.8 mg, 1.14 mmol), bis(triphenylphosphine)palladium(II) chloride (38.1 mg, 0.05 mmol), and LiCl (149.0 mg, 3.51 mmol) in DMF (5 mL) was heated at 80° C. under $N_2$ for 1 h. Workup and chromatography (7% EtOAc/hexane) followed by recrystallization from hexane/EtOAc provided 4-(furan-2-yl)benzo[b]thiophene-2-carbonitrile (137.3 mg, 53% yield). A solution of this furan (0.61 mmol) in $CH_2Cl_2$ (3 mL) was cooled to −78° C. and bromine (33 µL, 0.64 mmol) was added dropwise, forming a red solid. The cold-bath was removed and after several min the solid dissolved. After 5 minutes, the reaction was quenched with aq. sodium thiosulfate, diluted with EtOAc, washed with water, aqueous sodium thiosulfate solution, saturated brine, and dried ($MgSO_4$). Filtration and solvent removal (in the dark) afforded a dark oil (231.0 mg). $^1H$ NMR analysis showed the desired 4-(5-bromofuran-2-yl)benzo[b]thiophene-2-carbonitrile along with minor, unidentified impurities, and this material was used without further purification.

4-Bromobenzonitrile (5.49 mmol) and tetrakis(triphenylphosphine)palladium (0.09 mmol) were placed in a dry flask which was then purged with $N_2$. Dry dioxane (40 mL) was added, followed by hexamethylditin (5.95 mmol), and the solution was heated at 80° C. After 3 h, the mixture was cooled, diluted with $Et_2O$, washed with 10% aqueous $NH_4OH$ solution (2×), water, saturated brine, and dried ($MgSO_4$). After filtration and solvent evaporation, the residue was purified by flash chromatography (7% EtOAc/hexane) to provide 4-(trimethylstannyl)benzonitrile (1.37 g, 94%) as a clear, colorless oil.

A solution of this stannane (181.7 mg, 0.68 mmol), the crude bromofuran (ca. 0.61 mmol), bis(triphenylphosphine)palladium(II) chloride (30.5 mg, 0.04 mmol), and LiCl (93.8 mg, 2.21 mmol) in DMF (5 mL) was heated at 60° C. under $N_2$ for 19 h. Workup and purification by flash chromatography (10% EtOAc/hexane) gave impure 4-(5-methylfur-2-yl)benzo[b]thiophene-2-carbonitrile (43.7 mg, containing several impurities) along with the desired product (43.2 mg, slightly impure, ca. 21%). Recrystallization of this material from hexane/EtOAc afforded pure 4-[5-(4-cyanophenyl)fur-2-yl]benzo[b]thiophene-2-carbonitrile (27.3 mg). This material (25.8 mg, 0.08 mmol) was dissolved in THF (3 mL), and lithium hexamethyldisilazide (LiHMDS, 1M, 0.4 mL) was added dropwise via syringe, and the resulting brown solution was stirred at room temperature for 2.5 h. Aqueous HCl (10%, 5 mL) was added, and the heterogeneous mixture was stirred vigorously for 4 h. The mixture was diluted with water and washed with $CHCl_3$ (2×). The aq. phase was evaporated to afford the desired bis-amidine contaminated with a small amount of a monoamidine. Recrystallization of this material from EtOH (hot filtration, evaporation, recrystallization) afforded 4-[5-(4-carboxamidinophenyl)fur-2-yl]benzo[b]thiophene-2-carboxamidine bis-hydrochloride (11.7 mg, 34%) as a bright yellow solid: $^1H$ NMR (CD₃OD) δ 8.84 (1H,s), 8.08 (2H,d,J=8.4 Hz), 8.04 (1H,d,J=8.2 Hz), 8.00 (1H,d,J=7.5 Hz), 7.92 (2H,d,J=8.4 Hz), 7.68 (1H,t,J=7.9 Hz), 7.31 (2H, br s), 4.90 (8H, br s).

Compound 54

4-(Trifluoromethyl)benzo[b]thiophene-2-carboxamidine hydrochloride

3-Fluoro-1-trifluoromethylbenzene was formylated in 80% yield by treatment with LDA and DMF at −78° C. in the usual fashion, and was cyclized to the corresponding benzothiophene with methyl thioglycollate and NaH in 56% yield in the usual fashion. Amidination in the usual fashion gave 4-(trifluoromethyl)benzo[b]thiophene-2-carboxamidine hydrochloride (125.0 mg, 45%) as a pale yellow solid: $^1$H NMR (DMSO-d₆) δ 9.72, 9.39 (2H,2H,2 br s), 8.59 (1H,d,J=8.2 Hz), 8.52 (1H,s), 7.97 (1H,d,J=7.3 Hz), 7.78 (1H,t,J=7.9 Hz).

Compound 55

4-Formylbenzo[b]thiophene-2-carboxamidine hydrochloride

Amidination of methyl 4-(1,3-dioxolan-2-yl)benzo[b]thiophene-2-carboxylate (Compound 22) under the usual conditions yielded directly 4-formylbenzo[b]thiophene-2-carboxamidine hydrochloride (26.7 mg, 19%) as a light orange solid: $^1$H NMR (DMSO-d₆) δ 10.28 (1H,s), 9.76, 9.45 (2H,2H,2 br s), 9.15 (1H,s), 8.60 (1H,d,J=8.2 Hz), 8.22 (1H,dd,J=7.3, 0.9 Hz), 7.88 (1H,dd,J=8.2,7.3 Hz).

Compound 56

4-(Hydroxymethyl)benzo[b]thiophene-2-carboxamidine hydrochloride

A mixture of methyl 4-(hydroxymethyl)benzo[b]thiophene-2-carboxylate. (1.68 g, 7.6 mmol, Compound 27) and Me₃Al/NH₄Cl (1.58M, 34 mL) was heated to 110° C. under N₂ for 50 min and then cooled to 25° C. The mixture was poured onto a stirred slurry of silica gel in CHCl₃, and then filtered. The residue was washed with MeOH and the filtrate was evaporated to dryness. The crude mixture was dissolved in water and was washed with EtOAc to remove non-polar impurities. The aqueous layer was adjusted to pH 12 with dilute NaOH solution (1M), evaporated to dryness, then reacidified with dilute HCl (1M) until pH<5. The solution was evaporated under reduced pressure to dryness, and purified by flash chromatography (15 % MeOH/CHCl₃) to give the acetate salt of the desired amidine. Dissolving this salt in water, followed by adjustment of the pH below 2 with dilute HCl (1M) and solvent removal under reduced pressure afforded 4-(hydroxymethyl)benzo[b]thiophene-2-carboxamidine hydrochloride (385.6 mg, 21%) as a pale beige solid: $^1$H NMR (DMSO-d₆) δ 9.74 (2H,br s), 9.49 (2H,br s), 8.76 (1H,s), 8.05 (1H,d,J=7.9 Hz), 7.56 (1H,t,J=7.6 Hz), 7.51 (1H,d,J=7.0 Hz), 5.61 (1H,t,J=5.6 Hz), 4.88 (2H,d,J=5.5 Hz).

Compound 57

4-Methoxybenzo[b]thiophene-2-carboxamidine hydrochloride

3-Fluoroanisole was formylated in 89% yield by treatment with n-butyl lithium and DMF at −78° C. in the usual fashion, to give 6-fluoro-2-methoxybenzaldehyde. This was annulated with methyl thioglycollate and NaH in 55% yield in the usual fashion to give methyl 4-methoxybenzo[b]thiophene-2-carboxylate. Amidination in the usual fashion gave 4-methoxybenzo[b]thiophene-2-carboxamidine hydrochloride pentahydrate (189.9 mg, 88%) as a yellow solid: $^1$H NMR (CD₃OD) δ 8.39 (1H,d,J=0.5 Hz), 7.58–7.52 (2H,m), 6.98–6.93 (1H,m), 4.90 (14H,br s), 4.01 (3H,s).

Compound 58

4-(Methylthio)benzo[b]thiophene-2-carboxamidine hydrochloride

Sodium thiomethoxide (138.2 mg, 1.98 mmol) in DMSO (2 mL) was added dropwise over 12 min to a solution of 2,6-difluorobenzaldehyde (426.3 mg 3.0 mmol) in DMSO (2 mL), stirred under N₂ on a 20° C. water bath. After 1 h the reaction mixture was poured onto water (20 mL), and the solid was collected by Buchner filtration, rinsed with water and air dried to give 6-fluoro-2-(methylthio)benzaldehyde (208.4 mg, 61%).

This was converted to the corresponding benzothiophene in 25% yield with NaH and methyl thioglycollate in the usual fashion, although precipitation from water failed to give a crystalline product, the material being further purified by preparative tlc, eluting with 6% EtOAc/hexanes. Amidination under the usual conditions gave 4-(methylthio)benzo[b]thiophene-2-carboxamidine hydrochloride (41.3 mg, 80%) as a light yellow glass: $^1$H NMR (DMSO-d₆) δ 9.57 (4H,br s), 8.50 (1H,s), 7.97 (1H,d,J=8.2 Hz), 7.56 (1H,t,J=8.4 Hz), 7.38 (1H,d,J=7.6 Hz), 2.63 (3H,s).

Compound 59

4-(Prop-2-en-1-ylthio)benzo[b]thiophene-2-carboxamidine hydrochloride.

6-Fluoro-2-(prop-2-en-1-ylthio)benzaldehyde was prepared from sodium prop-2-en-1-ylthiolate and 2,6-difluorobenzaldehyde in 72% yield, as described in Compound 58, except that the product was an oil and was extracted from the aqueous layer with ether, and purified by Kugelrohr distillation. This was converted to the corresponding benzothiophene in 50% yield with NaH and methyl thioglycollate in the usual fashion, although precipitation failed to give a crystalline product, the material being further purified by chromatography on silica gel eluting with a CHCl₃/hexanes gradient. Amidination in the usual fashion gave 4-(prop-2-en-1-ylthio)benzo[b]thiophene-2-carboxamidine hydrochloride (104.6 mg, 73%) as a bright yellow glass: $^1$H NMR (DMSO-d₆) δ 9.53 (4H,br s), 8.52 (1H,s), 8.02 (1H,d,J=7.6 Hz), 7.55 (1H,t,J=7.6 Hz), 7.51 (1H,dd,J=7.6,1.2 Hz), 5.87 (1H,ddt,J$_d$=17.1,10.1 Hz,J$_t$=6.7 Hz) 5.20 (1H,dd,J=17.1,1.3 Hz), 5.07 (1H,dd,J=10.1,1.3 Hz), 3.83 (2H,d,J=6.7 Hz).

Compound 60

4-(Benzylthio)benzo[b]thiophene-2-carboxamidine hydrochloride.

2-Benzylthio-6-fluorobenzaldehyde was prepared from sodium benzylthiolate and 2,6-difluorobenzaldehyde in 90% crude yield, as described in Compound 58, and was converted to the corresponding benzothiophene in 39% yield with NaH and methyl thioglycollate in the usual fashion, although precipitation failed to give a crystalline product, the material being further purified by preparative tlc, eluting with 15% EtOAc/hexanes. Amidination under the usual conditions gave 4-(benzylthio)benzo[b]thiophene-2-carboxamidine hydrochloride (150 mg, 87%) as a light yellow glass: $^1$H NMR (DMSO-d$_6$) δ 9.48 (4H,br s), 8.49 (1H,s), 8.02 (1H,m),7.52 (2H,m), 7.37 (2H,d,J=7.6 Hz), 7.29 (2H,t,J=7.6 Hz), 7.24 (1H,t,J=7.5 Hz), 4.41 (2H,s).

Compound 61

4-([R,S]-Tetrahydrofuran-2-yl)benzo[b]thiophene-2-carboxamidine hydrochloride

Tri-n-butyl(2,3-dihydrofuran-5-yl)tin was prepared in 99% yield from 2,3-dihydrofuran (3.97 mmol) by treatment with t-BuLi (1.06 equiv, THF, −78° C. to 0° C.) under N$_2$ followed by cooling to −78° C. and addition of HMPA (1 mL), and tri-n-butyltin chloride (0.93 equiv, −78° C. to 25° C.). A solution of this stannane (322.5 mg, 0.87 mmol), methyl 4-iodobenzo[b]thiophene-2-carboxylate (246.5 mg, 0.77 mmol, Compound 5), bis(triphenylphosphine)palladium(II) chloride (3.25 mg, 0.04 mmol), and LiCl (111.5 mg, 2.63 mmol) in DMF (6 mL) was heated at 90° C. under N$_2$ with stirring for 3 h. Workup gave the 5-aryl-2,3-dihydrofuran contaminated with tri-n-butyltin impurities. Due to the sensitivity of the dihydrofuran towards chromatographic purification, this mixture was used directly for the next step.

The above mixture was dissolved in MeOH (6 mL) and Bromocresol green (ca. 2 mg) was added. Small portions of NaBH$_3$CN were added to the solution with vigorous stirring. When the reaction mixture turned green, a small aliquot of methanolic HCl was added, and the mixture turned yellow. While monitoring the reaction by TLC, this process was repeated until the dihydrofuran was consumed. The reaction mixture was then diluted with Et$_2$O, washed with water (5×), brine, and the organics were dried (MgSO$_4$). After filtration and solvent removal, the residue was purified by flash chromatography (12% EtOAc/hexane) to give methyl 4-([R,S]-tetrahydrofuran-2-yl)benzo[b]thiophene-2-carboxylate (146.1 mg, 72%). Treatment of this ester (0.27 mmol) with 5.0 equiv Me$_3$Al/NH$_4$Cl (xylene, 130° C., 2.5 h) gave, after workup and column chromatography (15% MeOH/CHCl$_3$), followed by preparative tlc (20% MeOH/CHCl$_3$) 4-([R,S]-tetrahydrofuran-2-ylbenzo[b]thiophene-2-carboxamidine hydrochloride (40.4 mg, 53%) as an offwhite solid: $^1$H NMR (CD$_3$OD) δ 8.52 (1H,d,J=0.7 Hz), 7.98-7.94 (1H,m), 7.63-7.56 (2H,m), 5.41 (1H,t,J=7.3 Hz), 5.01 (4H,br s), 4.28-4.22 (1H,m), 4.07-4.02 (1H,m), 2.63-2.55 (1H,m), 2.20-2.10 (2H,m), 1.98-1.86 (1H,m).

Compound 62

4-(1-Morpholino)benzo[b]thiophene-2-carboxamidine hydrochloride 2-(1-Morpholino)-6-fluorobenzaldehyde was prepared, in>90% Kugelrohr distilled yield, by refluxing one equiv of morpholine, 1.1 equiv of triethylamine and 2,6-difluorobenzaldehyde in acetonitrile stirred under N$_2$ for 24 h. This aldehyde was converted to the corresponding benzothiophene in 93% yield with NaH and methyl thioglycollate with heating for 5 min to 60° C. in DMSO, although precipitation failed to give a crystalline product, the material being further purified by preparative tlc, eluting with 20% EtOAc/hexanes. Amidination under the usual conditions gave 4-(1-morpholino)benzo[b]thiophene-2-carboxamidine hydrochloride tetrahydrate (51.4 mg, 95%) as a fluffy yellow solid: $^1$H NMR (CD$_3$OD) δ 8.58 (1H,d,J=0.7 Hz), 7.88 (1H,d,J=8.3 Hz), 7.61 (1H,t,J=8.1 Hz), 7.38 (1H,d,J=7.6 Hz), 4.90 (12H,br s), 4.08-4.04 (4H,m), 3.47-3.43 (4H,m).

Compound 63

4-(E/Z-2-Phenylethenyl)benzo[b]thiophene-2-carboxamidine hydrochloride

Phenylacetylene (1.82 mmol) was converted to E/Z-2-phenyl-1-(tri-n-butylstannyl)ethene, by treatment with tri-n-butyltin hydride and catalytic AIBN in toluene, heated under N$_2$ at 85° C. for 2 h, in 52% yield after purification by flash chromatography (hexane). A mixture of this stannane (215.5 mg, 0.55 mmol), methyl 4-iodobenzo[b]thiophene-2-carboxylate (162.0 mg, 0.51 mmol, Compound 5), bis(triphenylphosphine)palladium(II) chloride (17.2 mg, 0.02 mmol), and LiCl (75.2 mg, 1.77 mmol) in DMF (5 mL) was heated at 80° C. for 2.3 h. Workup and purification by flash chromatography (8% EtOAc/hexane) afforded methyl 4-(E/Z-2-phenylethenyl)benzo[b]thiophene-2-carboxylate (115.6 mg, 77%, E/Z=3.4 as determined by $^1$H NMR integration). This ester (0.39 mmol) was treated with 5.1 equiv of Me$_3$Al/NH$_4$Cl (xylene, 120° C., 4.5 h) under N$_2$ to give, after workup and chromatographic purification (15% MeOH/CHCl$_3$), 4-(E/Z-2-phenylethenyl)benzo[b]thiophene-2-carboxamidine hydrochloride (120.6 mg, 97%, E/Z=4) as an offwhite solid: $^1$H NMR (CD$_3$OD) E-isomer δ 8.81 (1H,d, J=0.5 Hz), 7.97 (1H,d,J=8.3 Hz), 7.91 (1H,d,J=7.5 Hz), 7.81 (1H,d,J=16.2 Hz), 7.73 (2H,d,J=8.3 Hz), 7.64 (1H,t,J=7.8 Hz), 7.45 (2H,t,J=7.3 Hz), 7.44 (1H,d,J=16.2 Hz), 7.35 (1H, br t,J=7.4 Hz), 4.98 (4H,br s). Partial $^1$H NMR (CD$_3$OD) Z-isomer δ 8.36 (1H,d,J=0.7 Hz), 8.29 (1H,d,J=0.7 Hz), 8.08 (1H,d,J=8.1 Hz), 8.01 (1H,dd,J=7.5, 0.7 Hz), 7.06 (1H,d,J=12.3 Hz), 6.96 (1H,d,J=12.3 Hz).

Compound 64

4-[E/Z-2-(3,4-Dimethoxyphenyl)ethenyl]benzo[b]thiophene-2-carboxamidine hydrochloride To a suspension of (2-carboxymethylbenzo[b]thien-4-yl)methyltriphenylphosphonium bromide (190.6 mg, 0.35 mmol, Compound 27) in THF (4 mL) stirred under N$_2$ at 0° C. was added a solution of potassium tert-butoxide in THF (0.54 M, 615 μL). After 30 min the mixture was cooled to −78° C. and a solution of 3,4-dimethoxybenzaldehyde (52.6 mg, 0.32 mmol) in THF (1.5 mL) was added via cannula and the mixture was warmed to 25° C. over 30 min and then to 50° C. for 1.5 h. The mixture was poured onto saturated aqueous NaHCO$_3$ solution and extracted with EtOAc. The organic layer was dried (MgSO$_4$), filtered, and evaporated to dryness, and purified by preparative tlc (1% CH$_3$OH/CHCl$_3$) to afford methyl 4-(E/Z-2-(3,4-dimethoxyphenyl)ethenyl)benzo[b]thiophene-2-carboxylate (24.6 mg, 28%, E/Z=3) as a yellow syrup.

To this ester (24.6 mg, 0.07 mmol) was added a solution of Me$_3$Al/NH$_4$Cl (0.5M, 2.8 mL) in xylenes. The mixture was heated under N$_2$ to 145° C. for 2 h to afford, after workup and flash chromatography (15% CH$_3$OH/CHCl$_3$) 4-[E/Z-2-(3,4-dimethoxyphenyl)ethenyl]benzo[b]thiophene-2-carboxamidine hydrochloride (26.0 mg, 91%, E/Z=3) as an orange solid: $^1$H NMR (CD$_3$OD) δ 8.84 (1H,s), 7.93 (1H,d,J=8.1 Hz), 7.86 (1H,d,J=7.4 Hz), 7.66 (1H,d,J=16.6 Hz), 7.62 (1H,t,J=8.3 Hz), 7.36 (1H,s), 7.36 (1H,d,J=16.0 Hz), 7.15 (1H,d,J=8.2 Hz), 6.90 (1H,d,J=8.0 Hz), 4.96 (4H,br s), 3.96 (3H,s), 3.90 (3H,s).

Compound 65

4-[E/Z-2-(Benzo-1,3-dioxolan-5-yl)ethenyl]benzo[b]thiophene-2-carboxamidine hydrochloride To a suspension of (2-carboxymethylbenzo[b]thien-4-yl)methyltriphenylphosphonium bromide (138.6 mg, 0.25 mmol, Compound 27) in THF (5 mL) stirred under $N_2$ at 0° C. was added a solution of potassium tert-butoxide in THF (0.54M, 450 μL). After 45 min a solution of piperonal (34.6 mg, 0.23 mmol) in THF (2 mL) was added via cannula and the mixture was warmed to 25° C. over 30 min and then to 50° C. for 15 min. The mixture was poured onto saturated aqueous $NaHCO_3$ solution and extracted with $Et_2O$. The organic layer was dried (MgSO4), filtered, and evaporated to dryness, and purified by preparative tlc (10% EtOAc/hexanes) to afford methyl 4-(E/Z-2-(benzo-1,3-dioxolan-5-yl)ethenyl)benzo[b]thiophene-2-carboxylate (24.6 mg. 28%) as a yellow syrup.

This ester (24.6 mg, 0.07 mmol) was added to a solution of $Me_3Al/NH_4Cl$ (0.5M, 3.25 mL) in xylenes. The mixture was heated under $N_2$ to 140° C. for 2.5 h to afford, after workup and flash chromatography (15% $CH_3OH/CHCl_3$) 4-[E/Z-2-(benzo-1,3-dioxolan-5-yl)ethenyl]benzo[b]thiophene-2-carboxamidine hydrochloride (40.2 mg, 69%, >90% E) as a bright yellow film: $^1H$ NMR ($CD_3OD$) δ 8.80 (1H,s), 7.93 (1H,d,J=7.7 Hz), 7.88 (1H,d,J=7.5 Hz), 7.64 (1H,d,J=15.9 Hz), 7.64 (1H,s), 7.37 (1H,d,J=16.1 Hz), 7.35 (1H,s), 7.15 (1H,d,J=8.2 Hz), 6.90 (1H,d,J=8.0 Hz), 6.04 (2H,s), 4.96 (4H,br s).

Compound 66

4-[E/Z,2-(Benzo-1,4-dioxan-6-yl)ethenyl]benzo[b]thiophene-2-carboxamidine hydrochloride To a suspension of (2-carboxymethylbenzo[b]thien-4-yl)methyltriphenylphosphonium bromide (185.0 mg, 0.34 mmol, Compound 27) in THF (5 mL) stirred under $N_2$ at 0° C. was added a solution of potassium tert-butoxide in THF (0.54M, 600 μL). After 45 min a solution of 1,4-benzodioxane-6-carbaldehyde (50.4 mg, 0.31 mmol) in THF (2 mL) was added via cannula and the mixture was warmed to 25° C. over 30 min and then to 50° C. for 20 min. The mixture was poured onto saturated aqueous $NaHCO_3$ solution, and extracted with $Et_2O$. The organic layer was washed with water and saturated brine, dried (MgSO4), filtered, and evaporated to dryness, and purified by preparative tlc (0.6% $CH_3OH/CHCl_3$) to afford methyl 4-(E/Z-2-(benzo-1,4-dioxan-6-yl)ethenyl)benzo[b]thiophene-2-carboxylate (104.2 mg. 96%) as a yellow solid.

This ester (104.2 mg, 0.30 mmol) was added to a solution of $Me_3Al/NH_4Cl$ (0.5M, 3.0 mL) in xylenes. The mixture was heated under $N_2$ to 145° C. for 3 h to afford, after workup and flash chromatography (15% $CH_3OH/CHCl_3$) 4-[E/Z-2-(benzo-1,4-dioxan-6-yl)ethenyl]benzo[b]thiophene-2-carboxamidine hydrochloride (91.8 mg, 83%, E/Z=4:1) as a bright orange solid: $^1H$ NMR ($CD_3OD$) E-isomer δ 8.79 (1H,s), 7.95 (1H,d,J=8.0 Hz), 7.88 (1H,d,J=8.0 Hz), 7.64 (1H,t,J=15.9 Hz), 7.64 (1H,s), 7.33 (1H,d,J=16.0 Hz), 7.25 (1H,d,J=2.0 Hz), 7.17 (1H,dd,J=8.0.2.0 Hz), 6.91 (1H,d,J=8.0 Hz), 4.96 (4H,br s).

Compound 67

4-[E-2-(Furan-2-yl)ethenyl]benzo[b]thiophene-2-carboxamidine hydrochloride

A solution of furfural (2.41 mmol) and iodoform (4.81 mmol) in THF (15 mL) was added dropwise via cannula to a 0° C. solution of $CrCl_2$ (15.41 mmol) in THF (20 mL) stirred under $N_2$. After 2.6 h, the reaction mixture was poured onto a stirred suspension of Celite (3.5 g) in $Et_2O$ (50 mL), stirred for 15 min, and filtered. The organics were washed with water until the aqueous phase was no longer green, then washed with aqueousd sodium sulfite solution (2×), water, saturated brine, and dried (MgSO4). After filtration the solvent was removed (the flask was covered with foil) to afford 944.6 mg of a mixture of 2-(furan-2-yl)-1-iodoethene (E/Z=1.7) and iodoform (ca. 1.3:1 $CHI_3$:alkene as determined by $^1H$ NMR integration) as a yellow-brown solid. This mixture was used without further purification.

A solution of methyl 4-iodobenzo[b]thiophene-2-carboxylate (1.116 g, 3.51 mmol, Compound 5), hexamethylditin (0.9 mL, 4.11 mmol), and tetrakis(triphenylphosphine)palladium (95.6 mg, 0.08 mmol) in dioxane (20 mL) were heated at 100° C. under $N_2$ with stirring for 3 h. The reaction was cooled to 25° C., diluted with $Et_2O$, washed with 10% aqueous $NH_4OH$ solution, water (2×), saturated brine, and dried (MgSO4). Filtration, solvent removal, and purification by flash chromatography (8% EtOAc/hexane) gave methyl 4-(trimethylstannyl)benzo[b]thiophene-2-carboxylate (1.112 g, 89%) as a white solid.

A solution of 2-(furan-2-yl)-1-iodoethene (566 mg, ca. 0.77 mmol), methyl 4-(trimethylstannyl)benzo[b]thiophene-2-carboxylate (199.6 mg, 0.56 mmol), bis(triphenylphosphine)palladium(II) chloride (19.7 mg, 0.03 mmol), and LiCl (99.5 mg, 2.34 mmol) in DMF (6 mL) was heated at 80° C. under $N_2$ with stirring for 3.25 h. Cooling to 25° C., followed by aqueous workup, and purification of the residue by flash chromatography (8% EtOAc/hexane) repeated twice, gave methyl 4-[E/Z-2-(furan-2-yl)ethenyl]benzo[b]thiophene-2-carboxylate (24.1 mg, 15%, E/Z=1.6). Treatment of this ester (0.08 mmol) with 5.1 equiv $Me_3Al/NH_4Cl$ (xylene, 130° C., 25.5 h) gave, after workup and chromatographic purification (2×, 15% $MeOH/CHCl_3$), 4-[E/Z-2-(furan-2-yl)ethenyl]benzo[b]thiophene-2-carboxamidine hydrochloride (14.8 mg, 57%, E/Z=5) as an offwhite solid: $^1H$ NMR ($CD_3OD$) E-isomer δ 8.66 (1H,s), 7.89 (1H,d,J=8.2 Hz), 7.79 (1H,d,J=7.4 Hz), 7.59-7.54 (3H,m). 7.22 (1H,d,J=16.1 Hz), 6.57 (1H,d,J=3.3 Hz), 6.52 (1H,dd,J=3.3,1.7 Hz), 4.94 (4H,br s). Partial $^1H$ NMR ($CD_3OD$) Z-isomer δ 8.28 (1H,s), 7.27 (1H,d,J=7.4 Hz), 6.83 (1H,d,J=12.3 Hz), 6.69 (1H,d,J=12.3 Hz), 6.29 (1H,dd,J=3.3,1.8 Hz), 6.10 (1H,d,J=3.3 Hz).

Compound 68

4-[E-2-(Pyrid-3-yl)ethenyl]benzo[b]thiophene-2-carboxamidine hydrochloride

A solution of 3-bromopyridine (20.76 mmol), 3-hydroxy-3-methyl-1-butyne (24.76 mmol), bis(triphenylphosphine)palladium(II) chloride (0.20 mmol), and CuI (0.22 mmol) in $Et_3N$ (25 mL) was stirred under $N_2$ at 25° C. for 3 h, and warmed to 70° C. for 14.5 h (TLC indicated no reaction at room temperature). After cooling to 25° C., the reaction mixture was diluted with Et₂O, washed with water (3×), saturated brine, and dried (MgSO₄). After filtration and solvent removal, the residue (3.28 g) was dissolved in toluene (30 mL) and NaOH (840 mg, 21 mmol) was added. The heterogeneous mixture was heated under N₂ with stirring at 100° C. for 2.5 h, and cooled to 25° C. Activated charcoal was stirred with the dark mixture, followed by a Celite filtration. The Celite was rinsed with Et₂O, the combined filtrates were concentrated under reduced pressure, and the residue was purified by bulb-to-bulb distillation (ca. 0.1 mm Hg, ca. 30°–45° C.) to afford 3-ethynylpyridine (1.16 g, 54%) as a clear, colorless liquid.

3-Ethynylpyridine (1.58 mmol) was converted to E-2-(pyrid-3-yl)-1-(tri-n-butylstannyl)ethene, as described in Compound 63, in 78% yield after purification by flash chromatography (10% EtOAc/hexane). A solution of this stannane (205.6 mg, (0.52 mmol), methyl 4-iodobenzo[b]thiophene-2-carboxylate (139.8 mg, 0.44 mmol, Compound 5), bis(triphenylphosphine)palladium(II) chloride (15.8 mg, 0.02 mmol), and LiCl (57.9 mg, 1.36 mmol) in DMF (5 mL) was heated at 80° C. for 2.3 h. Aqueous workup and purification by flash chromatography (50% EtOAc/hexane) provided methyl 4-[E-2-(pyrid-3-yl)ethenyl]benzo[b]thiophene-2-carboxylate (115.4 mg, ca. 89%) contaminated with a small amount of a tri-n-butyl tin impurity. This material was treated with 5.1 equiv of Me₃Al/NH₄Cl (xylene, 130° C., 8.4 h) to afford, after workup and chromatographic purification (20% MeOH/CHCl₃), 4-[E-2-(pyrid-3-yl)ethenyl]benzo[b]thiophene-2-carboxamidine bis-hydrochloride mono-MeOH (151.1 mg, 100%) as an offwhite solid: ¹H NMR (CD₃OD) δ 8.88 (1H,s), 8.85 (1H,br s), 8.49 (1H,br d,J=6.0 Hz), 8.34 (1H,d,J=9.9 Hz), 7.99 (1H,d,J=7.9 Hz), 7.97 (1H,d,J=16.4 Hz), 7.92 (1H,d,J=6.8 Hz), 7.63 (1H,t,J=7.7 Hz), 7.55 (1H,dd,J=8.0, 4.8 Hz), 7.46 (1H,d,J=16.4 Hz), 4.90 (5H,br s).

Compound 69

4-[E/Z-2-(Quinolin-3-yl)ethenyl]benzo[b]thiophene-2-carboxamidine hydrochloride

3-Bromoquinoline (3.83 mmol) was converted to 3-ethynylquinoline, as described in Compound 68, in 18% yield after purification by flash chromatography (15% EtOAc/hexane). 3-Ethynylquinoline (0.69 mmol) was converted to E/Z-2-(quinolin-3-yl)-1-(tri-n-butylstannyl)ethene in 50% yield (E/Z=1 as determined by ¹H NMR integration), as described in Compound 63, after purification by flash chromatography (10% EtOAc/hexane). A solution of this stannane (154.2 mg, 0.35 mmol), methyl 4-iodobenzo[b]thiophene-2-carboxylate (105.6 mg, 0.33 mmol, Compound 5), bis(triphenylphosphine)palladium(II) chloride (12.2 mg, 0.02 mmol), and LiCl (44.1 mg, 1.04 mmol) in DMF (4 mL) was heated under N₂ with stirring at 80° C. for 2.6 h. Aqueous workup and purification by flash chromatography (30% EtOAc/hexane) provided 72.3 mg of methyl 4-[E/Z-2-(quinolin-3-yl)ethenyl]benzo[b]thiophene-2-carboxylate contaminated with tri-n-butyl tin impurities. This material was treated with 5.0 equiv of Me₃Al/NH₄Cl (xylene, 130° C., 5.5 h) to afford, after workup and chromatographic purification (20% MeOH/CHCl₃), 4-[E/Z-2-(quinolin-3-yl)ethenyl]benzo[b]thiophene-2-carboxamidine bis-hydrochloride (36.4 mg, 27%, E/Z=2) as an offwhite solid: ¹H NMR (CD₃OD) δ 9.58 (0.67H,br s), 9.29 (0.67H,br s), 9.00 (0.67H,s), 8.73 (0.33H,br s), 8.60 (0.33H,br s), 8.42 (0.33H,s), 8.32–8.25 (1.33H,m), 8.19 (0.67H,d,J=12.0 Hz), 8.10–7.99 (2.67H,m), 7.98–7.89 (1.33H,m), 7.81–7.65 (1.67H,m), 7.49–7.43 (0.67H,m), 7.38 (0.33H,br d,J=7.5 Hz), 7.17 (0.33H,d,J=11.8 Hz), 4.91 (4H,m).

Compound 70

4-[E-(2-Benzo[b]thien-2-yl)ethenyl]benzo[b]thiophene-2-carboxamidine hydrochloride Benzo[b]thiophene-2-carbaldehyde was prepared in quantitative yield from benoz[b]thiophene (7.46 mmol) via lithiation (1.07 eq η-BuLi, THF, −78° C., 1.5 h) and subsequent formylation (2.1 eq DMF, −78° C.; HOAc quench). Condensation of this aldehyde (71.2 mg, 0.44 mmol) with the Wittig reagent prepared from (2-carboxymethylbenzo[b]thien-4-yl)methyltriphenylphosphonium bromide (Compound 27, 203.0 mg, 0.37 mmol) and potassium tert-butoxide (0.29M, 1.4 mL) afforded, after purification by flash chromotography (10% EtOAc/hexane), methyl 4-[E/Z-(benzo[b]thien-2-yl)ethenyl]benzo[b]thiophene-2-carboxylate (78.0 mg, 60%, E/Z=3.2 as determined by ¹H NMR integration). Treatment of this mixture (0.22 mmol) with 5 equiv of Me₃Al/NH₄Cl (xylene, 130° C., 23 h) gave, after workup and chromatographic purification (20% MeOH/CHCl₃), the desired amidine (69.3 mg, 84%) as a 9:1 E/Z mixture. Recrystallization from EtOH/EtOAc provided pure 4-[E-(2-benzo[b]thien-2-yl)ethenyl]benzo[b]thiophene-2-carboxamidine hydrochloride (21.8 mg) as a bright yellow solid: ¹H NMR (CD₃OD) δ 8.72 (1H,s), 7.96 (1H,d,J=7.5 Hz), 7.89 (1H,d,J=7.5 Hz), 7.83–7.81 (1H,m), 7.77–7.75 (1H,m), 7.70 (1H,d J=15.8 Hz), 7.62 (1H,t,J=7.8 Hz), 7.56 (1H,d,J=15.8 Hz), 7.47 (1H,s), 7.35–7.32 (2H,m), 4.91 (4H,br s).

Compound 71

4-[E-2-(Benzo[b]thien-4-yl)ethenyl]benzo[b]thiophene-2-carboxamidine hydrochloride A mixture of methyl 4-(1,3-dioxolan-2-yl)benzo[b]thiophene-2-carboxylate (537.9 mg, 2.04 mmol, Compound 22) and KOH (137.0 mg, 2.44 mmol) in MeOH (10 mL) was refluxed under N₂ for 4 h. The reaction mixture was acidified with aqueous HCl (1M, 2.4 mL) and extracted into Et₂O. The organic layer was washed with water, dried (MgSO₄), and evaporated to dryness. The crude product was redissolved in CHCl₃, and was extracted with NaOH (1M, 2 mL). The aqueous layer was reacidified with HCl (1M, 2 mL) and extracted with CHCl₃ to afford upon removal of the solvent under reduced pressure 4-(1,3-dioxan-2-yl)benzo[b]thiophene-2-carboxylic acid (155.4 mg, 31%) as a white solid.

A mixture of the above carboxylic acid (155.4 mg, 0.62 mmol) and Cu powder (19.7 mg, 0.31 mmol) in quinoline (10 mL) was heated under N₂ to 230° C. for 4.5 h. The reaction was allowed to cool to 25° C. and EtOAc (15 mL) was added to the reaction flask and the contents were stirred vigorously for 10 min. The mixture was poured into a separatory funnel containing dilute hydrochloric acid (1M, 35 mL). The organic layer was washed with saturated aqueous NaHCO₃ solution, water, and saturated brine, dried (MgSO₄), filtered and concentrated under reduced pressure. The resulting black oil was purified by column chromatography (15% EtOAc/hexanes) to afford 4-(1,3-dioxan-2-yl)benzo[b]thiophene (88.6 mg, 69%) as a golden syrup.

A solution of the above material (88.6 mg, 0.43 mmol) in CH₃CN/H₂O (9:1, 5 mL) and TFA (20 μL) was stirred under N₂ for 1 h at 25° C. The reaction mixture was poured onto saturated aqueous NaHCO₃ solution and was extracted with EtOAc. The organic layer was washed with water and saturated brine, dried (MgSO₄), filtered, and evaporated to dryness to afford 4-formylbenzo[b]thiophene (68.5 mg, 98%) as a yellow syrup.

To a suspension of methyl (2-carboxymethylbenzo[b]thien-4-yl)methyltriphenylphosphonium bromide (277.4 mg, 0.51 mmol, Compound 27) in THF (8 mL) stirred under N₂ at 0° C. was added potassium tert-butoxide (0.54M, 860 μL). After 30 minutes the reaction was cooled to −78° C. and a solution of 4-formylbenzo[b]thiophene (68.5 mg, 0.42 mmol) in THF (5 mL) was added via cannula. The reaction was warmed slowly to 50° C. for 20 min and was poured onto saturated aqueous NaHCO₃ solution, and extracted with EtOAc. The organics were washed with water and saturated brine, dried (MgSO₄), filtered and evaporated to dryness to yield, after column chromatography on silica gel (CHCl₃) methyl 4-[E/Z-(2-benzo[b]thien-4-yl)ethenyl]benzo[b]thiophene-2-carboxylate (124.9 mg, 84%) as a yellow syrup.

To a solution of the above ester (124.9 mg, 0.36 mmol) in xylenes (5 mL) was added a solution of Me₃Al/NH₄Cl (0.5M, 3.6 mL) in xylenes. The reaction was heated under N₂ to 145° C. for 1.25 h then cooled to 25° C., poured over a silica gel slurry (10 g silica gel in 20 mL CHCl₃), and filtered. The silica was rinsed with CHCl₃ to remove any non-polar impurities and then with 15% MeOH/CHCl₃ to remove the product. Removal of the solvent under reduced pressure afforded 4-[E/Z-2-(benzo[b]thien-4-yl)ethenyl]benzo[b]thiophene-2-carboxamidine hydrochloride (120.2 mg, 91%, E/Z=3:1) as a yellow solid: ¹H NMR (CD₃OD) mixture of E- and Z-isomers δ 8.83 (s), 8.32 (s), 7.88–8.08 (m), 7.69–7.74 (m), 7.64 (1H,s), 7.04–7.58 (m), 4.96 (4H,br s).

Compound 72

4-[E-2-(Benzo[b]thien-5-yl)ethenyl]benzo[b]thiophene-2-carboxamidine hydrochloride 4-Bromothiophenol (1.89 g, 10 mmol) was added dropwise to a slurry of hexane-washed NaH (60% oil suspension, 0.42 g, 10.5 mmol) in DMF (10 mL), stirred under N₂ at 25° C. When the gas evolution died down, 2-bromo-1,1-dimethoxyethane (1.86 g, 11 mmol) was added. After 2 h the reaction mixture was poured onto water (50 mL), and was extracted with ether (3×20 mL). The combined extracts were washed with dilute Na₂CO₃ solution (25 mL), water (2×25 mL), saturated brine (25 mL) and dried (MgSO₄). The solvent was removed under reduced pressure to give 2-(4-bromophenylthio)-1,1-dimethoxyethane (2.53 g, 91%) as a yellow oil. This acetal (555.6 mg, 2.0 mmol) was added to polyphosphoric acid (2.47 g), heated to 225° C. under N₂, with stirring. After 2 min the dark reaction mixture was cooled on a 20° C. water bath, and saturated NaHCO₃ solution (50 mL) was added cautiously, with vigourous stirring. When gas evolution had died down, the mixture was extracted with ether (3×25 mL). The combined extracts were washed with saturated NaHCO₃ solution (50 mL), water (50 mL), saturated brine (50 mL) and dried (MgSO₄). The solvent was removed under reduced pressure, and the residue was purified by Kugelrohr distillation (190° C./0.1 mmHg) and preparative tlc on silica (4% EtOAc in hexanes) to give 5-bromobenzo[b]thiophene (115 mg, 27%) as a white solid.

A slurry of 5-bromobenzo[b]thiophene (200 mg, 0.94 mmol), CuI (4.6 mg, 0.02 mmol), bis(triphenylphosphine)palladium(II) chloride (14.4 mg, 0.02 mmol) and 2-methyl-3-butyn-2-ol (110 μL, 1.13 mmol) in Et₃N (3 mL) was stirred under N₂ at 70° C. for 7.5 h, at which time further Et₃N (2 mL) and 2-methyl-3-butyn-2-ol (200 μL) were added. After heating an additional 16 h, the mixture was cooled, diluted with Et₂O, washed with water (3×), saturated brine, and dried (MgSO₄). After filtration and solvent removal, the residue was dissolved in benzene (4 mL) and solid NaOH (95.2 mg, 2.38 mmol) added, and the mixture was heated at reflux for 22 h. After cooling, decolorizing charcoal was added to the reaction mixture, and the slurry was stirred for several min, then filtered through a pad of Celite, rinsing the Celite with Et₂O. Solvent removal and purification by flash chromatography (8% EtOAc/hexane) afforded 5-ethynylbenzo[b]thiophene (42.8 mg, 29%) as a light yellow oil.

This alkyne (0.27 mmol) was converted to the corresponding E-vinylboronate by treatment with catecholborane (70° C., benzene, 3.5 h). After cooling to room temperature, methyl 4-iodobenzo[b]thiophene-2-carboxylate (91.1 mg, 0.28 mmol, Compound 5), bis(triphenylphosphine)palladium(II) chloride (13.2 mg, 0.02 mmol), and sodium methoxide (2M in MeOH, 0.5 mL) were added to the benzene solution, and the mixture was heated to reflux under N₂. After 2.5 h, the reaction was cooled, diluted with EtOAc, washed with water (2×), saturated brine, and dried (MgSO₄). Filtration and solvent removal gave a residue which was purified by flash chromatography (10% EtOAc/hexane) to afford methyl 4-[E-2-(benzo[b]thien-5-yl)ethenyl]benzo[b]thiophene-2-carboxylate (58.4 mg, 62% overall based on 5-ethynylbenzo[b]thiophene). This ester (0.17 mmol) was treated with 5.0 equiv of Me₃Al/NH₄Cl (xylene, 130° C., 2.5 h) under N₂ to give, after workup and chromatographic purification (15% MeOH/CHCl₃), the desired amidine (41.9 mg) contaminated with several minor impurities. Recrystallization from EtOH/EtOAc provided 4-[E-2-(benzo[b]thien-5-yl)ethenyl]benzo[b]thiophene-2-carboxamidine hydrochloride (22.7 mg, 36%) as a yellow solid: ¹H NMR (CD₃OD) δ 8.59 (1H,s), 8.16 (1H,br s), 8.03 (1H,d,J=8.3 Hz), 7.96 (1H,d,J=8.3 Hz), 7.71 (1H,d,J=7.1 Hz), 7.67 (1H,d,J=5.4 Hz), 7.62–7.58 (4H,m), 7.42 (1H,d,J=5.4 Hz), 4.90 (4H,br s).

Compound 73

4-[E-2-(2-Carboxamidinobenzothien-4-yl)ethenyl]benzo[b]thiophene-2-carboxamidine bis-hydrochloride To a suspension of methyl (2-carboxymethylbenzo[b]thien-4-yl)methyltriphenylphosphonium bromide (206.7 mg, 0.38 mmol, Compound 27) in THF (5 mL) stirred under N₂ at 0° C. was added potassium tert-butoxide (0.54M, 670 μL). After 50 minutes the reaction was cooled to −78° C. and a solution of methyl 4-formylbenzo[b]thiophene-2-carboxylate (75.6 mg, 0.34 mmol, Compound 22) in THF (2.5 mL) was added via cannula. The reaction was warmed to 25° C. for 45 min and was poured onto saturated aqueous NaHCO₃ solution, and the bright yellow precipitate was filtered and dried under vacuum to yield methyl 4-[E/Z-2-(2-carboxymethylbenzo[b]thien-4-yl)ethenyl]benzo[b]thiophene-2-carboxylate (124.9 mg, 84%).

A mixture of this diester (120.2 mg, 0.32 mmol) and catalytic I$_2$ in 1,4-dioxane (10 mL) was stirred under N$_2$ at 100° C. for 20 h, cooled to 25° C., and then poured onto 10% aqueous Na$_2$S$_2$O$_3$ solution and extracted with CHCl$_3$. The organic layer was dried (MgSO$_4$), filtered, and evaporated to dryness to afford methyl 4-[E-2-(2-carboxymethylbenzo[b]thien-4-yl)ethenyl]benzo[b]thiophene-2-caboxylate (120.5 mg, 100%) as a bright yellow solid.

To a solution of this diester (120.5 mg, 0.32 mmol) in xylenes (6.5 mL) was added a solution of Me$_3$Al/NH$_4$Cl (0.5M, 6.4 mL) in xylenes. The reaction was heated under N$_2$ to 140° C. for 18 h then cooled to 25° C., poured over a silica gel slurry (10 g silica gel in 20 mL CHCl$_3$), and filtered. The silica was rinsed with MeOH and the resultant yellow solution was evaporated to dryness. The solid was redissolved in water (20 mL), and treated with aqueous NaOH solution (1M, 4 mL). The precipitate was filtered, washed with water, and then redissolved in dilute HCl (1M) at pH 1. Filtration through a 20 micron filter followed by removal of water under reduced pressure afforded 4-[E-2-(2-carboxamidinobenzo[b]thien-4-yl)ethenyl]benzo[b]thiophene-2-carboxamidine bis-hydrochloride trihydrate (80.0 mg, 58%) as a yellow solid: $^1$H NMR (DMSO-d$_6$) δ 9.34 (4H,br s), 9.17 (2H,s), 8.13 (2H,t,J=8.0 Hz), 8.08 (2H,s), 7.72 (2H,t,J=8.0 Hz), 3.32 (6H,br s).

Compound 74

4-[E-2-(2-Carboxamidinobenzo[b]thien-5-yl)ethenyl]-benzo[b]thiophene-2-carboxamidine bis-hydrochloride To a suspension of methyl (2-carboxymethylbenzo[b]thien-4-yl)methyltriphenylphosphonium bromide (125.2 mg, 0.23 mmol, Compound 27) in THF (3 mL) stirred under N$_2$ at 0° C. was added potassium tert-butoxide (0.54M, 400 μL). After 1 h the reaction was cooled to −78° C. and a solution of methyl 5-formyl-benzo[b]thiophene-2-carboxylate (45.8 mg, 0.21 mmol, Compound 122) in THF (2.5 mL) was added via cannula. The reaction was warmed to 25° C. for 20 min and was poured onto saturated aqueous NaHCO$_3$ solution, and extracted with Et$_2$O. The organic layer was dried (MgSO$_4$), filtered, and evaporated to dryness to afford, after preparative tlc (1% CH$_3$OH/CHCl$_3$) methyl 4-[E/Z-2-(2-carboxymethylbenzo[b]thien-5-yl)ethenyl]-benzo[b]thiophene-2-carboxylate (68.6 mg, 81%) as a yellow solid.

A mixture of this diester (68.6 mg, 0.17 mmol) and catalytic I$_2$ in 1,4-dioxane (5 mL) was stirred under N$_2$ at 100° C. for 22 h, cooled to 25° C., and then poured over 10% aqueous Na$_2$S$_2$O$_3$ solution, and extracted into CHCl$_3$. The organic layer was dried (MgSO$_4$), filtered, and evaporated to dryness to afford methyl 4-[E-2-(2-carboxymethylbenzo[b]thien-5-yl)ethenyl]benzo[b]thiophene-2-carboxylate (63.2 mg, 92%) as a light yellow solid.

To this diester (63.2 mg, 0.15 mmol) was added a solution of Me$_3$Al/NH$_4$Cl (0.5M, 6.2 mL) in xylenes. The reaction was heated under N$_2$ to 140° C. for 2 h then cooled to 25° C., poured over a silica gel slurry (10 g silica gel in 20 mL CHCl$_3$), and filtered. The silica was rinsed with MeOH and the resultant yellow solution was evaporated to dryness. The solid was dissolved in water (40 mL), and treated with aqueous NaOH (1M, 4 mL). The precipitate was filtered, washed with water, and dissolved in dilute HCl (1M) at pH 1. Filtration through a 20 micron filter followed by removal of water and under reduced pressure afforded 4-]E-2-(2-carboxamidinobenzo[b]thien-5-yl)ethenyl]benzo[b]thiophene-2-carboxamidine bis-hydrochloride trihydrate (58.0 mg, 74%) as a yellow-orange solid: $^1$H NMR (CD$_3$OD) δ 8.92 (1H,s), 8.36 (1H,s), 8.35 (1H,s), 8.12 (2H,q,J=7.3 Hz), 7.98–8.04 (3H,m), 7.69 (1H,t,J=7.9 Hz), 7.62 1H,d,J=16.3 Hz), 4.96 (4H,br s).

Compound 75

4-[(Furan-2-yl)ethynyl]benzo[b]thiophene-2-carboxamidine hydrochloride

Furfural (6.04 mmol) was converted to 1,1-dibromo-2-(furan-2-yl)ethene by treatment with Ph$_3$P/CBr$_4$ (CH$_2$Cl$_2$, 0° C.). The crude dibromoolefin (2.42 mmol) in THF (5 mL) was treated with TBAF (7.4 mL, 1M in THF), and the mixture was stirred under N2 at 25° C. for 18 h. The reaction was diluted with hexane, washed with water (3×), brine, and the organics were dried (MgSO$_4$). After filtration, the solvents were distilled at atmospheric pressure to afford a dark brown liquid, with an unpleasant, lacrymatory odor. $^1$H NMR analysis showed relatively pure 1-bromo-2-(furan-2-yl)-ethene contaminated with hexane. This material was stored at −20° C. and used without further purification.

A solution of the bromoalkyne (420 mg), methyl 4-(trimethylstannyl)benzo[b]thiophene-2-carboxylate (188.6 mg, 0.53 mmol, Compound 67), bis(triphenylphosphine)palladium(II) chloride (18.4 mg, 0.03 mmol), and LiCl (70.0 mg, 1.65 mmol) in DMF (5 mL) was heated at 85° C. for 3 h. Workup and purification by flash chromatography (7% EtOAc/hexane), followed by preparative tlc (15% EtOAc/hexane), provided methyl 4-[(furan-2-yl)ethynyl]benzo[b]thiophene-2-carboxylate (25.5 mg, 18%). Treatment of this ester (0.09 mmol) with 5.1 equiv Me$_3$Al/NH$_4$Cl (xylene, 115° C., 16 h) gave, after workup and chromatographic purification (12% MeOH/CHCl$_3$), 4-[(furan-2-yl)ethynyl]benzo[b]thiophene-2-carboxamidine hydrochloride (13.7 mg, ca. 48%, ca. 93% pure): $^1$H NMR (CD$_3$OD) δ 8.43 (1H,s), 8.07 (1H,d,J=8.3 Hz), 7.68 (1H,d,J=6.9 Hz), 7.64 (1H,d,J=1.9 Hz), 7.56 (1H,t,J=8.1 Hz), 6.82 (1H,d,J=3.4 Hz), 6.51 (1H,dd,J=3.4, 1.9 Hz), 4.98 (4H,br s).

Compound 76

4-(Phenylethynyl)benzo[b]thiophene-2-carboxamidine hydrochloride

A solution of methyl 4-iodobenzo[b]thiophene-2-carboxylate (105.8 mg, 0.33 mmol, Compound 5), phenylacetylene (40 μl, 0.36 mmol), bis(triphenylphosphine)-palladium(II) chloride (5.3 mg, 0.007 mmol), and CuI (6.6 mg, 0.03 mmol) in Et$_3$N (1 mL) was stirred under N$_2$ at 25° C. for 1.6 h. Workup and purification by flash chromatography (8% EtOAc/hexane) afforded methyl 4-(phenylethynyl)benzo[b]thiophene-2-carboxylate (198.2 mg, 100%) as a light yellow solid. Treatment of this ester (0.34 mmol) with 4.1 equiv Me$_3$Al/NH$_4$Cl (toluene, 110° C., 23 h) gave, after workup and chromatographic purification (15% MeOH/CHCl$_3$), 4-(phenylethynyl)benzo[b]thiophene-2-carboxamidine hydrochloride dihydrate (65.0 mg, 62%) as a light yellow solid: $^1$H NMR (CD$_3$OD) δ 8.61 (1H,d,J= 0.7 Hz), 8.10 (1H,br d,J=8.1 Hz), 7.76 (1H,dd,J=7.4,0.8 Hz), 7.74–7.69 (2H,m), 7.66 (1H,dd,J=8.3, 8.3 Hz), 7.50–7.44 (3H,m), 4.95 (8H,br s).

Compound 77

4-[(Benzo-1,3-dioxolan-5-yl)ethynyl]benzo[b]thiophene-2-carboxamidine hydrochloride A solution of triphenylphosphine (0.14 mol) in $CH_2Cl_2$ (40 mL) was added via cannula to a 0° C. stirred solution of carbon tetrabromide (0.098 mol) in $CH_2Cl_2$ (40 mL) under $N_2$. After stirring 5 min, a solution of piperonal (0.034 mol) in $CH_2Cl_2$ (20 mL) was added dropwise via cannula, and the reaction was stirred for 60 min. The mixture was transferred to an Erlenmeyer flask and hexane (200 mL) was added with vigorous stirring. The solids were removed by filtration, washed with hexane, and the combined organics were evaporated. Hexane (200 mL) was added to the residue, the solids were filtered and washed with hexane, and the solvent was rigorously removed under reduced pressure. The residue was dissolved in THF (100 mL), cooled to −78° C. under $N_2$, and n-BuLi (2.13M, 34 mL) was added dropwise via cannula. The dark-colored reaction mixture was stirred at −78° C. for 1 h, stirred at 0° C. for 1 h, and quenched with aqueous $NH_4Cl$ solution. The mixture was diluted with $Et_2O$, washed with water (3×), saturated brine, and dried ($MgSO_4$). Filtration and solvent removal gave an oil which was purified by bulb-to-bulb distillation to afford 5-ethynyl-benzo-1,3-dioxolane (3.83 g, 76%) as a clear, colorless oil.

A slurry of this alkyne (156.1 mg, 1.06 mmol), methyl 4-iodobenzo[b]thiophene-2-carboxylate (301.4 mg, 0.95 mmol, Compound 5), bis(triphenylphosphine)palladium(II) chloride (24.0 mg, 0.03 mmol), and CuI (8.8 mg, 0.04 mmol) in $Et_3N$ (3 mL) was stirred under $N_2$ at 25° C. for 2 h. Workup and purification by flash chromatography (10% EtOAc/hexane) afforded methyl 4-[(benzo-1,3-dioxolan-5-yl)ethynyl]benzo[b]thiophene-2-carboxylate (208.4 mg, 65%) as a light yellow solid. Treatment of this ester (0.62 mmol) with 5.1 equiv $Me_3Al/NH_4Cl$ (toluene, 130° C., 5.5 h) gave, after workup and chromatographic purification (15% MeOH/CHCl$_3$), 4-[(benzo-1,3-dioxolan-5-yl)ethynyl]benzo[b]thiophene-2-carboxamidine hydrochloride (119.4 mg, 54%) as a bright yellow solid: $^1$H NMR (CD$_3$OD) δ 8.54 (1H,s) 8.02 (1H,d,J=8.0 Hz), 7.67 (1H, d,J=7.4 Hz), 7.59 (1H,t,J=7.8 Hz), 7.20 (1H,dd,J=8.0, 1.5 Hz), 7.12 (1H,d,J=1.5 Hz), 6.89 (1H,d,J=8.1 Hz), 6.05 (2H,s), 4.85 (4H,br s).

Compound 78

4-(5-Phenylfur-2-yl)benzo[b]thiophene-2-carboxamidine hydrochloride

A solution of methyl 4-(5-bromofur-2-yl)benzo[b]thiophene-2-carboxylate (ca. 0.42 mmol Compound 53), dimethyldiphenyltin (143.0 mg, 0.47 mmol), bis(triphenylphosphine) palladium (II) (16.0 mg, 0.02 mmol), and LiCl (61.5 mg, 1.45 mmol) in DMF (6 mL) was heated at 80° C. under $N_2$ for 19 h. Workup and purification by flash chromatography (10% EtOAc/hexane) gave methyl 4-(5-phenylfur-2-yl)benzo[b]thiophene-2-carboxylate (33.4 mg, 24%) as a bright yellow solid. Treatment of this ester (0.09 mmol) with 5.0 equiv $Me_3Al/NH_4Cl$ (toluene, 120° C., 17.5 h) gave, after workup and chromatographic purification (15% MeOH/CHCl$_3$), 4-(5-Phenylfur-2-yl)benzo[b]thiophene-2-carboxamidine hydrochloride (23.1 mg, 65%) as a bright yellow solid: $^1$H NMR (CD$_3$OD) δ 8.81 (1H, d,J=0.6 Hz), 7.93 (1H,d,J=8.0 Hz), 7.87 (1H,d,J=7.8 Hz), 7.81 (1H,dd,J=8.4, 0.9 Hz), 7.60 (1H,t,J=7.9 Hz), 7.43 (2H,t,J=7.7 Hz), 7.31 (1H,br t,J=7.4 Hz), 7.16 (1H,d,J =3.6 Hz), 6.97 (1H,d,J=3.6 Hz), 4.95 (4H,v br s).

Compound 79

4-[5-(Benzo-1,3-dioxolan-5-yl)fur-2-yl]benzo[b]thiophene-2-carboxamidine hydrochloride A solution of 5-bromo-1,3-benzodioxolane (145 μL, 1.20 mmol), tri-n-butyl(furan-2-yl)tin (396.5 mg, 1.08 mmol, Compound 49), bis(triphenylphosphine) palladium(II) chloride (41.7 mg, 0.06 mmol), and LiCl (140.6 mg, 3.31 mmol) in DMF (5 mL) was heated at 80° C. for 1.7 h. Workup and chromatographic purification (3% EtOAc/hexane) provided 2-(benzo-1,3-dioxolan-5-yl)furan (214.4 mg), contaminated with a minor, unidentified impurity. Treatment of this mixture (197.3 mg, ca. 1.05 mmol) with n-BuLi (1.07 equiv, THF, −78° C., 1 h) followed by HMPA (1 mL) and chlorotri-n-butyltin (1.05 equiv, −78° C. to 25° C.) gave, after workup, a mixture of 2-(benzo-1,3-dioxolan-5-yl)-5-(tri-n-butylstannyl)furan and the starting furan (405.7 mg, 3:1 ratio). A solution of this mixture (ca. 0.6 mmol stannane), methyl 4-iodobenzo[b]thiophene-2-carboxylate (192.0 mg, 0.60 mmol, Compound 5), bis(triphenylphosphine)-palladium(II) chloride (37.5 mg, 0.05 mmol), and LiCl (79.6 mg, 1.88 mmol) in DMF (5 mL) was heated at 70° C. under $N_2$ for 1.5 h. Workup and recrystallization of the crude material from hexane/EtOAc afforded methyl 4-[5-(benzo-1,3-dioxolan-5-yl)fur-2-yl]benzo[b]thiophene-2-carboxylate (125.2 mg, 55%) as a bright yellow solid. Treatment of this ester (0.32 mmol) with 5.0 equiv $Me_3Al/NH_4Cl$ (toluene, 130° C., 3.5 h) gave, after workup and chromatographic purification (15% MeOH/CHCl$_3$), 4-[5-(benzo-1,3-dioxolan-5-yl)fur-2-yl]benzo[b]thiophene-2-carboxamidine hydrochloride. (93.5 mg, 72%) as a bright yellow solid: $^1$H NMR (CD$_3$OD) δ 8.84 (1H,d,J=0.7 Hz), 7.96 (1H,d,J=8.3 Hz), 7.91 (1H,dd,J=7.7,0.7 Hz), 7.64 (1 h, t,J=7.9 Hz), 7.37 (1H,dd,J=8.1,1.7 Hz), 7.33 (1H,d,J=1.6 Hz), 7.16 (1H,d,J=3.6 Hz), 6.92 (1H,d,J=8.1 Hz), 6.86 (1H,d,J=3.6 Hz), 6.00 (2H,s), 4.91 (4H,br s).

Compound 80

4-[E-2-(4-N,N-Dimethylaminophenyl)ethenyl]benzo[b]thiophene-2-carboxamidine hydrochloride To a suspension of (2-carboxymethylbenzo[b]thien-4-yl)methyltriphenylphosphonium bromide (80.1 mg, 0.15 mmol, Compound 27) in THF (3 mL) stirred under $N_2$ at 0° C. was added a solution of potassium tert-butoxide in THF (0.54M, 250 μL). After 25 min the mixture was cooled to −78° C. and a solution of 4-dimethylaminobenzaldehyde (18.2 mg, 0.12 mmol) in THF (2 mL) was added via cannula and the mixture was warmed to 25° C. over 30 min and then to 60° C. for 40 min. The mixture was poured onto saturated aqueous NaHCO$_3$ solution and extracted with EtOAc. The organic layer was washed with water, saturated brine, dried (MgSO$_4$), filtered, and evaporated to dryness, and purified by preparative tlc (0.5% CH$_3$OH/CHCl$_3$) to afford methyl 4-(E/Z-2-(4-dimethylaminophenyl)ethenyl)benzo[b]thiophene-2-carboxylate (14.4 mg. 35%) as a yellow solid.

To this ester (14.4 mg, 0.04 mmol) in xylenes (1 mL) was added a solution of Me$_3$Al/NH$_4$Cl (0.5M, 470 μL) in xylenes. The mixture was heated under $N_2$ to 140° C. for 2.5 h then to 100° C. for 12 h to afford, after workup and flash chromatography (10% CH₃OH/CHCl₃) 4-[E-2-(4-dimethylaminophenyl)ethenyl]benzo[b]thiophene-2-carboxamidine hydrochloride (8.8 mg, 58%) as an orange-red solid: ¹H NMR (CD₃OD) δ 8.79 (1H,s), 7.90 (1H,d,J=8.3 Hz), 7.85 (1H,d,J=7.6 Hz), 7.62 (1H,t,J=7.8 Hz), 7.59 (2H,d,J=9.0 Hz), 7.57 (1H,d,J=16.6 Hz), 7.35 (1H,d,J=15.9 Hz), 6.83 (2H,d,J=9.0 Hz), 4.95 (4H,br s), 3.04 (6H,s).

Compound 81

4-[E/Z-2-(3-Methoxyphenyl)ethenyl]benzo[b]thiophene-2-carboxamidine hydrochloride To a suspension of (2-carboxymethylbenzo[b]thien-4-yl)methyltriphenylphosphonium bromide (65.3 mg, 0.12 mmol, Compound 27) in THF (3 mL) stirred under N₂ at 0° C. was added a solution of potassium tert-butoxide in THF (0.54M, 200 μL). After 20 min neat m-anisaldehyde (13.5 mg, 0.10 mmol) was added and the mixture was warmed to 50° C. for 30 min. The mixture was poured onto saturated aqueous NaHCO₃ solution and extracted with Et₂O. The organic layer was washed with water, saturated brine, dried (MgSO₄), filtered, and evaporated to dryness, and purified by preparative tlc (CHCl₃) to afford methyl 4-(E/Z-2-(3-methoxyphenyl)ethenyl)benzo[b]thiophene-2-carboxylate (29.5 mg, 92%) as a yellow film.

To this ester (29.5 mg, 0.09 mmol) in xylenes (3 mL) was added a solution of Me₃Al/NH₄Cl (0.5M, 910 μL) in xylenes. The mixture was heated under N₂ to 140° C. for 1 h to afford, after workup and chromatography (15% CH₃OH/CHCl₃), 4-[E/Z-2-(3-methoxyphenyl)ethenyl]benzo[b]thiophene-2-carboxamidine hydrochloride (30.0 mg, 96%, E/Z=4) as an yellow solid: ¹H NMR (CD₃OD) E-isomer δ 8.82 (1H,s), 7.99 (1H,d,J=8.2 Hz), 7.92 (1H,d,J=7.5 Hz), 7.81 (1H,d,J=16.1 Hz), 7.66 (1H,t,J=7.8 Hz), 7.43 (1H,d,J=16.2 Hz), 7.25–7.35 (3H,m), 6.95 (1H,dd,J=8.0, 1.1 Hz), 4.96 (4H,v br s), 3.95 (3H,s).

Compound 82

4-[(Indan-5-yl)ethynyl]benzo[b]thiophene-2-carboxamidine hydrochloride

To a solution of indan (16.33 mmol) in hexane (40 mL) was added iron powder (1.67 mmol) and bromine (17.31 mmol), and the mixture was covered with foil and stirred at room temperature for 2.5 h. Saturated aqueous NaHCO₃ solution (50 mL) was added to the stirred reaction mixture, which was then diluted with Et₂O. The layers were separated and the organics were dried (MgSO₄). Filtration and solvent evaporation gave a residue which was eluted through silica gel with hexane. Solvent removal gave a mixture of 5- and 4-bromoindan (2.25 g, 70%, 4.5:1 ratio). A solution of these bromides (1.55 g, 7.87 mmol), 2-methyl-3-butyn-2-ol (0.92 mL, 9.52 mmol), bis(triphenylphosphine)palladium(II) chloride (112.4 mg, 0.16 mmol), and CuI (35.4 mg, 0.18 mmol) in Et₃N (30 mL) was stirred under N₂ at 60° C. for 4 h. Workup and purification by flash chromatography (25% EtOAc/hexane) afforded 5-(3-hydroxy-3-methylbutynyl)indan (534.6 mg, 34%). This alcohol (2.65 mmol) was dissolved in benzene (20 mL), powdered NaOH (8.82 mmol) was added, and the heterogeneous mixture was heated at reflux under N₂ for 23.5 h. After cooling, the reaction mixture was diluted with Et₂O, washed with water (3x), saturated brine, and dried (MgSO₄). Filtration and solvent removal gave an oil which was purified by flash chromatography (5% EtOAc/hexane) to provide 5-ethynylindan (299.6 mg, 80%) as a clear, colorless oil.

A solution of this alkyne (105.4 mg, 0.74 mmol), methyl 4-iodobenzo[b]thiophene-2-carboxylate (202.4 mg, 0.63 mmol, Compound 5), bis(triphenylphosphine)palladium(II) chloride (9.8 mg, 0.01 mmol), and CuI (12.2 mg, 0.06 mmol) in Et₃N (3 mL) was stirred at 25° C. under N₂ for 18 h. Workup and purification by flash chromatography (10% EtOAc/hexane) afforded methyl 4-[(indan-5-yl)ethynyl]benzo[b]thiophene-2-carboxylate (200.8 mg, 95%) as a viscous, gold oil which solidified upon standing. Treatment of this ester (0.60 mmol) with 5.3 equiv Me₃Al/NH₄Cl (toluene, 130° C., 3 h) gave, after workup and chromatographic purification (15% MeOH/CHCl₃), 4-[(indan-5-yl)ethynyl]benzo[b]thiophene-2-carboxamidine hydrochloride (98.6 mg, 46%) as a yellow solid: ¹H NMR (CD₃OD) δ 8.55 (1H,s), 8.02 (1H,d,J=8.3 Hz), 7.68 (1H,dd,J=7.4,0.8 Hz), 7.59 (1H,t,J=7.8 Hz), 7.50 (1H,br s), 7.42 (1H,d,J=7.8 Hz), 7.27 (1H,d,J=7.6 Hz), 4.90 (4H,v br s), 2.94 (4H,t,J=7.4Hz), 2.11 (2H,quint,J=7.4 Hz).

Compound 83

4-[E,Z-2-(2,3-Dihydrobenzo[b]furan-5-yl)ethenyl]benzo[b]thiophene-2-carboxamidine hydrochloride A quantitative yield of 5-bromo-2,3-dihydrobenzofuran (418.0 mg, 0.21 mmol) was obtained from the reaction of 2,3-dihydrofuran (250.0 mg, 2.1 mmol) with Br₂ (400.0 mg, 2.5 mmol) in CH₂Cl₂ (5 mL) at 0° C. under N₂. The reaction was diluted with CHCl₃, washed with 10% sodium metabisulfite, water, saturated brine, dried (MgSO₄), filtered and evaporated to dryness. The bromide (117.9 mg, 0.59 mmol) was treated with 2 equiv. of n-BuLi in THF at −78° C. under N₂ followed by DMF to yield 2,3-dihydrobenzofuran-5-carboxaldehyde (51.3 mg, 58%) after workup and chromatography (12% EtOAc/hexanes) as a pale yellow syrup.

To a stirring suspension of 2-carboxymethylbenzo[b]-thien-4-ylmethyltriphenylphosphonium bromide (227.5 mg, 0.42 mmol, Compound 27) in THF (5 mL) at 0° C. under N₂, was added potassium tert-butoxide (0.54M, 705 μL) in THF. After 30 min the mixture was cooled to −78° C. and a solution of the 2,3-dihydrobenzofuran-5-carboxaldehyde (51.3 mg, 0.35 mmol) in THF (3 mL) was added via cannula. After 10 min the mixture was warmed to 25° C. and after 30 more minutes to 50° C. Reaction was complete in 35 minutes at 50° C. whereupon the mixture was diluted with Et₂O and washed with saturated NaHCO₃ solution. The organic layer was washed with water, saturated brine, dried (MgSO₄), filtered, and evaporated to dryness to yield, after chromatography (10% EtOAc/hexanes), methyl 4-(E/Z-2-(2,3-dihydrobenzofuran-5-yl)ethenyl)benzo[b]thiophene-2-carboxylate (94.4 mg, 81%, E/Z=5) as a yellow solid. The ester was amidinated with 5 equiv. NH₄Cl/Me₃Al in xylenes (8 mL) at 145° C. under N₂ for 2 h then stirred at 25° C. for 16 h to yield after workup and chromatography (10% MeOH/CHCl₃) 4-[2-(2,3-dihydrobenzofuran-5-yl)ethenyl]benzo[b]thiophene-2-carboxamidine hydrochloride (72.0 mg, 72%, E/Z=6) as a bright yellow solid: ¹H NMR (CD₃OD) E-isomer δ 8.80 (1H,s), 7.92 (1H,d,J=8.1 Hz), 7.85 (1H,d,J=7.5 Hz), 7.64 (1H,s), 7.62 (1H,d,J=15.7 Hz), 7.61 (1H,t,J=7.4 Hz), 7.44 (1H,dd,J=8.3,1.2 Hz), 6.80 (1H,d,J=8.3 Hz), 4.96 (4H,v br s), 4.63 (2H,t,J=8.7 Hz), 3.29 (2H,t,J=8.7 Hz).

Compound 84

4-[5-(6-Carboxamidinonaphth-2-yl)fur-2-yl]benzo[b]thiophene-2-carboxamidine bis-hydrochloride n-BuLi (2.5M,, 0.21 mL) was added to a 0° C. solution of 2,2,6,6-tetramethylpiperidine (90 μL, 0.53 mmol) in THF (3 mL). The solution was stirred for 30 min at 0° C. under $N_2$, cooled to −78° C., and a solution of 4-(furan-2-yl)benzo[b]thiophene2-carbonitrile (109.4 mg, 0.48 mmol, Compound 53) and chlorotrimethyltin (110.6 mg, 0.56 mmol) in THF (3 mL) was added slowly dropwise via cannula. After 1 h the cold-bath was removed, and after an additional 20 min the reaction was quenched with water, diluted with $Et_2O$, washed with water (2×), saturated brine, and dried ($MgSO_4$). Filtration and solvent removal provided a mixture of the starting furan and the desired furylstannane (170.0 mg, ca. 1:3). These were separated by preparative tlc (20% EtOAc/hexane) to afford 47.7 mg (ca. 20%) of slightly impure 4-[5-(trimethylstannyl)fur-2-yl]benzo[b]thiophene-2-carbonitrile.

A solution of this stannane (0.099 mmol), 2-cyano-6-iodonaphthalene (31.3 mg, 0.11 mmol, prepared from 2-cyano-6-methoxynaphthalene via sequential $BBr_3$ demethylation, triflation ($Tf_2O$/Hunig's base), stannylation ($Sn_2Me_6$, Pd(PPh$_3$)$_4$), and iodine-metal exchange ($I_2$)), bis(triphenylphosphine)palladium(II) chloride (5.6 mg, 0.008 mmol), and LiCl (13.8 mg, 0.32 mmol) in DMF (5 mL) was heated at 70° C. under $N_2$ with stirring for 2 h. Workup and recrystallization of the crude material from benzene gave 4-[5-(6-cyanonaphth-2-yl)fur-2-yl]benzo[b]thiophene-2-carbonitrile (21.4 mg, 58%). This dinitrile (0.05 mmol) was dissolved in THF (6 mL), and LiHMDS (1.0M, 0.34 mL) was added dropwise. The dark mixture was stirred at room temperature under $N_2$ for 4.3 h, and more LiHMDS (0.12 mL) was added. After an additional 2.5 h, 10% aqueous HCl (5 mL) was added and the heterogeneous mixture stirred vigorously for 1.5 h. The volatiles were removed under reduced pressure, and the residue was purified by preparative tlc (60% CHCl$_3$, 30% MeOH, 5% HOAc, 5% H$_2$O). Aqueous HCl (10%) was added, and the water was removed under reduced pressure. The residue was recrystalized from ethanol to provide 4-[5-(6-carboxamidinonaphth-2-yl)fur-2-yl]benzo[b]thiophene-2-carboxamidine bishydrochloride trihydrate (11.0 mg, 40%) as a yellow solid: $^1$H NMR (CD$_3$OD/DMSO-d$_6$) δ 8.99 (1H,s), 8.56 (1H,s), 8.49 (1H,s), 8.24 (1H,d,J=8.7 Hz), 8.20 (2H,s), 8.12 (1H,d,J=8.0 Hz), 8.11 (1H,d,J=7.6 Hz), 7.88 (1H,dd,J=8.7,1.8 Hz), 7.75 (1H,t,J=7.8 Hz), 7.42 (1H,d,J=3.5 Hz), 7.40 (1H,d,J=3.5 Hz), 4.71 (14H,v br s).

Compound 101

5-Fluorobenzo[b]thiophene-2-carboxamidine hydrochloride 2,5-Difluorobenzaldehyde was converted to the corresponding benzothiophene in 30% yield with NaH and methyl thioglycollate in the usual fashion, and was amidinated under the usual conditions to give 5-fluorobenzo[b]thiophene-2-carboxamidine hydrochloride decahydrate (160.6 mg, 64%) as a light yellow solid: $^1$H NMR (CD$_3$OD) δ 8.22 (1H,s), 8.06 (1H,dd,J=4.7,8.9 Hz), 7.77 (1H,dd,J=2.4,9.0 Hz), 7.41 (1H,dt,J$_d$=2.4 Hz,J$_t$=9.0 Hz), 4.91 (24H,brs).

Compound 102

5-Chlorobenzo[b]thiophene-2-carboxamidine hydrochloride

1-Chloro-4-fluorobenzene was formylated in 69% yield by treatment with LDA and DMF in THF at −78° C. in the usual fashion, and was cyclized to the corresponding benzothiophene with methyl thioglycollate and NaH in 53% yield in the usual fashion. Amidination in the usual fashion gave 5-chlorobenzo[b]thiophene-2-carboxamidine hydrochloride (85.6 mg, 69%) as a pale yellow solid: $^1$H NMR (DMSO-d$_6$) δ 9.60 (4H,br s), 8.37 (1H,s), 8.26 (1H,d,J=8.8 Hz), 8.20 (1H,d,J=1.5 Hz), 7.64 (1H,ddd,J=8.8,1.5,<1 Hz).

Compound 103

5-Bromobenzo[b]thiophene-2-carboxamidine hydrochloride

1-Bromo-4-fluorobenzene was formylated in 84% yield by treatment with LDA and DMF in THF at −78° C. in the usual fashion, and was cyclized to the corresponding benzothiophene with methyl thioglycollate and NaH in 63% yield in the usual fashion. Amidination in the usual fashion gave 5-bromobenzo[b]thiophene-2-carboxamidine hydrochloride (102.7 mg, 70%) as a pale orange solid: $^1$H NMR (DMSO-d$_6$) δ 9.60 (4H,br s), 8.36 (1H,s), 8.34 (1H,d,J=1.8 Hz), 8.19 (1H,d,J=8.8 Hz), 7.74 (1H,dd,J=8.7,1.9 Hz).

Compound 104

5-Iodobenzo[b]thiophene-2-carboxamidine hydrochloride

4-Fluoro-1-iodobenzene was formylated in 77% yield by treatment with LDA and DMF in THF at −78° C. in the usual fashion, and was cyclized to the corresponding benzothiophene with methyl thioglycollate and NaH in 55% yield in the usual fashion. Amidination in the usual fashion gave 5-iodobenzo[b]thiophene-2-carboxamidine hydrochloride (62 mg, 36%) as a pale yellow solid: $^1$H NMR (DMSO-d$_6$) δ 9.57 (4H,br s), 8.49 (1H,sl br s), 8.34 (1H,s), 8.03 (1H,d,J=8.5 Hz), 7.86 (1H,sl br d, J=8.5 Hz).

Compound 105

5-Methylbenzo[b]thiophene-2-carboxamidine hydrochloride

4-Fluorotoluene was formylated in 49% yield by treatment with n-butyl lithium at −60° C., followed by DMF in THF at −78° C. in the usual fashion, and was cyclized at 80° C. for 15 min to the corresponding benzothiophene acid with methyl thioglycollate and NaH in 12% recrystallised yield. The acid was converted to the corresponding acid chloride by refluxing for 1 h with SOCl$_2$, followed by amidination in the usual fashion and recrystalisation from EtOH at −20° C. to give 5-methylbenzo[b]thiophene-2-carboxamidine hydrochloride (15.0 mg, 26%) as pale yellow needles: $^1$H NMR (DMSO-d$_6$) δ 9.56 (2H,br s), 9.29 (2H,br s), 8.34 (1H,s), 8.07 (1H,d,J=8.6 Hz), 7.86 (1H,sl br s), 7.44 (1H,sl br d,J=8.6 Hz), 2.46 (3H,s).

Compound 106

5-Ethylbenzo[b]thiophene-2-carboxamidine hydrochloride

A mixture of 5-ethenylbenzo[b]thiophene-2-carboxamidine hydrochloride (55.6 mg, 0.23 mmol, Compound 114 and 10% Pd/C (ca. 50 mg) in MeOH (8 mL) was stirred under an atmosphere of H$_2$ for 2.25 h. The mixture was filtered through Celite, and the residue washed with MeOH, and the filtrate was concentrated under reduced pressure to afford 5-ethylbenzo[b]thiophene-2-carboxamidine hydrochloride (15.0 mg, 28%) as a light solid: $^1$H NMR (CD$_3$OD) δ 8.24 (1H,s), 7.98 (1H,d,J=8.5 Hz), 7.90 (1H,s), 7.53 (1H,d,J=8.4 Hz), 4.96 (4H,br s), 2.86 (2H,q,J=7.6 Hz), 1.35 (3H,t,J=7.6 Hz).

Compound 107

5-Propylbenzo[b]thiophene-2-carboxamidine hydrochloride

A mixture of 5-(E/Z-prop-1-enyl)benzo[b]thiophene-2-carboxamidine hydrochloride (62.0 mg, 0.25 mmol, Compound 116 and 10% Pd/C (ca. 25 mg) in MeOH (6 mL) was stirred under an atmosphere of H$_2$ for 5 h. The mixture was filtered through Celite, and the residue washed with MeOH, and the filtrate was concentrated under reduced pressure to afford 5-propylbenzo[b]thiophene-2-carboxamidine hydrochloride (15.0 mg, 28%) as a white solid: $^1$H NMR (CD$_3$OD) δ 8.23 (1H,s), 7.97 (1H,d,J=8.6 Hz), 7.88 (1H,s), 7.51 (1H,d,J=8.5 Hz), 4.95 (4H,brs), 2.80 (2H,t,J=6.9 Hz), 1.77 (2H,m), 1.02 (3H,t,J=7.3 Hz).

Compound 108

5-Butylbenzo[b]thiophene-2-carboxamidine hydrochloride

A mixture of 5-(E/Z-but-1-enyl)benzo[b]thiophene-2-carboxamidine hydrochloride (62.6 mg, 0.23 mmol, Compound 117) and 10% Pd/C (ca. 25 mg) in MeOH (6 mL) was stirred under an atmosphere of H$_2$ for 5 h. The mixture was filtered through Celite, the residue washed with MeOH, and the filtrate was concentrated under reduced pressure to afford 5-butylbenzo[b]thiophene-2-carboxamidine hydrochloride (43.6 mg, 69%) as a white solid: $^1$H1NMR (CD$_3$OD) δ 8.23 (1H,s), 7.98 (1H,d,J=8.0 Hz), 7.88 (1H,s), 7.52 (1H,d,J=8.0 Hz), 4.96 (4H,br s), 2.8 (2H,t,J=7.0 Hz), 1.72 (2H,m), 1.44 (2H,m), 1.01 (3H,t,J=7.3 Hz).

Compound 109

5-([R/S]-2-Methylbutyl)benzo[b]thiophene-2-carboxamidine hydrochloride

A mixture of 5-([R,S]-E/Z-2-methylbut-1-enyl)benzo[b]thiophene-2-carboxamidine hydrochloride (6.3 mg, 0.02 mmol, Compound 118) and 10% Pd/C (ca. 10 mg) in MeOH (4 mL) was stirred under an atmosphere of H$_2$ for 3 h. The mixture was filtered through Celite, the residue washed with MeOH, and the filtrate was concentrated under reduced pressure to afford 5-([R,S]-2-methylbutyl)benzo[b]thiophene-2-carboxamidine hydrochloride (4.0 mg, 63%) as a yellow film: $^1$H NMR (CD$_3$OD) δ 8.23 (1H,s), 7.97 (1H,d,J=8.4 Hz), 7.85 (1H,s), 7.48 (1H,d,J=8.4 Hz), 4.95 (4H,br s), 2.86 (1H,dd,J=13.8,6.9 Hz), 2.58 (1H,dd,J=13.7,8.4 Hz), 1.78 (1H,m), 1.48 (1H,m), 1.28 (1H,m), 0.99 (3H,t,J=7.4 Hz), 0.92 (3H,d,J=6.7 Hz).

Compound 110

5-(3-Methylbutyl)benzo[b]thiophene-2-carboxamidine hydrochloride

A mixture of 5-(E/Z-3-methylbut-1-enyl)benzo[b]thiophene-2-carboxamidine hydrochloride (3.3 mg, 0.01 mmol, Compound 119) and 10% Pd/C (ca. 10 mg) in MeOH (3 mL) was stirred under an atmosphere of H$_2$ for 18 h. The mixture was filtered through Celite, the residue washed with MeOH, and the filtrate was concentrated under reduced pressure to afford 5-(3-methylbutyl)benzo[b]thiophene-2-carboxamidine hydrochloride (2.5 mg, 75%) as a yellow film: $^1$H NMR (CD$_3$OD) δ 8.20 (1H,s), 7.96 (1H,d,J=8.5 Hz), 7.87 (1H,s), 7.49 (1H,d,J=8.6 Hz), 4.96 (4H,brs), 2.83 (2H,t,J=7.7 Hz), 1.63 (2H,m), 1.02 (6H,d,J=6.1 Hz).

Compound 111

5-Hexylbenzo[b]thiophene-2-carboxamidine hydrochloride

A mixture of 5-(E/Z-hex-1-enyl)benzo[b]thiophene-2-carboxamidine hydrochloride (27.7 mg, 0.09 mmol, Compound 120) and 10% Pd/C (ca. 30 mg) in MeOH (5 mL) was stirred under an atmosphere of H$_2$ for 17 h. The mixture was filtered through Celite, the residue washed with MeOH, and the filtrate was concentrated under reduced pressure to afford 5-hexylbenzo[b]thiophene-2-carboxamidine hydrochloride (20.3 mg, 73%) as a beige film: $^1$H NMR (CD$_3$OD) δ 8.23 (1H,s), 7.96 (1H,d,J=8.0 Hz), 7.88 (1H,s), 7.51 (1H,d,J=8.0 Hz), 4.96 (4H,br s), 2.82 (2H,t,J=7.6 Hz), 1.72 (2H,quintet,J=7.5 Hz), 1.38 (6H,m), 0.94 (6H,t,J=6.9 Hz).

Compound 112

5-(2-Cyclopropylethyl)benzo[b]thiophene-2-carboxamidine hydrochloride

A mixture of 5-(E/Z-2-cyclopropylethenyl)benzo[b]thiophene-2-carboxamidine hydrochloride (7.8 mg, 0.03 mmol, Compound 121) and 10% Pd/C (ca. 10 mg) in MeOH (4 mL) was stirred under an atmosphere of H$_2$ for 3 h. The mixture was filtered through Celite, the residue washed with MeOH, and the filtrate was concentrated under reduced pressure to afford 5-(2-cyclopropyl)benzo[b]thiophene-2-carboxamidine hydrochloride (5.6 mg, 71%) as a white film: $^1$H NMR (CD$_3$OD) δ 8.21 (1H,s), 7.96 (1H,d,J=8.4 Hz), 7.88 (1H,s), 7.51 (1H,d,J=8.4 Hz), 4.96 (4H,br s), 2.92 (2H,t,J=7.6 Hz), 1.63 (2H,q,J=7.5 Hz), 0.47 (2H,m), 0.09 (2H,m).

Compound 113

5-(2-Hydroxyethyl)benzo[b]thiophene-2-carboxamidine hydrochloride

To a solution of methyl 5-ethenylbenzo[b]thiophene-2-carboxylate (102.2 mg, 0.47 mmol) in THF (5 mL) at 0° C. under N$_2$ was added BH$_3$.THF (1M, 44 μL). After 1 h water (3 mL), aqueous NaOH solution (1M, 1.4 mL), and H$_2$O$_2$ (30%, 1.6 mL) were added. The mixture was stirred for 30 min then extracted twice with Et$_2$O. The organic layer was dried (MgSO$_4$), filtered, and evaporated to dryness. The crude solid was purified by preparative tlc (3% MeOH/CHCl$_3$) to give methyl 5-(2-hydroxy)ethylbenzo[b]thiophene-2-carboxylate (68.7 mg, 62%) as a white solid. To a solution of this ester in xylenes (5 mL) was added a solution of NH$_4$Cl/Me$_3$Al (0.86M, 2.7 mL). The mixture was heated to 120° C. for 15 h under N$_2$ to provide after workup and preparative tlc (20% MeOH/CHCl$_3$) 5-(2-hydroxy)ethylbenzo[b]thiophene-2-carboxamidine hydrochloride (43.0 mg, 58%) as a yellow solid: $^1$H NMR (CD$_3$OD) δ 8.24 (1H,s), 8.00 (1H,d,J=8.5 Hz), 7.94 (1H,s), 7.51 (1H,d,J=8.4 Hz), 4.95 (4H,br s), 3.88 (2H,t,J=6.7 Hz), 3.02 (2H,t,J=6.7 Hz).

Compound 114

5-(Ethenyl)benzo[b]thiophene-2-carboxamidine hydrochloride

Methyl 5-formylbenzo[b]thiophene-2-carboxylate (107.1 mg, 0.49 mmol, Compound 122) was reacted with methyl triphenylphosphonium iodide and KOBu$^t$ in the usual fashion to give methyl 5-ethenylbenzo[b]-thiophene-2-carboxylate (102.9 mg, 97%) as a white solid. A mixture of this ester (111.7 mg, 0.51 mmol) and Me$_3$Al/NH$_4$Cl solution (0.86M, 3 mL) was heated under N$_2$ at 120° C. for 15 h to afford, after workup and preparative tlc (20% MeOH/CHCl$_3$), 5-ethenylbenzo[b]thiophene-2-carboxamidine hydrochloride trihydrate (67.5 mg, 45%) as a yellow solid: $^1$H NMR (CD$_3$OD) δ 8.27 (1H,s), 8.07 (1H,s), 8.04 (1H,d,J=8.6 Hz), 7.80 (1H,d,J=8.5 Hz), 6.94 (1H,dd,J=17.6,11.0 Hz), 5.98 (1H,d,J=17.5 Hz), 5.41 (1H,d,J=10.9 Hz), 4.96 (12H,br s).

Compound 115

5-(1-Methylethenyl)benzo[b]thiophene-2-carboxamidine hydrochloride

To a solution of methyl 5-formylbenzo[b]thiophene-2-carboxylate (78.9 mg, 0.36 mmol, Compound 122) in THF (10 mL) stirred under N$_2$ at −78° C. was added methylmagnesium bromide (3M, 1.75 mL, 5.25 mmol). The reaction was quenched after 15 min with saturated aqueous NaHCO$_3$ solution and extracted with EtOAc. The organic layer was washed with water, and dried (MgSO$_4$). Filtration and removal of solvent followed by preparative tlc (1.6% MeOH/CHCl$_3$) yielded methyl 5-(1-hydroxyethyl)benzo[b]thiophene-2-carboxylate (60.8 mg, 72%) as a pale beige solid.

To a solution of oxalyl chloride (27 μL,0.31 mmol) in CH$_2$Cl$_2$ (5 mL) stirred under N$_2$ at −78° C. was added DMSO (44 μL,0.62 mmol). After 5 min a solution of methyl 5-(1-hydroxyethyl)-benzo[b]thiophene-2-carboxylate (60.8 mg, 0.26 mmol) in CH$_2$Cl$_2$ (3 mL) was added via cannula. After an additional 20 min Et$_3$N (215 μL,1.5 mmol) was added. The reaction mixture was warmed to 25° C. over 30 min, then diluted with CHCl$_3$ and washed with saturated aqueous NaHCO$_3$ solution. The organic layer was dried (MgSO$_4$), filtered, and evaporated to dryness to afford methyl 5-acetylbenzo[b]thiophene-2-carboxylate (61.7 mg, quantitative yield) as a slightly yellow solid. This ketone was reacted with methyltriphenylphosphonium iodide and KOBu$^t$ in the usual fashion to give methyl 5-(1-methylethenyl)-benzo[b]thiophene-2-carboxylate (37.3 mg, 61%) as a white solid. To this material was added a solution of Me$_3$Al/NH$_4$Cl (0.24M, 3.4 mL). The mixture was heated at 115° C. under N$_2$ for 16 h to afford, after workup and preparative tlc (20% MeOH/CHCl$_3$), 5-(1-methylethyl)benzo[b]thiophene-2-carboxamidine hydrochloride (11.2 mg, 28%), in ca. 83% purity, as a gray solid: $^1$H NMR (CD$_3$OD) δ 8.29 (1H,s), 8.14 (1H,s), 8.03 (1H,d,J=8.0 Hz), 7.84 (1H,d,J=8.0 Hz), 5.57 (1H,s), 5.26 (1H,s) 4.97 (4H,br s), 2.29 (3H,s).

Compound 116

5-(E/Z-Prop-1-enyl)benzo[b]thiophene-2-carboxamidine hydrochloride

Methyl 5-formylbenzo[b]thiophene-2-carboxylate (103.7 mg, 0.47 mmol, Compound 122) was reacted with ethyltriphenylphosphonium iodide and KOBu$^t$ in the usual fashion to give methyl 5(E/Z-prop-1-enyl)-benzo[b]thiophene-2-carboxylate (71 mg, 65%) as a white solid. This ester was amidinated with 5 equiv of Me$_3$Al/NH$_4$Cl in refluxing xylenes for 3 h to afford, after workup and preparative tlc (20% MeOH/CHCl$_3$), 5-(E/Z-propenyl)benzo[b]thiophene-2-carboxamidine hydrochloride heptahydrate (76.6 mg, 82%, E/Z=1:3) as an orange solid: $^1$H NMR (CD$_3$OD) E-isomer δ 8.23 (1H,s), 7.98 (1H,d,J=8.9 Hz), 7.97 (1H,s), 6.61 (1H,d,J=17.0 Hz), 6.48 (1H,dq,J$_d$=17.0 Hz,J$_q$=5.3 Hz), 4.95 (4H,br s), 1.97 (3H,d,J=5.2 Hz). Z-isomer δ 8.27 (1H,s), 8.04 (1H,d,J=8.4 Hz), 7.98 (1H,d,J=9.0 Hz), 7.96 (1H,s), 7.59 (1H,d,J=8.4 Hz), 6.63 (1H,d,J=9.6 Hz), 5.98 (1H,dq,J$_d$=9.6 Hz,J$_q$=6.0 Hz), 4.95 (18H,br s), 1.98 (3H,d,J=6.0 Hz).

Compound 117

5-(E/Z-But-1-enyl)benzo[b]thiophene-2-carboxamidine hydrochloride

Methyl 5-formylbenzo[b]thiophene-2-carboxylate (100.4 mg, 0.46 mmol, Compound 122) was reacted with propyl triphenylphosphonium iodide and KOBu$^t$ in the usual fashion to give methyl 5(E/Z-but-1-enyl)-benzo[b]thiophene-2-carboxylate (85.9 mg, 76%) as a white solid. This ester was amidinated with 5 equiv of Me$_3$Al/NH$_4$Cl in refluxing xylenes for 3 h to afford, after workup and column chromatography (15% MeOH/CHCl$_3$), 5-(E/Z-but-1-enyl)benzo[b]thiophene-2-carboxamidine hydrochloride nonahydrate (82.6 mg, 55%, E/Z=1:5) as an orange solid: $^1$H NMR (CD$_3$OD) Z-isomer δ 8.27 (1H,s), 8.03 (1H,d,J=8.5 Hz), 7.94 (1H,s), 7.56 (1H,dd,J=8.6,1.6 Hz), 6.56 (1H,d,J=11.0 Hz), 5.98 (1H,dt,J$_d$=11.6 Hz,J$_t$=6.0 Hz), 4.96 (22H,br s), 2.43 (2H,m), 1.14 (3H,t,J=7.5 Hz).

Compound 118

5-(E/Z-2-Methylbut-1-enyl)benzo[b]thiophene-2-carboxamidine hydrochloride

Methyl 5-formylbenzo[b]thiophene-2-carboxylate (54.1 mg, 0.25 mmol, Compound 122) was reacted with but-2-yl triphenylphosphonium iodide and KOBu$^t$ in the usual fashion at 0° C. to give methyl 5(E/Z-2-methylbut-1-enyl)benzo[b]thiophene-2-carboxylate (20.6 mg, 32%) as an off white solid. This ester was amidinated with 5 equiv of Me$_3$Al/NH$_4$Cl in refluxing xylenes for 2 h to afford, after workup and column chromatography on silica gel (15% MeOH/CHCl$_3$), 5-(E/Z-2-methylbut-1-enyl)benzo[b]thiophene-2-carboxamidine hydrochloride (10.3 mg, 46%, E/Z=1:1) as an orange solid: $^1$H NMR (CD$_3$OD) E-isomer δ 8.25 (1H,s), 8.01 (1H,d,J=8.7 Hz), 7.90 (1H,s), 7.52 (1H,d,J=8.0 Hz), 6.46 (1H,s), 4.96 (4H,br s), 1.18 (3H,t,J=6.4 Hz); Z-isomer δ 8.25 1H,s), 8.01 (1H,d,J=8.7 Hz), 7.86 (1H,s), 7.49 (1H,d,J=8.0 Hz), 6.45 (1H,s), 4.95 (4H,br s), 2.33 (2H,m), 1.21 (3H,t,J=7.5 Hz).

Compound 119

5-(E/Z-3-Methylbut-1-enyl)benzo[b]thiophene-2-carboxamidine hydrochloride

Methyl 5-formylbenzo[b]thiophene-2-carboxylate (54.0 mg, 0.25 mmol, Compound 122) was reacted with 2-methylprop-1-yl triphenylphosphonium iodide and KOBu$^t$ in the usual fashion to give methyl 5(E/Z-3-methylbut-1-enyl)benzo[b]thiophene-2-carboxylate (19.6 mg, 31%) as an off white solid. This ester was amidinated with 5 equiv of Me$_3$Al/NH$_4$Cl in refluxing xylenes for 4 h to afford, after workup and column chromatography on silica gel (15% MeOH/CHCl₃), 5-(E/Z-3-methylbut-1-enyl)benzo[b]thiophene-2-carboxamidine hydrochloride (5.8 mg, 27%, E/Z=2:3) as a pale yellow film: $^1$H NMR (CD₃OD) E-isomer δ 8.24 (1H,s), 7.99–7.95 (2H,m), 7.73 (1H,d,J=8.7 Hz), 6.56 1H,d,J=15.9 Hz), 6.43 (1H,dd,J=15.9,6.9 Hz), 4.96 (4H,br s), 2.56 (1H,m), 1.18 (6H,d,J=6.8 Hz); Z-isomer δ 8.27 (1H,s), 8.04 (1H,d,J=8.0 Hz), 7.92 (1H,s), 7.56 (1H,d,J=8.0 Hz), 6.52 (1H,d,J=11.0 Hz), 5.66 (1H,t,J=10.0 Hz), 4.95 (4H,br s), 2.95 (1H,m), 1.12 (6H,d,J=6.5 Hz).

Compound 120

5-(E/Z-Hex-1-enyl)benzo[b]thiophene-2-carboxamidine hydrochloride

Methyl 5-formylbenzo[b]thiophene-2-carboxylate (54.0 mg, 0.25 mmol, Compound 122) was reacted with pentyltriphenylphosphonium iodide and KOBu$^t$ in the usual fashion to give methyl 5(E/Z-pent-1-enyl)benzo[b]thiophene-2-carboxylate (43.5 mg, 56%) as an off white solid. This ester was amidinated with 10 equiv of Me₃Al/NH₄Cl in refluxing xylenes for 3 h to afford, after workup and column chromatography on silica gel (15% MeOH/CHCl₃), 5-(E/Z-hex-1-enyl)benzo[b]thiophene-2-carboxamidine hydrochloride octahydrate (34.0 mg, 49%, E/Z=3:7) as a light orange solid: $^1$H NMR (CD₃OD) E-isomer δ 8.24 (1H,s), 7.98 (1H,d,J=7.0 Hz), 7.97 (1H,s), 7.73 (1H,d,J=8.6 Hz), 6.59 (1H,d,J=16.0 Hz), 6.47 (1H,m), 4.95 (20H,br s), 2.32 (2H,q,J=7.0 Hz), 1.58–1.42 (2H,m), 1.00 (3H,t,J=6.8 Hz); Z-isomer δ 8.27 (1H,s), 8.03 (1H,d,J=8.1 Hz), 7.95 (1H,s), 7.56 (1H,d,J=8.5 Hz), 6.61 (1H,d,J=10.6 Hz), 5.84 (1H,dt,J$_d$=10.9, J$_t$=7.4 Hz), 4.95 (20H,br s), 2.42 (2H,q,J=7.5 Hz), 1.43 (2H,m), 0.94 (3H,t,J=7.0 Hz).

Compound 121

5-(E/Z-2-Cyclopropylethenyl)benzo[b]thiophene-2-carboxamidine hydrochloride

Methyl 5-formylbenzo[b]thiophene-2-carboxylate (49.3 mg, 0.22 mmol, Compound 122) was reacted with 2-cyclopropylmethyltriphenylphosphonium iodide and KOBu$^t$ in the usual fashion to give methyl 5(E/Z-2-cyclopropylethenyl)benzo[b]thiophene-2-carboxylate (29.1 mg, 50%) as an off white solid. This ester was amidinated with 5 equiv of Me₃Al/NH₄Cl in refluxing xylenes for 1 h to afford, after workup and column chromatography on silica gel (15% MeOH/CHCl₃), 5-(E/Z-hex-1-enyl)benzo[b]thiophene-2-carboxamidine hydrochloride (13.8 mg, 44%, E/Z=1:2) as a clear film: $^1$H NMR (CD₃OD) E-isomer δ 8.22 (1H,s), 7.96 (1H,s), 7.95 (1H,d,J=7.5 Hz), 7.68 (1H,d,J=8.6 Hz), 6.65 (1H,d,J= 15.8 Hz), 5.97 (1H,dd,J=15.8,9.0 Hz), 4.96 (4H,br s), 1.66 (1H,m), 0.90 (2H,m), 0.60 (2H,m); Z-isomer δ 8.27 (1H,s), 8.09 (1H,s), 8.04 (1H,d,J=8.5 Hz), 7.71 (1H,d,J=8.0 Hz), 6.52 (1H,d,J=11.5 Hz), 5.25 (1H,t,J 10.5 Hz), 4.96 (4H,br s), 1.93 (1H,m), 0.90 (2H,m), 0.56 (2H,m).

Compound 122

5-[E-2-(4-Carboxamidinophenyl)ethenyl]benzo[b]thiophene-2-carboxamidine bis-hydrochloride Methyl 4-formylbenzo[b]thiophene-2-carboxylate was prepared in four steps; ketalisation, metalation-formylation, thiophene annulation, and ketal hydrolysis in 80%, 49%, 62% and 73% isolated yields respectively, using the procedures described in Compound 22. This was converted on a 1 mmol scale to methyl 5-(E/Z-2-(4-cyanophenyl)ethenyl)benzo[b]thiophene-2-carboxylate with 4-cyanobenzyl triphenylphosphonium bromide and KOBu$^t$, in the usual fashion, and this was isomerised to the pure E-alkene with 0.4 equiv iodine in refluxing dioxane for 30 h, followed by recrystallisation from EtOH, in overall 56% yield. This was amidinated in the normal fashion with 10 equivalents of NH₄Cl/Me₃Al. The compound precipitated when chromatography was attempted in 20% or 30% MeOH/CHCl₃. This precipitate was dissolved in water, and precipitated with dilute NaOH solution. The solid was collected, dried, dissolved in 0.05M hydrochloric acid, filtered and lyophilised to give 5-[E-2-(4-carboxamidinophenyl)ethenyl]benzo[b]thiophene-2-carboxamidine bis-hydrochloride (48.2 mg, 37%) as a bright yellow solid: $^1$H NMR (DMSO-d₆) δ 9.70 (2H,br s), 9.44 (4H,br s), 9.23 (2H,br s), 8.49 (1H,d,J=1.5 Hz), 8.26 (1H,sl br s), 8.24 (1H,d,J=8.5 Hz), 7.97 (1H,dd,J=8.5,1.5 Hz), 7.91, 7.87 (2H,2H, ABq,J=8.5 Hz), 7.68, 7.54 (2H,2H,ABq,J=16.5 Hz).

Compound 123

5-(Ethynyl)benzo[b]thiophene-2-carboxamidine hydrochloride

Methyl 4-formylbenzo[b]thiophene-2-carboxylate (Compound 122) was converted into methyl 5-(ethynyl)benzo[b]thiophene-2-carboxylate by the DAMP reagent and KOBu$^t$, as described in Compound 39, in 46% yield. Amidination in the usual fashion gave 5-(ethynyl)benzo[b]thiophene-2-carboxamidine hydrochloride (99.3 mg, 91%) as a light yellow solid: $^1$H NMR (DMSO-d₆) δ 9.64 (2H,br s), 9.35 (2H,br s), 8.37 (1H,s), 8.24 (1H,d,J=1.5 Hz), 8.23 (1H,d,J=8.5 Hz), 7.64 (1H,dd,J=8.5,1.5 Hz), 4.35 (1H,s).

Compound 124

5-Phenylbenzo[b]thiophene-2-carboxamidine hydrochloride

A solution of methyl 5-iodobenzo[b]thiophene-2-carboxylate (156.5 mg, 0.49 mmol, Compound 104), dimethyldiphenyltin (242.8 mg, 0.80 mmol), and tetrakis(triphenylphosphine)palladium (30.5 mg, 0.02 mmol) in dioxane (6 mL) was heated at 90° C. No reaction occurred after 20 h, so LiCl (ca. 50 mg) was added and the reaction mixture was heated at reflux for 19.5 h. The reaction was diluted with Et₂O, washed with water, 10% aq. NH₄OH, water (2×), brine, and the organics were dried (MgSO₄). After filtration and solvent removal, the residue was purified by chromatography (6% EtOAc/hexane) to afford methyl 5-phenylbenzo[b]thiophene-2-carboxylate (72.4 mg, 55%) as a white solid. Treatment of this ester (0.27 mmol) with 5.7 equiv Me₃Al/NH₄Cl (toluene, 110° C., 16.5 h) gave, after workup and chromatographic purification (15% MeOH/CHCl₃), 5-phenylbenzo[b]thiophene-2-carboxamidine hydrochloride (71.7 mg, 92%) as a light yellow solid: $^1$H NMR (CD₃OD) δ 8.35 (1H,s), 8.30 (1H,d,J=1.7 Hz), 8.16 (1H,d,J=8.5 Hz), 7.93 (1H,dd,J=8.5,1.9 Hz), 7.76 (2H,d,J=7.2 Hz), 7.54 (2H,t,J=7.2 Hz), 7.44 (1H,t,J=6,7 Hz), 4.94 (4H,br s).

Compound 125

5-(Pyrid-3-yl)benzo[b]thiophene-2-carboxamidine hydrochloride

A solution of methyl 5-bromobenzo[b]thiophene-2-carboxylate (366.2 mg, 1.35 mmol, Compound 103), hexamethylditin (0.33 mL, 1.51 mmol), and tetrakis(triphenylphosphine)palladium (70.1 mg, 0.06 mmol) in dioxane (8 mL) were heated under $N_2$ at 90° C. for 3 h. The reaction was cooled to room temperature, diluted with $Et_2O$, washed with water (2×), 10% aqueous $NH_4OH$ solution, saturated brine, and dried ($MgSO_4$). Filtration, solvent removal, and purification by flash chromatography (8% EtOAc/hexane) gave methyl 5-(trimethylstannyl)benzo[b]thiophene-2-carboxylate (353.1 mg, 74%) as a white solid.

A solution of methyl 5-(trimethylstannyl)benzo[b]thiophene-2-carboxylate (152.9 mg, 0.43 mmol), 3-bromopyridine (50 μl, 0.52 mmol), bis(triphenylphosphine)palladium(II) chloride (15.7 mg, 0.02 mmol), and LiCl (60.3 mg, 1.42 mmol) in DMF (5 mL) was heated under $N_2$ with stirring at 85° C. for 5.5 h. Workup and chromatography (50% EtOAc/hexane) gave methyl 5-(pyrid-3-yl)benzo[b]thiophene-2-carboxylate (28.0 mg, 24%). Treatment of this ester (0.10 mmol) with 5.2 equiv $Me_3Al/NH_4Cl$ (xylene, 130° C., 6.5 h) gave, after workup and chromatographic purification (25% $MeOH/CHCl_3$), 5-(pyrid-3-yl)benzo[b]thiophene-2-carboxamidine bis-hydrochloride 4.4 $H_2O$ (46.3, mg, 100%) as an offwhite solid: $^1H$ NMR ($CD_3OD$) δ 8.96 (1H,dd,J=1.2,1.0 Hz), 8.63 (1H,dd,J=4.9,1.5 Hz), 8.41–8.39 (2H,m), 8.29–8.26 (1H,m), 8.24 (1H,d,J=8.5 Hz), 7.97 (1H,dd,J=8.5,1,7 Hz), 7.66–7.63 (1H,m), 4.96 (14H,br s).

Compound 126

5-(Furan-2-yl)benzo[b]thiophene-2-carboxamidine hydrochloride

A solution of tri-n-butyl(furan-2-yl)tin (280.1 mg, 0.76 mmol, Compound 49), methyl 5-iodobenzo[b]thiophene-2-carboxylate (203.8 mg, 0.64 mmol, Compound 104), bis(triphenylphosphine)palladium(II) chloride (26.5 mg, 0.04 mmol), and LiCl (84.0 mg, 1.98 mmol) in DMF (6 mL) was heated at 80° C. under $N_2$ for 30 min. Workup and chromatography (7% EtOAc/hexane) gave methyl 5-(furan-2-yl)benzo[b]thiophene-2-carboxylate (118.6 mg, 72% yield). Treatment of this ester (0.46 mmol) with 5.2 equiv $Me_3Al/NH_4Cl$ (xylene, 130° C., 5 h) gave, after workup and chromatographic purification (15% $MeOH/CHCl_3$), 5-(furan-2-yl)benzo[b]thiophene-2-carboxamidine hydrochloride (91.9 mg, 72%): $^1H$ NMR ($CD_3OD$) δ 8.32 (1H,d,J=1.4 Hz), 8.25 (1H,s), 8.04 (1H,d,J=8.6 Hz), 7.93 (1H,dd,J=8.6,1.7 Hz), 7.62 (1H,dd,J=1.7,0.7 Hz), 6.92 (1H,dd,J=3.4,0.5 Hz), 6.56 (1H,dd,J=3.4,1.7 Hz), 4.67 (4H,br s).

Compound 127

5-(Thien-2-yl)benzo[b]thiophene-2-carboxamidine hydrochloride

A solution of trimethyl(thien-2-yl)tin (86.5 mg, 0.35 mmol, Compound 50), methyl 5-iodobenzo[b]thiophene-2-carboxylate (84.4 mg, 0.26 mmol, Compound 104), bis(triphenylphosphine)-palladium(II) chloride (12.8 mg, 0.02 mmol), and LiCl (38.1 mg, 0.89 mmol) in DMF (4 mL) was heated under $N_2$ at 80° C. for 45 min. Workup and chromatography (10% EtOAc/hexane) gave methyl 5-(thien-2-yl)benzo[b]thiophene-2-carboxylate (60.0 mg, 82%). Treatment of this ester (0.22 mmol) with 5.0 equiv $Me_3Al/NH_4Cl$ (xylene, 130° C., 3 hr) gave, after workup and chromatographic purification (15% $MeOH/CHCl_3$), 4-(thien-2-yl)benzo[b]thiophene-2-carboxamidine hydrochloride 2.5 $H_2O$ (73.3 mg, 100%) as a light yellow solid: $^1H$ NMR ($CD_3OD$) δ 8.32 (1H,d,J=1.7 Hz), 8.30 (1H,s), 8.20 (1H,d,J=8.8 Hz), 7.95 (1H,dd,J=8.7,1.7 Hz), 7.58 (1H,dd,J=3.6,0.9 Hz), 7.50 (1H,dd,J=5.1,0.9 Hz), 7.19 (1H,dd,J=5.1,3.6 Hz), 4.95 (9H,br s).

Compound 128

5-(Benzo[b]thien-2-yl)benzo[b]thiophene-2-carboxamidine hydrochloride (Benzo[b]thien-2-yl)trimethyltin was prepared in 98% yield from benzo[b]thiophene (3.75 mmol) by treatment with n-BuLi (1.06 equiv, THF, −78° C., 1.5 h) followed by addition of trimethyltin chloride (1.04 equiv, −78° C. to 25° C.). A solution of this stannane (140.1 mg, 0.47 mmol), methyl 5-bromobenzo[b]thiophene-2-carboxylate (102.8 mg, 0.38 mmol, Compound 103), bis(triphenylphosphine)palladium II) chloride (16.0 mg, 0.02 mmol), and LiCl (51.7 mg, 1.22 mmol) in DMF (5 mL) was heated at 80° C. under $N_2$ for 2.3 h. Workup and recrystallization from $CHCl_3$ gave methyl 5-(benzo[b]thien-2-yl)benzo[b]thiophene-2-carboxylate (78.6 mg, 64%). Treatment of this ester (0.24 mmol) with 5.0 equiv $Me_3Al/NH_4Cl$ (xylene, 130° C., 22.5 h) gave, after workup and chromatographic purification (15% $MeOH/CHCl_3$), 5-(benzo[b]thien-2-yl)benzo[b]thiophene-2-carboxamidine hydrochloride (36.8 mg, 44%) as a yellow solid: $^1H$ NMR ($CD_3OD$) δ 8.28 (1H,s), 8.23 (1H,s), 8.03 (1H,d,J=8.6 Hz), 7.93 (1H,dd,J=8.6,1.5 Hz), 7.84 (1H,d,J=7.3 Hz), 7.79 (1H,dd,J=7.8,1.3 Hz), 7.37–7.30 (2H,m), 4.94 (4H,br s).

COMPOUND 129

5-(Trifluoromethyl)benzo[b]thiophene-2-carboxamidine hydrochloride

4-Fluoro-1-trifluoromethylbenzene was formylated in 77% yield by treatment with LDA and DMF in THF at −78° C. in the usual fashion, and was cyclized to the corresponding benzothiophene with methyl thioglycollate and NaH in 63% yield in the usual fashion. Amidination in the usual fashion gave 5-(trifluoromethyl)benzo[b]thiophene-2-carboxamidine hydrochloride (189.5 mg, 68%) as a pale yellow solid: $^1H$ NMR (DMSO-$d_6$) δ 9.71, 9.38 (2H,2H,2 br s), 8.55 (1H,sl br s), 8.49 (1H,d,J=2 Hz), 8.48 (1H,d,J=8.9 Hz), 7.91 (1H,dd,J=8.9,2 Hz).

Compound 130

5-Formylbenzo[b]thiophene-2-carboxamidine hydrochloride

To methyl 5-formylbenzo[b]thiophene-2-carboxylate (100.2 mg, 0.45 mmol, Compound 122) was added $Me_3Al/NH_4Cl$ solution (0.86M, 5.1 mL) in xylenes and xylenes (5 mL). The mixture was heated at 120° C. for 2.5 h to afford, after workup and preparative tlc (20% $MeOH/CHCl_3$), 5-formylbenzo[b]thiophene-2-carboxamidine hydrochloride (28.7 mg, 28%) as a beige solid: $^1H$ NMR (DMSO-$d_6$) δ 10.14 (1H,s), 9.67 (2H,br s), 9.33 (2H,br s), 8.67 (1H,sl br s), 8.56 (1H,s), 8.41 (1H,d,J=8.9 Hz), 8.05 (1H,d,J=8.5 Hz).

Compound 131

5-(Hydroxymethyl)benzo[b]thiophene-2-carboxamidine hydrochloride

To a solution of methyl 5-formylbenzothiophene-2-carboxylate (100.3 mg, 0.46 mmol, Compound 122) in THF (5 mL) stirred under $N_2$ at 0° C. was added $BH_3$.THF (1M, 460 μL). The reaction was quenched with excess MeOH after 20 min, washed with saturated aqueous $NaHCO_3$ solution, and then extracted twice with EtOAc. The organic layer was dried ($MgSO_4$), filtered, and evaporated to dryness to afford methyl 5-(hydroxymethyl)benzo[b]thiophene-2-carboxylate (102.6 mg, 100%) as a white solid.

To this ester (102.6 mg, 0.46 mmol) was added a solution of $Me_3Al/NH_4Cl$ (0.86M, 4.3 mL) and additional xylenes (4 mL). The mixture was heated at 120° C. for 3 h to afford, after workup and preparative tlc (15% MeOH/$CHCl_3$), 5-hydroxymethylbenzo[b]thiophene-2-carboxamidine hydrochloride pentahydrate (60.0 mg, 39%) as a light beige solid: $^1$H NMR (DMSO-$d_6$) δ 9.54 (2H,br s), 9.25 (2H,br s), 8.38 (1H,sl br s), 8.13 (1H,d,J=8.7 Hz), 7.98 (1H,s), 7.55 (1H,d,J=7.9 Hz), 5.43 (1H,t,J=5.0 Hz), 4.66 (2H,d,J=5.0 Hz).

Compound 201

4-(Methylthio)-5-ethenylbenzo[b]thiophene-2-carboxamidine hydrochloride

2-Chloro-6-fluorobenzaldehyde was ketalised with ethane-1,2-diol to form 2-(2-chloro-6-fluorophenyl)-1,3-dioxolane in 86% yield, as described in Compound 22. Formylation with n-butyl lithium followed by DMF in THF at −78° C. under the usual conditions gave 4-chloro-3-(1,3-dioxolan-2-yl)-2-fluorobenzaldehyde in 94% crude yield, with less than 5% of any regioisomer. Reaction of this aldehyde with sodium methanethiolate in DMSO as described in Compound 58, followed by recrystallisation from toluene/hexanes at −20° C., gave 4-chloro-3-(1,3-dioxolan-2-yl)-2-methylthiobenzaldehyde in 40% yield. This aldehyde was reacted with methyl triphenylphosphonium bromide and KOBu$^t$ in THF at 0° C. in the usual manner, to give 4-chloro-3-(1,3-dioxolan-2-yl)-2-methylthiostyrene in 94% yield. The ketal was removed by treatment with TFA/water/acetonitrile/acetone at 50° C. for 2 h, followed by preparative tlc, eluting with 10% EtOAc /hexanes, to give 6-chloro-3-ethenyl-2-methylthiobenzaldehyde in 76% yield. This was cyclised to 5-ethenyl-4-methylthiobenzo[b]thiophene carboxylic acid by treatment with two equiv of NaH and methylthioglycollate in DMSO at 60° C. for 1 h, followed by preparative tlc eluting with 15% MeOH/$CHCl_3$, in 65% yield. The acid was converted into the corresponding acid chloride by reaction with 10 equiv of oxalyl chloride at 0° C. in $CH_2Cl_2$ containing excess 2-methylbut-2-ene, and the acid chloride was amidinated in the usual fashion to give 4-(methylthio)-5-ethenylbenzo[b]thiophene-2-carboxamidine hydrochloride (17.5 mg, 70% pure, 15%) as a yellow glass: $^1$H NMR (DMSO-$d_6$) δ 9.63,9.23 (2H, 2H, 2 br s), 8.66 (1H,s), 8.21 (1H,d,J=8.8 Hz), 7.94 (1H,d,J=8.6 Hz), 7.51 (1H,dd,J=11.3,17.4 Hz), 6.00 (1H,d,J=17.4 Hz), 5.54 (1H,d,J=11.3 Hz), 2.40 (3H,s).

Compound 202

4-Bromo-5-methylbenzo[b]thiophene-2-carboxamidine hydrochloride

2-Bromo-4-fluorotoluene was formylated with LDA and DMF in THF at −78° C. in the usual fashion to give 2-bromo-6-fluoro-3-methylbenzaldehyde in quantitative yield. Upon cyclisation with NaH and methyl thioglycollate under the usual conditions the aldehyde gave a 2:1 mixture of the desired compound, methyl 4-bromo-5-methylbenzo[b]thiophene-2-carboxylate, and the product derived from initial bromine displacement, methyl 4-fluoro-7-methylbenzo[b]thiophene-2-carboxylate. Two recrystallisations from hexanes gave the desired ester pure in 8% yield. Amidination under the usual conditions gave 4-bromo-5-methylbenzo[b]thiophene-2-carboxamidine hydrochloride dodecahydrate (116.0 mg, 79%) as a white solid: $^1$H NMR ($CD_3OD$) δ 8.40 (1H,d,J=0.7 Hz), 7.92 (1H,d,J=8.3 Hz), 7.53 (1H,d,J=8.3 Hz), 4.90 (28H,br s), 2.56 (3H,s).

Compound 203

4-Chloro-5-iodobenzo[b]thiophene-2-carboxamidine hydrochloride

2-Chloro-4-fluoroiodobenzene was formylated with LDA and DMF in THF at −78° C. under the usual conditions to give 2-chloro-6-fluoro-3-iodobenzene in 97% yield. Cyclisation with NaH and methyl thioglycollate under the usual conditions gave methyl 4-chloro-5-iodobenzo[b]thiophene-2-carboxylate in 74% yield. Amidination under the usual conditions gave 4-chloro-5-iodobenzo[b]thiophene-2-carboxamidine hydrochloride trihydrate (213 mg, quant) as a yellow solid: $^1$H NMR ($CD_3OD$) δ 8.41 (1H,d,J=0.7 Hz), 8.03 (1H,d,J=8.6 Hz), 7.77 (1H,dd,J=8.3,0.7 Hz), 4.90 (10H,br s).

Compound 204

4-Bromo-5-methoxybenzo[b]thiophene-2-carboxamidine hydrochloride

Bromine (3.2 g, 20 mmol) was added dropwise to a solution of 4-fluoroanisole (2.52 g, 20 mmol) in $CH_2Cl_2$ (20 ml) stirred under $N_2$ at 25° C. After 30 minutes solid $NaHCO_3$ was added cautiously with vigorous stirring until gas evolution died down. The mixture was then diluted with $CHCl_3$ (30 mL), washed with water (2×25 mL) and saturated brine (30 mL), and dried ($Na_2SO_4$). The solvent was removed under reduced pressure to give a quantitative yield of 2-bromo-4-fluoroanisole.

The 2-bromo-4-fluoroanisole was formylated with LDA and DMF in THF at −78° C. under the usual conditions, to give, after recrystallisation from hexanes, 2-bromo-6-fluoro-3-methoxybenzaldehyde (1.30 g, 28%) as off-white needles. Annulation of this aldehyde with NaH and methyl thioglycollate under the usual conditions, followed by preparative tlc on silica, eluting twice with 10% EtOAc in hexanes gave methyl 4-fluoro-7-methoxybenzo[b]thiophene-2-carboxylate (200.4 mg, 19%), $R_f$ 0.56, and methyl 4-bromo-5-methoxybenzo[b]thiophene-2-carboxylate (228.4 mg, 18%) $R_f$ 0.48. Methyl 4-bromo-5-methoxybenzo[b]thiophene-2-carboxylate was amidinated under the usual conditions to give 4-bromo-5-methoxybenzo[b]thiophene-2-carboxamidine hydrochloride dihydrate (271 mg, 100%) as a light yellow solid: $^1$H NMR ($CD_3OD$)

δ 8.33 (1H,d,J=0.7 Hz), 7.99 (1H,dd,J=9.0,0.7 Hz), 7.44 (1H,d,J=9.0 Hz), 4.90 (8H,br s), 3.99 (3H,s).

Compound 205

Naphtho[2,1-b]thiophene-2-carboxamidine hydrochloride

To a stirred solution of potassium toluenethiosulfonate (5.39 g, 23.8 mmol) in CH₃CN (50 mL) under N₂ was added benzyl bromide (3.88 g, 2.7 mL, 22.7 mmol). After 20 h the mixture was poured onto water and extracted into Et₂O. The organic layer was dried (MgSO₄), filtered, and concentrated under reduced pressure to give benzyl toluenethiosulfonate (6.50 g, 98%) as a clear, colorless syrup.

To a solution a solution of N,N,N'-trimethylethylenediamine (204.4 mg, 254 μL, 2.0 mmol) in THF (8 mL) stirred under N₂ at −78° C. was added n-BuLi (2.5M, 720 μL, 1.8 mmol). After 5 min a solution of 1-naphthaldehyde (249.9 mg, 220 μL, 1.6 mmol) in THF (2 mL) was added dropwise via cannula. After an additional 10 min, s-BuLi (1.2M, 2.5 mL, 3.0 mmol) was added and the reaction was kept at −18° C. for 3.25 h. The reaction was again cooled to −78° C. and a solution of benzyl toluenethiosulfonate (1.67 g, 6.0 mmol) in THF (4 mL) was added dropwise via cannula. The reaction was allowed to warm to 25° C. over 16 h, and was then was poured onto vigorously stirring saturated brine and was extracted with Et₂O. The organic layer was dried (MgSO₄), filtered and concentrated under reduced pressure. The crude brown product was purified by column chromatography on silica gel (5% EtOAc/hexanes), followed by Kugelrohr distillation to give 2-benzylthio-1-naphthaldehyde (76.0 mg, 38%) as a yellow solid, containing a minor amount of 1-naphthaldehyde.

This thioether (51.0 mg, 0.15 mmol) was refluxed in neat methyl bromoacetate (1.5 mL) under N₂ for 3.25 h, cooled to 25° C., diluted with Et₂O, and washed with 10% aqueous Na₂S₂O₃ solution. The organic layer was dried (MgSO₄), filtered, and evaporated rigorously under reduced pressure to remove excess bromoacetate. Purification by preparative tlc (1% MeOH/CHCl₃) afforded the S-arylthioglycolate (45.5 mg, 95%), containing a small amount of methyl bromoacetate.

A mixture of the thioglycolate (45.5 mg, 0.17 mmol) and Et₃N (73 μL, 0.52 mmol) in DMSO (1 mL) was heated under N₂ to 60° C. for 1.5 h followed by addition of more Et₃N (37 μL, 0.26 mmol). After an additional 1.5 h the reaction was cooled to 25° C., diluted with Et₂O, and washed with dilute HCl (0.2M, 5 mL). The organic layer was dried (MgSO₄), filtered, and concentrated under reduced pressure. The resultant brown oil was purified by prep tlc (10% EtOAc/hexanes) to give methyl naphtho[2,1-b]thiophene-2-carboxylate (10.2 mg, 24%) as a yellow solid.

To a solution of this ester (10.2 mg, 0.04 mmol) in xylenes (2 mL) was added Me₃Al/NH₄Cl solution (0.5M, 840 μL) in xylenes and the mixture was refluxed under N₂ for 1 h followed by addition of more Me₃Al/NH₄Cl (840 μL, 10 equiv). An additional 1 h of reflux followed by normal workup and preparative tlc (20% MeOH/CHCl₃) gave naphtho[2,1-b]thiophene-2-carboxamidine hydrochloride (4.6 mg, 42%) as a white film: ¹H NMR (CD₃OD) δ 9.03 (1H,s), 8.53 (1H,d,J=8.2 Hz), 8.10 (1H,d,J=8.3 Hz), 8.06 (2H,s), 7.87 (1H,t,J=7.6 Hz), 7.70 (1H,t,J=7.6 Hz), 4.96 (4H,br s).

Compound 206

5-(Hydroxymethyl)thieno[4,5-b]benzo[b]thiophene-2-carboxamidine hydrochloride

4-Chloro-3-(1,3-dioxolan-2-yl)-2-fluorobenzaldehyde (4.00 g, 17.3 mmol, Compound 201), methyl thioglycollate (1.52 mL, 17 mmol) and Et₃N (3.75 g, 37 mmol) were heated to 60° C. in DMSO (20 mL), stirred under under N₂ for 100 min. The reaction was poured slowly onto stirred ice-water (250 mL), and after 15 min the congealed precipitate was isolated by Buchner filtration and recrystallised from MeOH at 0° C. to give methyl 6-chloro-7-(1,3-dioxolan-2-yl)benzo[b]thiophene-2-carboxylate (2.44 g, 47%) as light yellow crystals.

LiAlH₄ (56.7 mg, 1.5 mmol) was added in one portion to a solution of methyl 6-chloro-7-(1,3-dioxolan-2-yl)benzo[b]thiophene-2-carboxylate (598 mg, 2.0 mmol) in ether (10 mL) stirred under N₂ at 0° C. After 15 min the reaction was allowed to warm up to 25° C., and after 90 min further LiAlH₄, (35.2 mg, 1 mmol) was added. After a further 1 h, the reaction mixture was quenched by the cautious, sequential, dropwise addition of water (0.1 mL), and dilute aqueous NaOH solution (1M, 0.25 mL). When gas evolution ceased, the slurry was Buchner filtered, and the solvent was removed from the filtrate under reduced pressure to give 6-chloro-7-(1,3-dioxolan-2-yl)-2-(hydroxymethyl)benzo[b]thiophene (526.6 mg, 97%) as a white waxy solid.

A solution of 6-chloro-7-(1,3-dioxolan-2-yl)-2-(hydroxymethyl)benzo[b]thiophene (525.6 mg, 1.94 mmol) and TFA (5 drops) in CH₃CN/acetone/water (4.5, 2.5, 0.5 mL) was stirred under N₂ at 25° C. for 4.5 h. Further TFA (10 drops) was added, and the mixture soon precipitated. After a further 5 h, the reaction mixture was cooled to −20° C. overnight, and the solid was collected by Buchner filtration, rinsed with aqueous CH₃CN and air dried to give 6-chloro-7-formyl-2-(hydroxymethyl) benzo[b]thiophene (335.4 mg, 76%) as a matted, white crystalline solid.

A mixture of 6-chloro-7-formyl-2-(hydroxymethyl)-benzo[b]thiophene (332.6 mg, 1.47 mmol), Et₃N (305 mg, 3 mmol), and methyl thioglycollate (0.14 mL, 1.55 mmol) in DMSO was heated to 80° C. under N₂ with stirring. After 8 h, further methyl thioglycollate (0.07 ml, 0.8 mmol) was added, and after a further 14 h the reaction mixture was poured onto vigorously stirred ice-water (50 mL), and after 20 min, the solids were collected by Buchner filtration and recrystallised from MeOH at 0° C. to give methyl 5-(hydroxymethyl)-thieno[4,5-b]benzo[b]thiophene-2-carboxylate (117.8 mg, 29%) as a light orange-brown crystalline solid.

Amidination of this compound (27.9 mg, 0.1 mmol) under the usual conditions followed by preparative tlc gave 5-(hydroxymethyl)thieno[4,5-b]benzo[b]thiophene-2-carboxamidine hydrochloride (10.2 mg, 34%) as a light yellow glass: ¹H NMR (CD₃OD) δ 8.50 (1H,s), 7.94 (2H,s), 7.43 (1H,s), 4.92 (2H,s), 4.90 (6H, br s).

Compound 207

5-(Methoxymethyl)thieno[4,5-b]benzo[b]thiophene-2-carboxamidine hydrochloride

Methyl 5-(hydroxymethyl)thieno[4,5-b]benzo[b]thiophene-2-carboxylate (27.9 mg, 0.1 mmol, Compound 206), was O-methylated with NaH and iodomethane in DMF in 55% yield. This ether was then amidinated under the usual conditions to give 5-(methoxymethyl)- thieno[4,5-b]benzo[b]thiophene-2-carboxamidine hydrochloride (10.6 mg, 62%) as a yellow glass: $^1$H NMR (CD$_3$OD) δ 8.49 (1H,s), 7.94 (2H,s), 7.47 (1H,d,J=0.7 Hz), 4.90 (5H,br s), 4.79 (2H,s), 3.44 (3H,s).

Compound 208

5-(Prop-2-en-1-yloxymethyl)thieno[4,5-b]benzo[b]thiophene-2-carboxamidine hydrochloride Methyl 5-(hydroxymethyl)thieno[4,5-b]benzo[b]thiophene-2-carboxylate (27.9 mg, 0.1 mmol, Compound 206), was O-allylated with NaH and 3-iodoprop-1-ene in DMF in 77% yield. This ether was then amidinated under the usual conditions to give 5-(prop-2-en-1-yloxymethyl)thieno[4,5-b]benzo[b]thiophene-2-carboxamidine hydrochloride (16.8 mg,64%) as a yellow glass: $^1$H NMR (CD$_3$OD) δ 8.49 (1H,d,J=0.9 Hz), 7.95 (2H,sl br s), 7.47 (1H,t,J=0.8 Hz), 5.96 (1H,m), 5.34 (1H,br d,J=17.2 Hz), 5.22 (1H,br d,J=10.3 Hz), 4.91 (6H,br s), 4.85 (2H,d,J=0.8 Hz), 4.11 (2H,br d,J=5.5 Hz).

Compound 209

5-[E-2-(4-Carboxamidinophenyl)ethenyl]thieno[4,5-b]benzo[b]thiophene-2-carboxamidine bis-hydrochloride Methyl 5-hydroxymethylthieno[4,5-b]benzo[b]thiophene-2-carboxylate (154.1 mg, 0.55 mmol, Compound 206) was converted into the bromide by adding a solution it in THF (5 mL) to a mixture of CBr$_4$ (367.2 mg, 1.1 mmol), and PPh$_3$ (290.4 mg, 1.1 mmol) in THF (5 mL) which had been stirring under N$_2$ for 45 min. After 20 min only a fraction of the starting material had converted so additional CBr$_4$ (369.3 mg, 1.1 mmol) and PPh$_3$ (290.6 mg, 1.1 mmol) in THF (5 mL) were added. After 40 min the reaction mixture was poured onto water and extracted with EtOAc. The organic layer was washed with saturated brine then dried (MgSO$_4$), filtered, and evaporated to dryness to give a light brown solid. Flash chromatography (45:5:1 hexanes/CHCl$_3$/EtOAc followed by 20:2:1 hexanes/CHCl$_3$/EtOAc) afforded methyl 5-(bromomethyl)thieno[4,5-b]benzo[b]thiophene-2-carboxylate (117.3 mg, 69%) as a white solid. This bromide was converted into the corresponding phosphonium salt (167.0 mg, 74%) by heating it with PPh$_3$ (146.7 mg, 0.56 mmol) in toluene (7 mL) at 80° C. under N$_2$ for 17.5 h.

To a suspension of the phosphonium bromide (167.0 mg, 0.28 mmol) stirring at 0° C. under N$_2$ was added a solution of potassium tert-butoxide (0.54M, 490 μL) in THF. After 20 min the mixture was cooled to −78° C. and a solution of 4-cyanobenzaldehyde (33.0 mg, 0.25 mmol) in THF (2 mL) was added via cannula. The mixture was allowed to warm to 25° C. over 1.75 h then poured onto saturated NaHCO$_3$ solution and extracted with EtOAc. A precipitate which was soluble in neither the organic nor the aqueous phase was isolated by filtration the washed with water. $^1$H NMR (CD$_3$OD) showed this to be pure E-isomer while evaporation of the organic phase produced a mixture of Z-isomer and triphenylphosphine oxide. The pure 5-[E-2-(4-cyanophenyl)ethenyl]thieno[4,5-b]thiphene-2-carboxylate (18.4 mg, 19%) was amidinated by heating to 145° C. for 4.5 h with 10 equiv. of NH$_4$Cl/Me$_3$Al. Crude material obtained after the usual workup was chromatographed (60:22:2:4 CHCl$_3$/CH$_3$OH/H$_2$O/AcOH) then treated with aqueous HCl (1M, 0.5 mL), and evaporated to dryness. This material was dissolved in water, and was treated with aqueous NaOH (0.2M) until a pH of 14 was reached. The precipitate was filtered, washed with water and redissolved by addition of aqueous HCl (1M) until a pH of 1 was reached. Removal of water under reduced pressure provided 5-[2-(4-carboxamidinophenyl)ethenyl]-thieno[4,5-b]benzo[b]thiophene-2-carboxamidine dihyrochloride (3.6 mg, 18%) as an intensely yellow solid: $^1$H NMR (CD$_3$OD) δ 8.59 (1H,s), 8.02 (2H,sl br s), 7.89 (1H,d,J=16.2 Hz), 7.73 (1H,s), 7.26 (1H,d,J=16.2 Hz), 4.96 (4H,v br s).

Compound 301

6-Iodobenzo[b]thiophene-2-carboxamidine hydrochloride

3-Fluoroiodobenzene was lithiated with LDA in THF at −78° C. in the usual manner and was reacted with chlorotrimethylsilane to give, after the usual workup and vacuum distillation at 158°-68° C./55 mm Hg, (6-fluoro-2-iodophenyl)trimethylsilane (78%) as a pale yellow oil.

(6-Fluoro-2-iodophenyl)trimethylsilane was formylated in the usual manner with 1.25 equiv of LiTMP and DMF in THF at −78° C. to give 2-fluoro-4-iodo-3-trimethylsilylbenzaldehyde in 81% yield. This was annulated in the usual fashion with NaH and methyl thioiglycollate to give about a 2:1 mixture of silylated and desilylated benzophiophenes. Refluxing of this mixture in 33% TFA in CHCl$_3$ for 9 h, effected desilylation to give after preparative tlc purification methyl 6-iodobenzo[b]thiophene-2-carboxylate in 32% yield. This was amidinated in the usual fashion to give 6-iodobenzo[b]thiophene-2-carboxamidine hydrochloride 0.8 MeOH (112.8 mg, 88%) as a light yellow solid: $^1$H NMR (DMSO-d$_6$) δ 9.60 (2H,br s), 9.30 (2H,br s), 8.70 (1H,s), 8.36 (1H,d,J=2.8 Hz), 7.86 (1H,d,J=8.3 Hz), 7.84 (1H,dd,J=8.3 1.5 Hz).

Compound 302

7-Iodobenzo[b]thiophene-2-carboxamidine hydrochloride

2-Fluoroiodobenzene was formylated with LDA and DMF in THF at −78° C. in the usual manner to give rather impure 2-fluoro-3-iodobenzaldehyde in approximately 50% yield (corrected for recovered starting material). This compound was annulated under the normal conditions with NaH and methyl thioglycollate to give somewhat impure methyl 7-iodobenzo[b]thiophene-2-carboxylate in 76% uncorrected yield. A sample of this was amidinated under the usual conditions, to give, after flash chromatography (10 then 20% CH$_3$OH/CHCl$_3$), 7-iodobenzo[b]thiophene-2-carboxamidine hydrochloride (235 mg, 69%) as a pale yellow solid: $^1$H NMR (DMSO-d$_6$) δ 9.63 (4H,br s), 8.75 (1H,s), 8.12 (1H,d,J=7.9 Hz), 7.98 (1H,d,J=7.6 Hz), 7.33 (1H,t,J=7.7 Hz).

Compound 303

6-Methylbenzo[b]thiophene-2-carboxamidine hydrochloride

3-Fluorotoluene was formylated with s-butyl lithium/TMEDA followed by DMF in THF at −78° C. in the usual fashion to give a mixture of 2-fluoro-4-methylbenzaldehyde (64%) and 2-fluoro-6-methylbenzaldehyde (18%). This mixture was partially separated by chromatography on silica gel, eluting with 2% EtOAc/hexanes, and the readily autooxidisable product was annulated with NaH and methyl thioglycollate in the usual manner to give methyl 6-methylbenzo[b]thiophene-2-carboxylate in 9% yield after recrystallisation from hexanes. This was amidinated under the usual conditions to give 6-methylbenzo[b]thiophene-2-carboxamidine hydrochloride (20.9 mg, 57%) as a white solid: $^1$H NMR (DMSO-d$_6$) δ 9.51 (2H,br s), 9.21 (2H,br s), 8.36 (1H,s), 7.99 (1H,sl br s), 7.96 (1H,d,J=8.2 Hz), 7.38 (1H,d,J=8.2,<1 Hz), 2.48 (3H,s).

Compound 304

3-Methylbenzo[b]thiophene-2-carboxamidine hydrochloride

2-Fluoroacetophenone was annulated with NaH and methyl thioglycollate under the usual conditions to give methyl 3-methylbenzo[b]thiophene-2-carboxylate in 27% yield. Amidination of this ester under the usual conditions gave 3-methylbenzo[b]thiophene-2-carboxamidine hydrochloride (102.9 mg, 91%) as a light yellow solid: $^1$H NMR (DMSO-d$_6$) δ 9.61 (4H,br s), 8.36 (1H,s), 8.13 (1H,dd,J=6.8,1.5 Hz), 8.00 (1H,dd,J=7.1,1.7 Hz), 7.6–7.52 (2H,m), 2.58 (3H,s).

Compound 305

3-Hydroxybenzo[b]thiophene-2-carboxamidine hydrochloride

Methyl thioglycollate (0.19 mL, 2.1 mmol) was added dropwise over 5 min to a suspension of hexane-washed NaH (60% oil suspension, 92.7 mg, 2.3 mmol) in DMSO (5 mL), stirred under N$_2$ at 20° C. After 15 min, methyl 2-fluorobenzoate (307.2 mg, 2.0 mmol) was added, and the mixture was stirred at 25° C. for 4 h, and for 30 min at 70° C. On cooling the yellow slurry was poured onto water (40 mL), and the precipitate was collected by Buchner filtration, rinsed with water (20 mL), and air dried to give methyl 3-hydroxybenzo[b]thiophene-2-carboxylate (131.2 mg, 32%) as a pale, pink-brown solid. This was amidinated with 5 equiv of Me$_3$Al/NH$_4$Cl in refluxing toluene for 6 h, and the product was purified by preparative tlc (20% MeOH/CHCl$_3$), to give 3-hydroxybenzo[b]thiophene-2-carboxamidine hydrochloride (12.0 mg, 25%) as a yellow glass: $^1$H NMR (DMSO-d$_6$) δ 10.3 (1H,br s), 7.75 (1H,d,J=7.4 Hz), 7.73 (1H,d,J=7.8 Hz), 7.47 (1H,sl br t, J=7.5 Hz), 7.30 (1H,t,J=7.4 Hz), 7.4–6.8 (4H,br s).

Compound 306

3-Aminobenzo[b]thiophene-2-carboxamidine hydrochloride

A solution of 2-fluorobenzonitrile (243.8 mg, 2.0 mmol), methyl thioglycollate (0.19 mL, 2.1 mmol) and Et$_3$N (405.7 mg, 4.0 mmol) in DMSO (2 mL) was heated to 80° C. with stirring under N$_2$ for 2.5 h. The reaction mixture was poured onto stirred ice-water, and the residual solid was collected by Buchner filtration rinsed with water and air dried. The solid was dissolved in THF (5 mL) stirred under N$_2$ at 25° C., and NaH (60% oil suspension, 0.07 g, 1.75 mmol) was added (gas evolution). After 10 min the reaction mixture was quenched with acetic acid (0.5 mL), poured onto water (10 mL), and extracted with EtOAc (2×10 mL). The combined extracts were rinsed with water (2×10 mL), saturated brine (10 mL) and dried (MgSO$_4$). The solvent was removed under reduced pressure, and the residue was purified by preparative tlc (20% EtOAc/hexanes). The major fluorescent band R$_f$ 0.37 was extracted with ether, and the solvent was removed under reduced pressure to give methyl 3-aminobenzo[b]thiophene-2-carboxylate (0.18 g, 43%) as a light yellow crystalline solid. This was amidinated with 10 equiv of AlMe$_3$/NH$_4$Cl in refluxing toluene for 30 h to give, after the normal workup and preparative tlc purification (25% MeOH/CHCl$_3$), 3-aminobenzo[b]thiophene-2-carboxamidine hydrochloride (32.1 mg, 16%) as a yellow glass: $^1$H NMR (CD$_3$OD) δ 8.03 (1H,sl br d,J=8.3 Hz), 7.80 (1H,sl br d,J=8.1 Hz), 7.55 (1H,sl br t,J=7.8 Hz), 7.45 (1H,sl br t,J=7.8 Hz), 4.91 (6H,br s).

Compound 307

7-[(Benzo-1,3-dioxolan-5-yl)ethynyl]benzo[b]thiophene-2-carboxamidine hydrochloride A slurry of methyl 7-iodobenzo[b][thiophene-2-carboxylate (168.4 mg, 0.53 mmol, Compound 302), 5-ethynylbenzo-1,3-dioxolane (90.0 mg, 0.61 mmol, Compound 77), bis(triphenylphosphine)palladium(II) chloride (8.8 mg, 0.01 mmol), and CuI (2.1 mg, 0.01 mmol) in Et$_3$N (3 mL) was stirred under N$_2$ at 25° C. for 24 h. Workup and purification by flash chromatography (25% EtOAc/hexane) afforded the desired product contaminated with several impurities. Recrystallization of this material from hexane/EtOAc afforded methyl 7-[(benzo-1,3-dioxolan-5-yl)ethynyl]benzo[b]thiophene-2-carboxylate (123.9 mg, 70%) as a light yellow solid. Treatment of this ester (0.36 mmol) with 5.0 equiv of Me$_3$Al/NH$_4$Cl (toluene, 130° C., 5.2 h) gave, after workup and chromatographic purification (15% MeOH/CHCl$_3$), 7-[(benzo-1,3-dioxolan-5-yl)ethynyl]-benzo[b]thiophene-2-carboxamidine hydrochloride (92.7 mg, 72%) as a bright yellow solid: $^1$H NMR (CD$_3$OD) δ 8.28 (1H,s), 7.97 (1H,d,J=8.0 Hz), 7.63 (1H,d,J=7.2 Hz), 7.50 (1H,t,J=7.7 Hz), 7.10 (1H,d,J=7.9 Hz), 6.99 (1H,s), 6.84 (1H,d,J=8.0 Hz), 6.00 (2H,s), 5.00 (4H,v br s).

Compound 308

4-Fluoro-6-bromobenzo[b]thiophene-2-carboxamidine hydrochloride

1-Bromo-3,5-difluorobenzene was formylated with LDA and DMF in THF at −78° C. under the usual conditions to give 1-bromo-3,5-difluorobenzaldehyde in 44% yield. This was annulated under the usual conditions with NaH and methyl thioglycollate to give, after flash chromatography on silica gel eluting with 2% EtOAc/hexanes, methyl 4-fluoro-6-bromobenzo[b]thiophene-2-carboxylate in 33% yield. This was amidinated under the usual conditions to give 4-fluoro-6-bromobenzo[b]thiophene-2-carboxamidine hydrochloride (51.7 mg, 57%) as a pale yellow waxy solid: $^1$H NMR (DMSO-d$_6$) δ 9.52 (4H,br s), 8.48 (1H,s), 8.45 (1H,sl br s), 7.73 (1H,d,J=9.5 Hz).

Compound 309

7-Bromo-4-methoxybenzo[b]thiophene-2-carboxamidine hydrochloride

Methyl 4-methoxybenzo[b]thiophene-2-carboxylate, (Compound 57) was brominated with one equiv of bromine in CH$_2$Cl$_2$ at 25° C. to give methyl 7-bromo-4-methoxybenzo[b]thiophene-2-carboxylate in quantitative yield. This ester was amidinated under the usual conditions to give 7-bromo-4-methoxybenzo[b]thiophene-2-carboxamidine hydrochloride hexahydrate (121.6 mg, 57%) as a pale yellow solid: $^1$H NMR (CD$_3$OD) δ 8.44 (1H,s), 7.64 (1H,d,J=8.5 Hz), 6.93 (1H,d,J=8.5 Hz), 4.90 (16H,br s), 3.96 (3H,s).

Compound 310

4-Fluoro-7-methoxybenzo[b]thiophene-2-carboxamidine hydrochloride

Methyl 4-fluoro-7-methoxybenzo[b]thiophene-2-carboxylate (Compound 204) was amidinated under the usual conditions to give 4-fluoro-7-methoxybenzo[b]thiophene-2-carboxamidine hydrochloride dihydrate (271 mg, 100%) as a pale yellow solid: $^1$H NMR (CD$_3$OD) δ 8.31 (1H,s), 7.19 (1H,dd,J=9.6, 8.6 Hz), 7.07 (1H,dd,J=8.6, 3.4 Hz), 4.89 (8H, br s), 4.02 (3H,s).

Compound 311

5,7-Dibromo-4-methoxybenzo[b]thiophene-2-carboxamidine hydrochloride

Methyl 4-methoxybenzo[b]thiophene-2-carboxylate (Compound 57) was brominated with 2.5 equiv of bromine in CH$_2$Cl$_2$ at 25° C. to give methyl 5,7-dibromo-4-methoxybenzo[b]thiophene-2-carboxylate in 42% yield after recrystallisation from hexanes. This ester was amidinated under the usual conditions to give 5,7-dibromo-4-methoxybenzo[b]thiophene-2-carboxamidine hydrochloride eicosahydrate (50.1 mg, 31%) as a yellow solid: $^1$H NMR (CD$_3$OD) δ 8.45 (1H,s), 7.95 (1H,s), 4.90 (24H, br s), 4.02 (3H,s).

Compound 312

Naphtho[1,2-b]thiophene-2-carboxamidine hydrochloride

1-Fluoronaphthalene was formylated with LDA and DMF in THF at −78° C. under the usual conditions to give 1-fluoro-2-naphthaldehyde in 80% yield. This was annulated under the usual conditions with NaH and methyl thioglycollate to give methyl naphtho[2,1-b]thiophene-2-carboxylate in 80% yield. Amidination under the usual conditions gave naphtho[1,2-b]thiophene-2-carboxamidine hydrochloride (98.8 mg, 75%) as a light yellow solid: $^1$H NMR (CD$_3$OD) δ 8.36 (1H,d, J=0.6 Hz), 8.21 (1H,br d,J=8 Hz), 8.04 (1H,br d,J=8 Hz), 7.94, 7.90 (1H,1H,ABq,J=8.8 Hz), 7.69, 7.66 (1H,1H,br ABq of d,J$_{AB}$=J$_d$=~7 Hz), 4.90 (4H,br s).

Compound 313

Naphtho[2,3-b]thiophene-2-carboxamidine hydrochloride n-Butyl lithium (2.0M in cyclohexane, 1.05 mL, 2.1 mmol) was added dropwise over 2 min to a solution of 2-naphthylthiol (160 mg, 1.0 mmol) in TMEDA (1 mL), stirred under N$_2$ at 25° C. on a water bath. After 14 h, the light brown slurry was cooled to −78° C., and THF (5 mL) was added dropwise. After 5 min DMF (0.10 mL, 1.25 mmol) was added dropwise, followed, after a further 10 min at −78° C., by a rapid addition of acetic acid (0.5 mL). Methyl bromoacetate (0.15 mL, 1.6 mmol) was added to the light yellow gel turning it pink, and the gel was shaken and allowed to warm up to 25° C., at which temperature the thick yellow paste was stirred for 1 h. The paste was decomposed with water (25 mL), and was extracted with ether (3×10 mL). The combined extracts were washed with dilute HCl (1M, 10 mL), water (2×10 mL), saturated brine (10 mL) and dried (MgSO$_4$). The solvent was removed under reduced pressure, and the residual oil was purified by preparative tlc, eluting with 20% EtOAc/hexanes. The major band, R$_f$ 0.37, was extracted with ether, and the solvent was removed under reduced pressure to give moderately clean methyl 2-(3-formylnaphthyl-2-thio)acetate (39.8 mg, 15%) as a bright yellow waxy solid.

Methyl 2-(3-formylnaphthyl-2-thio)acetate (39.8 mg, 0.15 mmol) was heated in DMSO (0.5 mL) under N$_2$ at 80° C., and triethylamine (0.10 mL) was added immediately, and after 30 min (0.1 mL) and 60 min (0.2 mL). After 5 h the volatiles were removed rigourously under reduced pressure, and the residue was purified by preparative tlc, eluting first with 10% EtOAc/hexanes, (where the major separation appeared to be caused by the insolubility of the desired tricycle in the mobile phase) then removing the band R$_f$ 0.70, followed by eluting with 50% CHCl$_3$/hexanes. The major band, R$_f$ 0.85, was extracted with CHCl$_3$, and the solvent was removed under reduced pressure to give methyl naphtho[2,3-b]thiophene-2-carboxylate (26.9 mg, 72%) as light yellow needles. This compound was amidinated in the usual fashion, with 10 equiv of Me$_3$Al/NH$_4$Cl and was purified by preparative tlc, eluting once with 20% MeOH/CHCl$_3$. The major band, R$_f$ 0.35 was extracted with MeOH/CHCl3, and the solvent removed rigorously under reduced pressure to give naphtho[2,3-b]thiophene-2-carboxamidine hydrochloride mono-MeOH (26.5 mg, 83%) as a bright yellow fluffy solid: $^1$H NMR (DMSO-d$_6$) δ 9.70, 9.43 (2H, 2H, 2 br s), 8.83 (1H,sl br s), 8.79 (1H,sl br s), 8.60 (1H,sl br s), 8.22 (1H, sl br d,J=8.1 Hz), 8.10 (1H, sl br d, J=8 Hz), 7.68, 7.64 (1H, 1H, ABq of dd, J$_{AB}$=6.9 Hz, J$_d$=8.0, 1.4 Hz).

Compound 314

Benzo[b]thiophene-5-carboxamidine hydrochloride

4-Fluorobenzonitrile was formylated with LDA and DMF in THF at −78° C. under the usual conditions to give 4-fluoro-3-formylbenzonitrile in 77% yield. This was annulated under the usual conditions with NaH and methyl thioglycollate to give methyl 5-cyanobenzo[b]thiophene-2-carboxylate in 64% yield. Saponification with NaOH in aqueous THF at 25° C. gave 5-cyanobenzo[b]thiophene-2-carboxylic acid in 92% yield, and this was decarboxylated by Cu powder in refluxing quinoline, and purified by preparative tlc, eluting with 15% EtOAc/hexanes, to give 5-cyanobenzo[b]thiophene in 49% yield. Amidination under the usual conditions gave benzo[b]thiophene-5-carboxamidine hydrochloride octahydrate (190 mg, 81%) as a light yellow waxy solid: $^1$H NMR (CD$_3$OD) δ 9.33 (1H,br s), 8.82 (1H,br s), 8.35 (1H,d,J=1.7 Hz), 8.17 (1H,d,J=8.6 Hz), 7.82 (1H,d,J=5.6 Hz), 7.72, (1H,dd,J=8.6, 1.7 Hz), 7.57 (1H,d,J=5.6 Hz), 4.91 (20H,br s).

Compound 315

Benzo[b]thiophene-6-carboxamidine hydrochloride

3-Fluorobenzonitrile was lithiated with LDA in THF at −78° C. in the usual manner and was reacted with chlorotrimethylsilane to give, after the usual workup and Kugelrohr distillation at 125° C./1 mm Hg, 3-fluoro-2-(trimethylsilyl)benzonitrile (93%) as a pale yellow oil which solidified on standing. This silane was formylated with LDA and DMF in THF at −78° C. in the usual manner to give 3-fluoro-4-formyl-2-(trimethylsilyl)benzonitrile in 81% yield. The aldehyde was annulated with NaH and methyl thioglycollate in DMSO, requiring heating to 80° C. for 5 min, and isolated in the usual manner to give methyl 6-cyano-7-(trimethylsilyl)benzo[b]thiophene-2-carboxylate in 31% yield. Treatment of this with 1.2 equiv of tetrabutylammonium fluoride hydrate in DMSO at 25° C. for 1 h effected complete desilylation to give methyl 6-cyanobenzo[b]thiophene-2-carboxylate in 83% yield. Saponification with NaOH in aqueous THF at 25° C. gave 6-cyanobenzo[b]thiophene-2-carboxylic acid in 83% yield, and this was decarboxylated with Cu powder in refluxing quinoline, and purified by preparative tlc, eluting with 15% EtOAc/hexanes, to give 6-cyanobenzo[b]thiophene in 49% yield. Amidination under the usual conditions gave benzo[b]thiophene-6-carboxamidine hydrochloride heptahydrate (221.1 mg, quantitative yield) as a light yellow waxy solid: $^1$H NMR (CD$_3$OD) δ 9.33 (2H,br s), 8.83 (2H,br s), 8.46 (1H,sl br s), 8.07 (1H,d,J=8.3 Hz), 7.93 (1H,d,J=5.4 Hz), 7.76, (1H,dd,J=8.3,1.7 Hz), 7.54 (1H,d,J=5.4 Hz), 4.93 (14H,br s).

Compound 316

Benzo[b]thiophene-3-carboxamidine hydrochloride

A solution of benzothiophene (271.1 mg, 2.0 mmol) and bromine (323 mg, 2.0 mmol) in CCl$_4$ (5 mL) was stirred under N$_2$ at 0° C. for 2 min, at 25° C. for 14 h, and then at 50° C. for 20 h, when all orange colouration had vanished. When the reaction cooled to 25° C., silica gel (5 g) was added, and the volatiles were removed under reduced pressure. The silica was extracted with ether, and the residue, after evaporation of the ether, was purified by preparative tlc, eluting with hexanes to give 3-bromobenzo[b]thiophene (331.2 mg, 78%) as a light yellow oil. n-Butyl lithium (2.5M in hexanes, 0.70 mL, 1.75 mmol) was added dropwise over 2 min to a solution of 3-bromobenzo[b]thiophene (329.5 mg, 1.55 mmol) in ether (5 mL) stirred under N$_2$ at −78° C. After 10 min the clear light yellow solution was blown rapidly through a catheter on to solid CO$_2$ in ether (50 mL). When the reaction mixture warmed up to 25° C., it was quenched with dilute HCl (1M, 10 mL), and the layers were separated. The organic phase was washed with water (10 mL), and extracted with dilute NaOH solution (0.2M, 2×10 mL). The combined basic extracts were washed with ether (10 mL), acidified with dilute HCl (1M, 10 mL), and were extracted with ether (3×10 mL). The combined extracts were washed with water (2×10 mL), saturated brine (10 mL), and dried (MgSO$_4$). The solvent was removed under reduced pressure and the residual solid was recrystallised from toluene to give benzo[b]thiophene-3-carboxylic acid (72.5 mg, 26%) as white needles mp 172.5°–174° C.

Benzo[b]thiophene-3-carboxylic acid (31.1 mg, 0.175 mmol) was dissolved in oxalyl chloride (0.5 mL) with gentle warming, and the mixture was stirred for a further 30 min at 25° C. The volatiles were removed under reduced pressure, and the residual light yellow oil was amidinated in the usual fashion with 6 equivalents of NH$_4$Cl/Me$_3$Al, to give benzo[b]thiophene-3-carboxamidine hydrochloride (15.6 mg, 42%) as a pale yellow glass. $^1$H NMR (CD$_3$OD) δ 8.46 (1H,s), 8.10 (1H,sl br d,J=7.6 Hz), 8.08 (1H,dd,J=7.6,1.2 Hz), 7.62 (1H,dt,J$_d$=1.2 Hz,J$_t$=7.4 Hz), 7.57 (1H,dt,J$_d$=1.3 Hz,J$_t$=8 Hz), 4.96 (4H,br s).

Compound 317

Benzo[b]thiophene-4-carboxamidine hydrochloride

Methyl 4-(1,3-dioxolan-2-yl)benzothiophene-2-carboxylate (253.2 mg, 0.96 mmol, Compound 22) was saponified with KOH (86.6 mg, 1.5 mmol) in MeOH (5 mL) at 80° C. for 3 h. The solvent was removed under reduced pressure, snd the residue was dissolved in water, rinsed with CHCl$_3$ and acidified to pH 1 with HCl (1M), then extracted twice with CHCl$_3$. The combined organic layers were dried (MgSO$_4$), filtered, and the solvent removed under reduced pressure to give 4-(1,3-dioxolan-2-yl)benzo[b]thiophene-2-carboxylic acid (198.2 mg, 83%) as a white solid. This acid (198.2 mg, 0.80 mmol) was decarboxylated with Cu powder (25.2 mg, 0.40 mmol) in quinoline (3 mL) at 220° C. for 30 min under N$_2$, then diluted with water and extracted with CHCl$_3$. The organic layer was washed with water, saturated brine, dried (MgSO$_4$), filtered, and concentrated to afford after chromatography (10% EtOAc/hexanes) 4-(1,3-dioxan-2-yl)benzo[b]thiophene (92.3 mg, 57%) as a light yellow syrup and benzothiophene-4-carboxaldehyde (36.4 mg, 28%) as a yellow-brown syrup. A mixture of ketal and aldehyde (114.3 mg, 0.58 mmol) was treated with TFA (20 μL) in 10% aqueous CH$_3$CN for 2.5 h. The mixture was poured onto saturated aqueous NaHCO$_3$ solution and the organic layer was washed with water, saturated brine, dried (MgSO$_4$), filtered, and evaporated to dryness to give benzo[b]thiophene-4-carboxaldehyde (92.3 mg, 98%) as a yellow-brown syrup.

A mixture of the aldehyde (92.3 mg, 0.57 mmol), hydroxylamine hydrochloride (47.4 mg, 0.68 mmol), and sodium acetate trihydrate (125.7 mg, 0.91 mmol) was heated in refluxing AcOH for 1.5 h. The mixture was cooled to 25° C. and the AcOH was removed under reduced pressure. The crude product was dissolved in EtOAc and washed twice with water, saturated brine, dried (MgSO$_4$), filtered, and evaporated to dryness. The material obtained was shown by $^1$H NMR (CDCl$_3$) to be the oxime. The oxime was dissolved in CH$_2$Cl$_2$ (5 mL) to which mesyl chloride (78.2 mg, 0.68 mmol), and DBU (215.0 mg, 1.4 mmol) were added. After 16 h the mixture was diluted with CHCl$_3$ and washed with H$_2$O. The organic layer was dried (MgSO$_4$), filtered, and evaporated to dryness to afford after preparative tlc (15% EtOAc/hexanes) 4-cyanobenzo[b]thiophene (72.3 mg, 80%) as a light yellow syrup. This nitrile was amidinated with 5 equiv. NH$_4$Cl/Me$_3$Al in xylenes (7 mL) at 145° C. for 1 h under N$_2$ to afford after workup and chromatography (20% MeOH/CHCl$_3$) benzo[b]thiophene-4-carboxamidine hydrochloride (72.1 mg, 75%) as an off-white solid: $^1$H NMR (DMSO-d$_6$) δ 9.56 (4H, br s), 8.37 (1H,d,J=8.3 Hz), 8.06 (1H,d,J=5.6 Hz), 7.69 (1H,d,J=7.2 Hz), 7.57–7.60 (2H,m).

Compound 318

Pyrido[2,3-b]thiophene-2-carboxamidine hydrochloride.

2Fluoropyridine was formylated with LDA and DMF in THF at −78° C. under the usual conditions to give 2-fluoropyridine-3-carboxaldehyde in 83% crude yield. The aldehyde was annulated with NaH and methyl thioglycollate in DMSO, requiring heating to 80° C. for 5 min, and isolated in the usual manner to give methyl pyrido[2,3-b]thiophene-2-carboxylate in 29% yield. Amidination under the usual conditions gave pyridol[2,3-b]thiophene-2-carboxamidine hydrochloride hexahydrate (164.4 mg, 98%) as a light yellow solid: $^1$H NMR (CD$_3$OD) δ 8.77 (1H,sl br d,J=4.6 Hz), 8.51 (1H,d,J=8.3 Hz), 8.27 (1H,sl br s), 7.63, (1H,ddd,J=8.3, 4.6, 1.0 Hz), 4.92 (16H, br s).

Compound 319

2-Guanidinobenzo[b]thiophene hydrochloride

To a 0° C. solution of benzo[b]thiophene-2-carboxylic acid (387.1 mg, 2.17 mmol), in THF (8 mL) under N₂, was added Et₃N (360 μL, 2.58 mol) followed by isobutylchloroformate (300 μL, 2.35 mmol), and the mixture (containing a thick, white precipitate) was stirred for 30 min. The ice-bath was removed and the reaction was stirred for 10 min, re-cooled to 0° C., and a solution of sodium azide (287.8 mg, 4.43 mmol) in water (1 mL) was added dropwise. The nearly homogeneous mixture was stirred for 30 min, and the cold-bath was removed. After 10 min, the reaction mixture was diluted with Et₂O, washed with water (3×), saturated brine, and dried (MgSO₄). After filtration and solvent evaporation, the residue was dissolved in toluene (10 mL) and placed, under N₂, in a pre-heated, 110° C. oil-bath. After 1 h the reaction was cooled to 25° C., and ammonia was bubbled into the reaction mixture which was vigorously stirred. A white precipitate formed after ca. 15 sec. The ammonia bubbling was continued for ca. 10 min, and the thick mixture was stirred for an additional 20 min. The solids were removed by filtration and washed with cold hexane to afford N-(benzo[b]thien-2-yl)urea (379.5 mg, 91%) as a light yellow, pearly solid.

This urea (25.4 mg, 0.13 mmol) was treated with 6.0 equiv of Me₃Al/NH₄Cl (xylene, 130° C., 27 h) to give, after workup and purification by flash chromatography (20% MeOH/CHCl₃), a mixture of the desired guanidine and an unidentified product (12.6 mg, ca. 4:1). Water (ca. 2 mL) and 10% aqueous HCl (ca 2 mL) was added to the mixture, which was filtered through a 0.25 micron filter. Removal of the water under reduced pressure afforded 2-guanidinobenzo[b]thiophene hydrochloride dihydrate (11.2 mg, 37%) as an off-white film: ¹H NMR (CD₃OD) δ 8.72 (1H,s), 8.16 (1H,d,J=8.3 Hz), 8.07 (1H,d,J=8.2 Hz), 7.92 (1H,t,J=7.7 Hz), 7.80 (1H,t,J=7.5 Hz), 4.97 (9H,v br s).

Compound 320

N-Amidino benzo[b]thiophene-2-carboxamide hydrochloride

A solution of guanidine (59 mg, 1 mmol) and 2-benzothienoyl chloride (88.6 mg, 0.5 mmol) in DMSO (1.8 mL) was stirred under N₂ at 25° C. for 14 h. The volatiles were removed by Kugelrohr distillation at 25° C., and the residual yellow oil was purified by preparative tlc, eluting with 20% MeOH in CHCl₃. The minor band R/0.67 was extracted with CHCl₃/MeOH, and the residue after solvent removal was recrystalised from dilute HCl (0.03M, 4 mL) to give N-amidino benzo[b]thiophene-2-carboxamide hydrochloride (14.7 mg, 11.5%) as white needles. ¹H NMR (DMSO) δ 12.52 (1H,br s), 8.83 (1H,sl br s) 8.75–8.50 (4H,br s), 8.17 (1H,d,J=8.1 Hz), 8.09 (1H,d,J=7.9 Hz), 7.64 (1H,t,J=7.4 Hz), 7.57 (1H,t,J=7.5 Hz).

Compound 321

Thieno[2,3-b]thiophene-2-carboxamidine hydrochloride n-Butyl lithium (2.13M in hexanes, 2.4 mL, 5.1 mmol) was added dropwise to a solution of diisopropylamine (554.4 mg, 5.5 mmol) in THF (5 mL), stirred under N₂ at 25° C. After 10 min the solution was added dropwise over 10 min via catheter to a solution of 3-bromothiophene (816.6 mg, 5.0 mmol) in THF (10 mL), stirred under N₂ at −78° C. After a further 30 min S-(4-methoxybenzyl)thiotosylate (1.531 g, 5.0 mmol) in THF (5 mL) was added dropwise to the cold solution, and after a further 1 h, at −78° C., the reaction mixture was stirred at 25° C. for 1 h. The slurry was poured onto water (50 mL), and was extracted with ether (3×20 mL). The combined extracts were washed with dilute HCl (0.4 M, 20 mL), water (20 mL), dilute Na₂CO₃ solution (20 mL), saturated brine (20 mL), and dried (MgSO₄). The solvent was removed under reduced pressure, and the residue was Kugelrohr distilled at 225° C./0.13 mmHg to give 3-bromo-2-(4-methoxybenzylthio)thiophene (959 mg, 61%) as an orange oil.

This bromide (939 mg, 2.98 mmol) was stirred in ether (10 mL) at −78° C. under N₂, and n-butyl lithium (2.13M in hexanes, 1.53 mL, 3.3 mmol) was added dropwise over 5 min. After a further 5 min DMF (0.30 mL, 3.9 mmol) was added dropwise. After another 10 min, the reaction mixture was quenched at −78° C. by the rapid addition of acetic acid (0.5 mL), followed by water (10 mL) and hexanes (10 mL). The precipitate was collected by Buchner filtration, rinsed with water (2×10 mL) and hexanes (10 mL), and was dried in a vacuum drying oven at 40° C. to give 2-(4-methoxybenzylthio)thiophene-3-carbaldehyde (639.1 mg, 81%) as a light yellow solid.

Silver acetate (88.9 mg, 0.53 mmol) was added to a dark solution of 2-(4-methoxybenzylthio)thiophene-3-carbaldehyde (132.2 mg, 0.5 mmol) and anisole (150 μL) in TFA (1 mL), stirred under N₂ at 0° C. After 2.5 h at 0° C., the volatiles were removed rigourously under reduced pressure, and the green residue was dispersed in DMF (2 mL) with sonication. The slurry was stirred under N₂ at 25° C., and methyl bromoacetate (95 μL) and Hunig's base (0.35 mL) were added. After 20 h, the reaction mixture was diluted with ether (30 mL), filtered, and washed with water (3×10 mL), saturated brine (10 mL), and dried (MgSO₄). The solvent was removed under reduced pressure, and the residue was purified by preparative tlc on silica (15% EtOAc in hexanes) to give methyl 2-(3-formylthien-2-ylthio)ethanoate (57.7 mg, 64% yield based on recovered SM) as a yellow crystalline solid.

Methyl 2-(3-formylthien-2-ylthio)ethanoate (57.7 mg, 0.265 mmol) and triethylamine (0.20 g, 2 mmol) were heated in DMSO (2 mL) under N₂ with stirring for 2 h. The reaction mixture was diluted with ether (30 mL), and was washed with dilute HCl (1M, 10 mL), water (2×10 mL), and saturated brine (10 mL), and dried (MgSO₄). The solvent was removed under reduced pressure, and the residue was purified by preparative tlc on silica (10% EtOAc in hexanes) to give methyl thieno[2,3-b]thiophene-2-carboxylate (43.3 mg, 82%) as a crystalline solid mp 105°–6° C.

The ester (13.5 mg, 0.067 mmol) was amidinated in the usual fashion with 15 equivalents of Me₃Al/NH₄Cl to give after preparative tlc on silica (15% CH₃OH in CHCl₃) thieno[2,3-b]thiophene-2-carboxamidine hydrochloride (11.6 mg, 78%) as a light yellow solid. ¹HNMR (DMSO) δ 9.48, 9.25 (2H,2H,2br s), 8.35 (1H,s), 7.84 (1H,d,J=5.3 Hz), 7.53 (1H,d,J=5.3 Hz).

Compound 322

Thieno[3,2-b]thiophene-2-carboxamidine hydrochloride n-Butyl lithium (2.5M in hexanes, 4.2 mL, 10.5 mmol) was added dropwise to a solution of diisopropylamine (1.112 g, 11 mmol) in THF (10 mL), stirred under $N_2$ at 25° C. After 10 min the solution was added dropwise over 10 min via catheter to a solution of 3-bromothiophene (1.6302 g, 10 mmol) in (THF 10 mL), stirred under $N_2$ at −78° C. After a further 1 h, DMF (1.0 mL, 12.5 mmol) was added dropwise, followed after 10 min by a rapid addition of acetic acid (2.0 mL). The resultant gel was quickly decomposed with water (50 mL), and the mixture was extracted with ether (3×20 mL). The combined extracts were washed with dilute HCl (1 m, 20 mL), water (2×20 mL), saturated $Na_2CO_3$ solution (20 mL) and dried ($MgSO_4$). The solvent was removed under reduced pressure, and the residue was Kugelrohr distilled at 100° C./0.2 mmHg to give 3-bromothiophene-2-carbaldehyde (1.4276 g, 75%) as a light yellow oil.

n-Butyl lithium (2.13M in hexanes, 0.52 mL, 1.1 mmol) was added dropwise to a solution of N,N,N'-trimethylethylene diamine (113.2 mg, 1.1 mmol) in ether (5 mL), stirred under $N_2$ at 0° C. After 15 min the reaction was cooled to −78° C., and 3-bromothiophene-2-carbaldehyde (191.7 mg, 1.0 mmol) was added dropwise over 2 min. After another 15 min n-butyl lithium (0.52 mL, 1.1 mmol) was added dropwise over 2 min, followed 5 min later by a solution of S-(4-methoxybenzyl)-thiotosylate (370.2 mg, 1.2 mmol) in ether (3 mL), over 5 min. After a further 2 h at −78° C., the reaction mixture was quenched by the rapid addition of acetic acid (0.5 mL), and was poured onto water (10 mL), and extracted with ether (3×10 mL). The combined extracts were washed with dilute HCl (0.2M, 10 mL), water (10 mL), dilute NaOH solution (0.2M, 10 mL), water (10 mL), saturated brine (10 mL), and dried ($MgSO_4$). The solvent was removed under reduced pressure, and the residue was purified by preparative tlc on silica (15% EtOAc in hexanes) to give 3-(4-methoxybenzylthio)thiophene-2-carbaldehyde (185.8 mg, 57% correcting for 20 mol % sulfenylating agent) as a bright orange oil.

Silver acetate (105.6 mg, 0.63 mmol) was added to a dark solution of 3-(4-methoxybenzylthio)thiophene-2-carbaldehyde (170.6 mg, 80% by weight, 0.5 mmol) and anisole (150 μL) in TFA (1 mL), stirred under $N_2$ at 0° C. After 2.5 h at 0° C., the volatiles were removed rigourously under reduced pressure, and the orange-brown residue was dispersed in DMF (2 mL) with sonication. The slurry was stirred under $N_2$ at 25° C., and methyl bromoacetate (95 μL) and Hunig's base (0.35 mL) were added. The reaction mixture gelled within 10 min, and was reliquified by sonication. After 20 h, the reaction mixture was diluted with ether (30 mL), filtered, and washed with water (3×10 mL), saturated brine (10 mL), and dried ($MgSO_4$). The solvent was removed under reduced pressure, and the residue was purified by preparative tlc on silica (15% EtOAc in hexanes) to give methyl 2-(2-formylthien-3-ylthio)ethanoate (47.8 mg, 59% yield based on recovered SM) as a pale yellow gum.

Methyl 2-(2-formylthien-3-ylthio)ethanoate (47.8 mg, 0.22 mmol) and triethylamine (0.20 g, 2 mmol) were heated in DMSO (2 mL) under $N_2$ with stirring for 2 h. The reaction mixture was diluted with ether (30 mL), and was washed with dilute HCl (1M, 10 mL), water (2×10 mL), and saturated brine (10 mL), and dried ($MgSO_4$). The solvent was removed under reduced pressure, and the residue was purified by preparative tlc on silica (10% EtOAc in hexanes) to give methyl thieno[3,2-b]thiophene-2-carboxylate (36.2 mg, 83%) as a crystalline solid mp 96°–7° C.

The ester (11.4 mg, 0.058 mmol) was amidinated in the usual fashion with 17 equivalents of $Me_3Al/NH_4Cl$ to give after preparative tlc on silica (15% $CH_3OH$ in $CHCl_3$) thieno[3,2-b]thiophene-2-carboxamidine hydrochloride hemi methanolate (12.1 mg, 90%) as a light yellow-brown glass. $^1HNMR$ (DMSO) d 9.6–9.25 (4H,br s), 8.50 (1H,s), 8.10 (1H,d,J=5.2 Hz), 7.69 (1H,d,J=5.2 Hz).

Compound 323

Thieno[3,4-b]thiophene-2-carboxamidine hydrochloride n-Butyl lithium (1.97M in hexanes, 1.02 mL, 2.0 mmol) was added dropwise over 5 min to a solution of 3,4-dibromobenzothiophene (483.6 mg, 2.0 mmol) in ether (5 mL) stirred under $N_2$ at −78° C. After a further 5 min S-(4-methoxybenzyl)thiotosylate (616.0 mg, 2.0 mmol) in ether (7 mL) was added dropwise over 10 min. After a further 15 min at −78° C., the reaction mixture was stirred at 25° C. for 30 min, and was then recooled to −78° C. Further n-butyl lithium (1.97M in hexanes, 1.05 mL, 2.05 mmol) was added dropwise over 2 min. After a further 5 min, DMF (0.20 mL, 2.5 mmol) was added dropwise, and after a further 10 min the −78° C. mixture was quenched by the rapid addition of acetic acid (1.0 mL), and pouring onto water (10 mL). The mixture was extracted with $CHCl_3$ (2×20 mL), and the combined organic phases were washed with water (10 mL), saturated $NaHCO_3$ solution (10 mL) and saturated brine (10 mL) and dried (MgSO4). The solvent was removed under reduced pressure, and the residue was purified by preparative tlc (1% MeOH in $CHCl_3$) to give 4-(4-methoxybenzylthio)thiophene-3-carbaldehyde (440.9 mg, 83%) as a yellow-brown solid.

Silver acetate (68 mg, 0.41 mmol) was added to a dark solution of 4-(4-methoxybenzylthio)thiophene-3-carbaldehyde (0.13 g, 0.4 mmol) and anisole (150 μL) in TFA (1 mL), stirred under $N_2$ at 25° C. After 3 h, the volatiles were removed rigorously under reduced pressure, and the yellow-brown residue was dispersed in DMF (2 mL) with sonication. The slurry was stirred under $N_2$ at 25° C., and methyl bromoacetate (95 μL) and Hunig's base (0.35 mL) were added. After 4 h, the reaction mixture was diluted with ether (30 mL), filtered, and washed with dilute HCl (1M, 10 mL), water (2×10 mL), saturated brine (10 mL), and dried (MgSO4). The solvent was removed under reduced pressure, and the residue was purified by preparative tlc on silica (1% MeOH in $CHCl_3$) to give methyl 2-(4-formylthien-3-ylthio)ethanoate (22.6 mg, 23% uncorrected yield) as a yellow-brown gum.

Methyl 2-(4-formylthien-3-ylthio)ethanoate (22.6 mg, 0.10 mmol) and triethylamine (0.1 g, 1 mmol) were heated in DMSO (1 mL) under $N_2$ with stirring for 6 h. The reaction mixture was diluted with ether (30 mL), and was washed with dilute HCl (1M, 10 mL), water (2×10 mL), and saturated brine (10 mL), and dried (MgSO4). The solvent was removed under reduced pressure, and the residue was purified by preparative tlc on silica ($CHCl_3$) to give methyl thieno[3,4-b]thiophene-2-carboxylate (7.2 mg, 35%) as a pale yellow, waxy, solid, which darkened on standing.

The ester (7.2 mg, 0.036 mmol) was amidinated in the usual fashion with 27 equivalents of $Me_3Al/NH_4Cl$ to give after preparative tlc on silica (15% $CH_3OH$ in CHCl$_3$) thieno[3,4-b]thiophene-2-carboxamidine hydrochloride dihydrate (8.9 mg, quant) as a light brown glass. $^1$HNMR (CD$_3$OD) δ 7.99 (1H,d,J=2.7 Hz), 7.90 (1H,s), 7.69 (1H,dd,J=0.7,2.7 Hz).

EXAMPLE 2

ANALYSIS OF CANDIDATE UROKINASE INHIBITORS

Urokinase inhibitors may be tested for efficacy in a number of in vitro and in vivo assays. Examples of such assays are provided below. These assays (which were used to test the compounds described herein) together provide an accurate assessment of a particular compound's ability to specifically inhibit a broad range of urokinase functions.

Briefly, the inhibitory potency of a compound of the invention as well as the specificity of this inhibition (e.g., relative to certain other proteases) have been demonstrated through the use of the following assays:

(i) A direct chromogenic assay in which urokinase cleaves a synthetic tripeptide p-nitroanilide (pNA) urokinase substrate.

(ii) An indirect plasminogen-linked assay in which urokinase proteolytically activates plasminogen, forming plasmin which then cleaves a synthetic tripeptide pNA plasmin substrate. Since this assay is based on urokinase cleavage of its sole natural substrate plasminogen (as opposed to a low molecular weight synthetic tripeptide), it is the most valid indicator of physiologically-relevant urokinase inhibitory potency.

(iii) A cell-based plasminogen-linked urokinase assay employing whole living HT-1080 human fibrosarcoma or mouse Lewis lung carcinoma cells together with plasminogen and synthetic tripeptide pNA plasmin substrate, permitting demonstration of inhibitory activity of the compounds against cell-surface receptor-bound urokinase.

(iv) Both direct and plasminogen-linked pNA assays for tPA, the other mammalian plasminogen activator and the key initiator of blood clot dissolution or fibrinolysis. Since urokinase and tPA share an absolute specificity for the same peptide bond in plasminogen, urokinase inhibitors designed to block cellular invasiveness must be highly specific for urokinase over tPA in order to avoid serious thrombotic side effects secondary to undesired blockage of normal fibrinolysis.

(v) A chromogenic pNA assay for plasmin, the potent general protease produced by cleavage of plasminogen by either urokinase or tPA. Although urokinase initiates cellular invasiveness by generating plasmin, the additional importance of plasmin in tPA-mediated fibrinolysis dictates that plasmin itself should be free from inhibition by urokinase inhibitors designed as anti-invasiveness agents.

(vi) Chromogenic pNA assays for certain other serine proteases outside of the plasminogen activating or fibrinolytic pathways, including trypsin, chymotrypsin, thrombin, and kallikrein. These assays are used to assess inhibitory activities of compounds against these additional proteases.

(vii) A cell-based [$^3$H]fibronectin degradation assay used to demonstrate the ability of our compounds to inhibit urokinase-mediated proteolysis of a major ECM component, fibronectin, by whole living HT-1080 human fibrosarcoma cells. This assay therefore demonstrates functional significance of our inhibitors in an invasive tumor cell system.

ENZYME ASSAYS

All enzyme assays were performed in 96-well microtiter plates. Formats of all enzyme assays were based on chromogenic microtiter plate assays previously developed for plasminogen activators and described in: Karlan, B. Y., Clark, A. S., and Littlefield, B. A. (*Biochem, Biophys. Res. Commun.* 142:147–54, 1987).

Urokinase Direct Assay

Compounds to be tested were incubated at desired concentrations (typically between 1 nM and 1 mM) with 25 International Units (IU)/ml human high molecular weight urokinase (American Diagnostica, Greenwich, Conn.) and 1 mM urokinase substrate (benzoyl-β-alanyl-glycyl-arginine-4-nitroanilide; Pefachrome UK ®, Pentapharm, Ltd., Basel, Switzerland; USA distributors, Centerchem, Inc., Stamford, Conn.) in a 100 μl final volume of 50 mM Tris, 100 mM NaCl, 1 mM Na$_2$EDTA, 0.01% (v/v) polyoxyethylenesorbitan monooleate (Tween 80), pH 7.5 (Buffer Z). Incubations were carried out at 37° C. for approximately 2 hours or until adequate yellow color developed. Color was quantitated by measuring absorbance at 405 nm (A$_{405}$) using a Titertek Multiskan MCC/340 MK II microtiter plate spectrophotometer.

Urokinase Indirect (Plasminogen-Linked) Assay

Compounds to be tested were incubated at desired concentrations (typically between 1 nM and 1 mM) with 25 IU/ml urokinase together with 25 μg/ml human Glu-plasminogen (American Diagnostica), 25 μg/ml soluble des-AA-fibrinogen (Desafib ®, American Diagnostica), and 1 mM plasmin substrate (H-D-norleucylhexahydrotyrosyl-lysine-4-nitroanilide; Spectrozyme PL ®, American Diagnostica) in a 100 μl final volume of Buffer Z (see urokinase direct assay above). Incubations were carried out at 22° C. for 45–60 minutes or until adequate color developed. Color qas quantitated as in the urokinase direct assay above. Parallel incubations were performed with and without plasminogen, and corrected absorbance values were obtained by subtracting values obtained without plasminogen from those obtained with plasminogen, eliminating any contribution of direct cleavage, if any, of plasmin substrate by urokinase.

tPA Direct Assay

This assay was carried out as described above for the urokinase direct assay, except: (i) 0.5 μg/ml human two-chain tPA (American Diagnostica) was substituted for urokinase, and (ii) 1 mM tPA substrate (methylsulfonyl-D-cyclohexyltyrosylglycyl-arginine-4-nitroaniline acetate; Spectrozyme tPA ®, American Diagnostica) was substituted for urokinase substrate.

tPA Indirect (Plasminogen-Linked) Assay

This assay was carried out as described above for the urokinase indirect assay, except that 0.5 μg/ml human two-chain tPA was substituted for urokinase. As described above for the urokinase indirect assay, parallel incubations were performed with and without plasminogen to allow correction for direct cleavage, if any, of plasmin substrate by tPA.

Plasmin Assay

Compounds to be tested were incubated at desired concentrations (typically between 1 nM and 1 mM)

with 125 ng/ml human plasmin (American Diagnostica) together with 1 mM plasmin substrate (see urokinase indirect assay above) in a 100 μl final volume of Buffer Z (see urokinase direct assay above). All other assay conditions, as well as methods of color quantitation, were carried out as described above for the urokinase direct assay.

Chymotrypsin Assay

Compounds to be tested were incubated at desired concentrations (typically between 1 nM and 1 mM) with 1 mg/ml bovine pancreas chymotrypsin (Boehringer Mannheim, Indianapolis, Ind.) together with 1 mM chymotrypsin substrate (succinyl-L-phenylalanine-4-nitroanilide; Boehringer Mannheim) in a 100 μl final volume of Buffer Z (see urokinase direct assay above). All other assay conditions, as well as methods of color quantitation, were carried out as described for the urokinase direct assay above.

Elastase Assay

Compounds to be tested were incubated at desired concentrations (typically between 1 nM and 1 mM) with 25 μg/ml human neutrophil elastase (Calbiochem, La Jolla, Calif.) together with 1 mM elastase substrate (N-succinyl-alanyl-alanyl-alanine-4-nitroanilide; Sigma Chemical Co., St. Louis, Mo.) in a 100 μl final volume of Buffer Z (see urokinase direct assay above). All other assay conditions, as well as methods of color quantitation, were carried out as described for the urokinase direct assay above.

Kallikrein Assay

Compounds to be tested were incubated at desired concentrations (typically between 1 nM and 1 mM) with 100 mIU/ml human plasma kallikrein (Calbiochem) together with 1 mM kallikrein substrate (benzoyl-prolyl-phenylalanyl-arginine-4-nitroanilide; Chromozym PK ®, Boehringer Mannheim) in a 100 μl final volume of Buffer Z (see urokinase direct assay above). All other assay conditions, as well as methods of color quantitation, were carried out as described for the urokinase direct assay above.

Thrombin Assay

Compounds to be tested were incubated at desired concentrations (typically between 1 nM and 1 mM) with 10 mIU/ml human plasma thrombin (Boehringer Mannheim) together with 1 mM thrombin substrate (tosyl-glycyl-prolyl-arginine-4-nitroanilide; Chromozym TH ®, Boehringer Mannheim) in a 100 μl final volume of Buffer Z (see urodinase direct assay above). All other assay conditions, as well as methods of color quantitation, were carried out as described for the urokinase direct assay above.

Trypsin Assay

Compounds to be tested were incubated at desired concentrations (typically between 1 nM and 1 mM) with 0.3 μg/ml bovine pancreas trypsin (Boehringer Mannheim) together with 1 mM trypsin substrate (benzoyl-valyl-glycyl-arginine-4-nitroanilide; Pefachrome TRY ®, Pentapharm) in a 100 μl final volume of Buffer Z (see urokinase direct assay above). All other assay conditions, as well as methods of color quantitation, were carried out as described for the urokinase direct assay above.

CELL-BASED ASSAYS

Cell Surface Urokinase Inhibition Assay

This assay is similar to the urokinase indirect assay described above, except that HT1080 human fibrosarcoma cells (ATCC CCL121, American Type Culture Collection, Rockville, Md.) or mouse Lewis lung carcinoma cells (ATCC CRL1642) are used as the source of cell surface urokinase.

Compounds to be tested were incubated at desired concentrations (typically between 1 nM and 1 nM) with $5 \times 10^4$ HT1080 cells or mouse Lewis lung carcinoma cells (grown under standard tissue culture conditions; harvested without trypsinization) together with 25 μg/ml plasminogen and 1 mM plasmin substrate (see urokinase indirect assay above) in a 100 μl final volume of Buffer Z (see urokinase direct assay above). Incubations were performed in a humidified atmosphere containing 5% $CO_2$ at 37° C. for 2 hours or until adequate color developed. Color was quantitated as in the urokinase direct assay above. Parallel incubations were performed with and without plasminogen to allow correction for direct cleavage, if any, of plasmin substrate by urokinase. Control experiments using anti-urokinase monoclonal antibodies demonstrated that all cell-associated plasminogen activator activity measurable in this assay was urokinase-derived, eliminating any concerns that cell-associated tPA might interfere with assay results.

Cell-based [$^3$H]Fibronectin Degradation Assay

Wells of 96-well plastic tissue culture plates were pre-coated with 1 μg [$^3$H]fibronectin (specific activity, $3 \times 10^4$ dpm/μg; prepared as described by McAbee, D. D. and Grinell, F., *J. Cell Biol.* 97:1515–1523, 1983) in a 50 μl volume of unsupplemented Eagle's Minimum Essential Medium (EMEM) for 18 hours at 37° C. in a humidified atmosphere containing 5% $CO_2$. After 5 washes with 200 μl phosphate-buffered saline (PBS) to remove unbound radioactivity, compounds to be tested were placed in the wells at appropriate concentrations (typically between 1 nM and 1 mM) in a 50 μl volume of serum-free EMEM containing 10 mg/ml bovine serum albumin (BSA) and either 400 μg/ml plasminogen or 400 μg/ml additional BSA. Fifty microliter volumes of HT1080 cell suspensions (harvested without trypsinization) containing $1 \times 10^6$ cells/ml were then added, and the incubations continued for 18 hours at 37° C. in a humidified atmosphere containing 5% $CO_2$. Radioactivity levels in 50 μl aliquots of the supernatants was then determined by liquid scintillation counting. Differences in radioactivity levels between samples containing and not containing plasminogen represented urokinase-dependent degradation of [$^3$H]fibronectin since, in control experiments, anti-urokinase monoclonal antibodies effectively eliminated all plasminogen-dependent degradation of [$^3$H]fibronectin.

EXAMPLE 3

ACTIVITY OF THE UROKINASE INHIBITORS

Figure 1A:
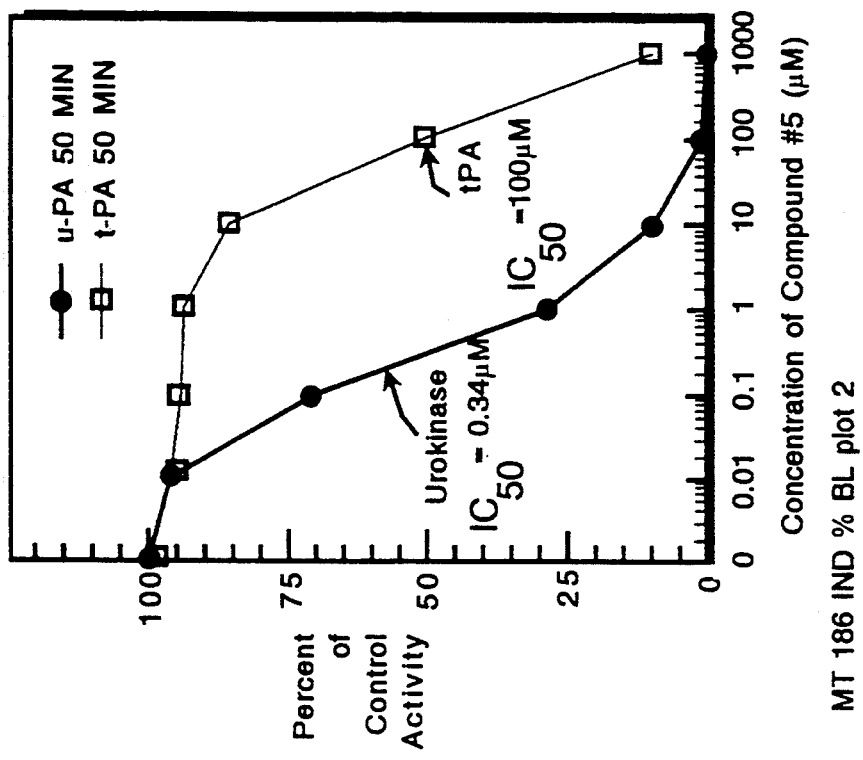
Figure 1C:
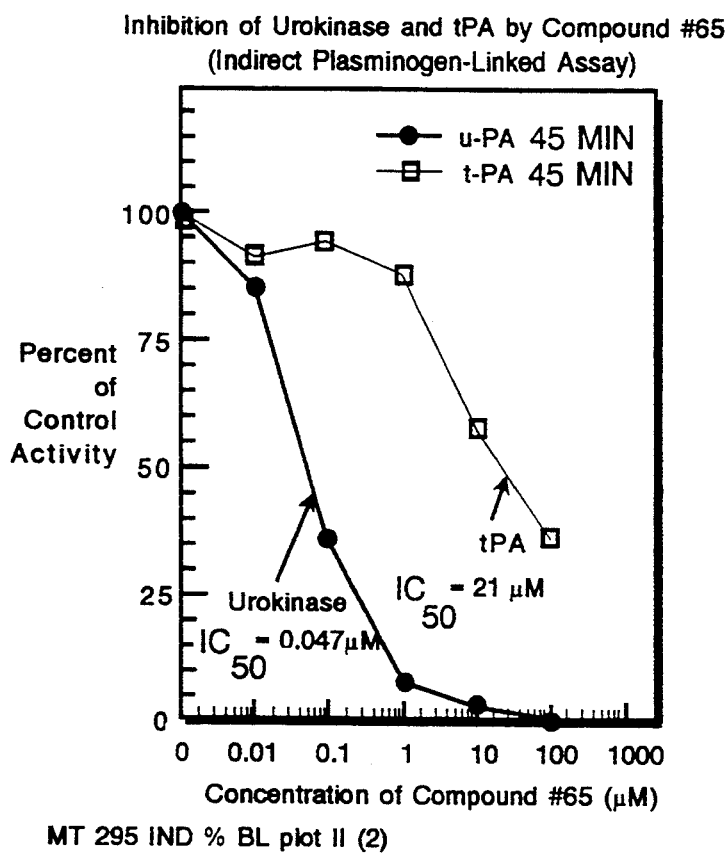

Using the assays described above, inhibitory activities of sample compounds according to the invention were determined; these results are presented in Table 3 and FIG. 1. In Table 3, the $IC_{50}$ value for a given compound, as assayed in the Urokinase Indirect Plasminogen-Linked Assay (supra), is shown in column 4 and expressed as a simple number. Column 3 shows the results from the Urokinase Direct Assay (supra); these results represent the percentage of residual urokinase activity at an inhibitor concentration of 1 mM (relative to inhibitor-free controls). Percentages followed by an asterisk indicate that the 1 mM reading was not useful, either because it was a value of zero or less or because it was artificially high due to compound absorbance at the assay wavelength. For these compounds, activity was estimated by dividing the 100 μM reading by 5, a modification which likely underestimates potency slightly.

TABLE 3

ACTIVITY OF THE 4- AND 5-SUBSTITUTED BENZOTHIOPHENE AND THIENOTHIOPHENE UROKINASE INHIBITORS

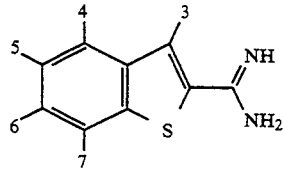

| Compound # | 4-SUBSTITUTED | uPA Direct | uPA Indirect (plasminogen-linked) |
|---|---|---|---|
| 1 | H | 25 (3.5%) | 4.9 |
| 2 | F | 7.2% | |
| 3 | Cl | 3.0% | |
| 4 | Br | 0.8% | |
| 5 | I | 3.3 | 0.33 |
| 6 | $CH_3$ | 13 | 0.59 |
| 7 | $C_2H_5$ | 10.0 | 0.7 |
| 8 | $i-C_3H_7$ | 0.9% | |
| 9 | $n-C_3H_7$ | 5.8 | 0.66 |
| 10 | $n-C_4H_9$ | 3.3 | 0.42 |
| 11 | $CH_2CH(CH_3)C_2H_5$ | 2.3% | |
| 12 | $CH_2CH_2CH(CH_3)_2$ | 3.2 | 0.34 |
| 13 | $n-C_6H_{13}$ | 4.4 | 0.42 |
| 14 | $CH_2CH_2-c-C_3H_7$ | 0.54% | |
| 15 | $CH_2CH_2C_6H_5$ | 0.35% | |
| 16 | $CH_2(CH_3)C_6H_5$ | 1.4% | |
| 17 | $CH=CH_2$ | 6.9 | 1.4 |
| 18 | $C(CH_3)=CH_2$ | 1.3% | |
| 19 | $CH_2CH=CH_2$ | 4.9 | 0.45 |
| 20 | $CH=CHC_2H_5$ | 0.8% | |
| 21 | $CH=C(CH_3)C_2H_5$ | 1.1% | |
| 22 | $CH=CHCH(CH_3)_2$ | 1.4 | 0.11 |
| 23 | $\underline{E}-CH=CHCH(CH_3)_2$ | 1.4 | 0.13 |
| 24 | $CH_2CH=C(CH_3)_2$ | 0.3%* | |
| 25 | $\underline{E}CH=CHC_3H_7$ | 1.7 | 0.14 |
| 26 | $\underline{E}-CH=CH\ CH_2CH(CH_3)_2$ | 0.46%* | |
| 27 | $\underline{E}-CH=CHCH(CH_3)C_2H_5$ | 0.26%* | |
| 28 | $\underline{E}-CH=CHCH(C_2H_5)_2$ | 0.46% | |
| 29 | $CH=CHC_4H_9$ | 4.2 | 0.34 |
| 30 | $\underline{E}-CH=CHC_6H_{13}$ | 0.88%* | |
| 31 | $\underline{E}-CH=CHC_8H_{17}$ | 5.2% | |
| 32 | $CH=CH(CH_2)_3OH$ | 0.67% | |
| 33 | $CH=CH(CH_2)_5C(NH)NH_2$ | 1.3% | |
| 34 | $CH=CH-c-C_3H_5$ | 0.46% | |
| 35 | $\underline{E}-CH=CH-c-C_6H_{11}$ | 0.22%* | |
| 36 | $CH_2CH=CHC_6H_5$ | 0.92%* | |
| 37 | $CH=CH(CH_2)_3C_6H_5$ | 0.84%* | |
| 38 | $CH=CBr_2$ | 4.8% | |
| 39 | $C\equiv CH$ | 7.3 | 0.66 |
| 40 | $C\equiv CCH(CH_3)_2$ | 0.48%* | |
| 41 | $C\equiv CC(CH_3)_3$ | 0.56%* | |
| 42 | $C\equiv CC(CH_3)_2OH$ | 0.6% | |
| 43 | $C\equiv C-c-C_6H_{11}$ | 0.44%* | |
| 44 | $C_6H_5$ | 13.4 | 1.1 |
| 45 | $p-OCH_3-C_6H_4$ | 6% | |
| 46 | $p-NO_2-C_6H_4$ | 1% | |
| 47 | $p-amidino-C_6H_4$ | 7.6% | |
| 48 | 3-PYRIDYL | 7.7 | 0.56 |
| 49 | 2-FURYL | 3.0 | 0.36 |
| 50 | 2-THIENYL | 5.2 | 0.50 |
| 51 | 2-BENZOFURANYL | 5.8 | 0.56 |
| 52 | 4-BENZOTHIEN-2-$C(NH)NH_2$ | 2.7% | |
| 53 | 5-[{4-C[NH]$NH_2$}Ph]FUR-2-YL | 0.22%* | 0.092 |
| 54 | $CF_3$ | 2.4% | |
| 55 | CHO | 4.8% | |
| 56 | $CH_2OH$ | 15 | 0.88 |
| 57 | $OCH_3$ | 12% | |
| 58 | $SCH_3$ | 6.9 | 0.56 |
| 59 | $SCH_2CH=CH_2$ | 1.1% | |

TABLE 3-continued

ACTIVITY OF THE 4- AND 5-SUBSTITUTED BENZOTHIOPHENE
AND THIENOTHIOPHENE UROKINASE INHIBITORS

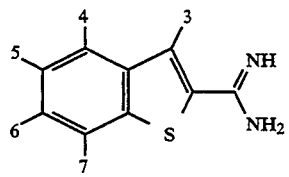

| | | | |
|---|---|---|---|
| 60 | SCH$_2$Ph | 1.3% | |
| 61 | 2-TETRAHYDROFURANYL | 0.6% | |
| 62 | 1-MORPHOLINO | 3.6% | |
| 63 | CH=CHC$_6$H$_5$ | 1.8 | 0.14 |
| 64 | CH=CH—C$_6$H$_3$-3,4-di-OCH$_3$ | 0.6%* | |
| 65 | CH=CH—C$_6$H$_3$-3,4-OCH$_2$O— | 1.0 | 0.044 |
| 66 | CH=CH—C$_6$H$_3$-3,4-OC$_2$H$_4$O— | 1.1 | 0.12(0.038) |
| 67 | CH=CH-2-FURYL | 1.2 | 0.195 |
| 68 | CH=CH-3-PYRIDYL | 0.76%* | |
| 69 | CH=CH-4-ISOQUINOLYL | 1.75%* | |
| 70 | CH=CH-2-BENZOTHIENYL | 1.14%* | |
| 71 | CH=CH-4-BENZOTHIENYL | 1.8%* | |
| 72 | CH=CH-5-BENZOTHIENYL | 0.64%* | |
| 73 | CH=CH-4-BT-2-C(NH)NH$_2$ | 1.5 | 0.17 |
| 74 | CH=CH-5-BT-2-C(NH)NH$_2$ | 1.3%* | |
| 75 | C≡C-2-FURYL | 1.7 | 0.17 |
| 76 | C≡CC$_6$H$_5$ | 1.1% | |
| 77 | C≡C—C$_6$H$_3$-3,4-OCH$_2$O— | 2.3 | 0.059 |
| 78 | 5-PhFUR-2-YL | 8.4 | 0.49 |
| 79 | 5-[{3,4-OCH$_2$O}Ph]FUR-2-YL | 1.5% | |
| 80 | CH=CH—C$_6$H$_3$-4-NMe$_2$ | <0.6%* | |
| 81 | CH=CH—C$_6$H$_3$-3-OCH$_3$ | 0.22%* | |
| 82 | C≡C-5-INDANYL | 1.7%* | |
| 83 | CH=CH—C$_6$H$_3$-3,4-C$_2$H$_4$O— | | |
| 84 | 5-[{6-C[NH]NH$_2$}Naphth-2-yl]FUR-2-YL | | |

| | 5-SUBSTITUTED | uPA Direct | Upa Indirect |
|---|---|---|---|
| 1 | H | 25 (3.5%) | 4.9 |
| 101 | F | 12.7% | |
| 102 | Cl | 2.9% | |
| 103 | Br | 23.5 | 3.5 |
| 104 | I | 23 | 2.4 |
| 105 | CH$_3$ | 3.4% | |
| 106 | C$_2$H$_5$ | 3.6% | |
| 107 | n-C$_3$H$_7$ | 2.6% | |
| 108 | n-C$_4$H$_9$ | 3.4% | |
| 109 | CH$_2$CH(CH$_3$)C$_2$H$_5$ | 6.6% | |
| 110 | CH$_2$CH$_2$CH(CH$_3$)$_2$ | 4.2% | |
| 111 | n-C$_6$H$_{13}$ | 5.4%* | |
| 112 | CH$_2$CH$_2$-c-C$_3$H$_7$ | 3.3% | |
| 113 | CH$_2$CH$_2$OH | 2.9% | |
| 114 | CH=CH$_2$ | 11.4 | 1.6 |
| 115 | C(CH$_3$)=CH$_2$ | 1.2% | |
| 116 | CH=CHCH$_3$ | 1.6% | |
| 117 | CH=CHC$_2$H$_5$ | 1.1% | |
| 118 | CH=C(CH$_3$)C$_2$H$_5$ | 1.2% | |
| 119 | CH=CHCH(CH$_3$)$_2$ | 4.9% | |
| 120 | CH=CHC$_4$H$_9$ | 1.9%* | |
| 121 | CH=CH-c-C$_3$H$_5$ | 9.1 | 0.56 |
| 122 | CH=CHC$_6$H$_4$-p-C(NH)NH$_2$ | 2.3 | 0.98 |
| 123 | C≡CH | 2.5% | |
| 124 | C$_6$H$_5$ | 13.5 | 1.2 |
| 125 | 3-PYRIDYL | 3.6% | |
| 126 | 2-FURYL | 7.7 | 0.70 |
| 127 | 2-THIENYL | 1.1% | |
| 128 | 2-BENZOTHIENYL | | 0.94 |
| 129 | CF$_3$ | 8.2% | |
| 130 | CHO | 6.8% | |
| 131 | CH$_2$OH | 6.3% | |

| | 4,5-DISUBSTITUTED | uPA Direct | uPA Indirect |
|---|---|---|---|
| 201 | 4-SCH$_3$-5-CH=CH$_2$ | 4.4 | 0.67 |
| 202 | 4-Br-5-CH$_3$ | 3.0% | |
| 203 | 4-Cl-5-I | 3.5% | |
| 204 | 4-Br-5-OCH$_3$ | 15 | 1.7 |
| 205 | 4,5-BENZO | 0.27% | |
| 206 | 4,5b-THIEN-5-CH$_2$OH | 0.59%* | |
| 207 | 4,5b-THIEN-5-CH$_2$OCH$_3$ | 0.42%* | |
| 208 | 4,5b-THIEN-5-CH$_2$OAllyl | 1.9 | 0.30 |
| 209 | 4,5b-THIEN-5-C$_2$H$_2$Ph-p- | | 0.27 |

TABLE 3-continued

ACTIVITY OF THE 4- AND 5-SUBSTITUTED BENZOTHIOPHENE
AND THIENOTHIOPHENE UROKINASE INHIBITORS

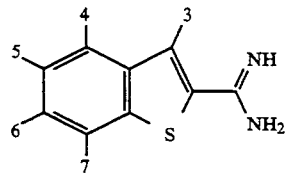

| | CNHNH2 | | |
|---|---|---|---|
| | OTHER PATTERNS | uPA Direct | uPA Indirect |
| 301 | 6-I | 13.7% | |
| 302 | 7-I | 10.8% | |
| 303 | 6-$CH_3$ | 12% | |
| 304 | 3-$CH_3$ | 75% | |
| 305 | 3-OH | >90% | |
| 306 | 3-$NH_2$ | 41% | |
| 307 | 7-C≡C—$C_6H_3$-3,4-$OCH_2$O— | 10.4%* | |
| 308 | 4-F-6-Br | 14.5% | |
| 309 | 4-$CH_3$O-7-Br | 18% | |
| 310 | 4-F-7-$CH_3$O | >90% | |
| 311 | 4-$CH_3$O-5,7-diBr | 18% | |
| 312 | 5,6-BENZO | 26 | 1.9 |
| 313 | 6,7-BENZO | 11% | |
| 314 | 2-H-5-C(NH)$NH_2$ | 43% | |
| 315 | 2-H-6-C(NH)$NH_2$ | 21% | |
| 316 | 2-H-3-C(NH)$NH_2$ | 80% | |
| 317 | 2-H-4-C(NH)$NH_2$ | 90% | |
| 318 | 7-AZA | 55% | |
| 319 | 2-GUANIDINObenzothiophene | >90% | |
| 320 | 2-Benzothienoylguanidine | 84% | |
| 321 | 2-Thieno[2,3-b]thienylC(NH)$NH_2$ | 4.1% | |
| 322 | 2-Thieno[4,5-b]thienylC(NH)$NH_2$ | 2.7% | |
| 323 | 2-Thieno[3,4-b]thienylC(NH)$NH_2$ | 5.3% | |

EXAMPLE 4

SELECTIVITY OF THE UROKINASE INHIBITORS

Using the assays described above, the selectivity for urokinase inhibition was determined for sample compounds according to the invention; Table 4 and FIG. 1 show these results. In Table 4, $IC_{50}$ values (in $\mu M$) were determined using the tPA Indirect Plasminogen-Linked Assay (supra), and results are given as simple numbers in column 5. In rare cases, the tPA Direct Assay gave a lower $IC_{50}$ value; for these compounds, the direct assay result is shown. Column 6 shows the $IC_{50}$ results (in $\mu M$) for plasmin as determined using the Plasmin Assay (supra). For both tPA and plasmin, percent values represent activities observed in the presence of 1 mM inhibitor, relative to inhibitor-free controls (columns 3 and 4). Because the ratios shown are with respect to the urokinase indirect plasminogen-linked assay using actual $IC_{50}$ values, larger ratios represent greater specificity for urokinase (relative to the protease being considered).

TABLE 4

| Ex# | SUBSTITUENT | tPA | PLASMIN | tPA/UPA | PLM/uPA |
|---|---|---|---|---|---|
| 1 | 4-H,5-H | 77% | 78% | >200 | >200 |
| 5 | 4-I | 86 | 352 | 261 | 1067 |
| 6 | 4-$CH_3$ | 478 | 881 | 810 | 1493 |
| 7 | 4-$C_2H_5$ | 184 | 427 | 263 | 610 |
| 9 | 4-n-$C_3H_7$ | 165 | 595 | 250 | 902 |
| 10 | 4-n-$C_4H_9$ | 148 | 381 | 352 | 907 |
| 12 | 4-$CH_2CH_2CH(CH_3)_2$ | 95 | 288 | 279 | 847 |
| 13 | 4-n-$C_6H_{13}$ | 90 | 195 | 214 | 464 |
| 17 | 4-CH=$CH_2$ | 8.6 | 57 | 6.3 | 42 |
| 20 | 4-$CH_2$CH=$CH_2$ | 57 | 505 | 127 | 1120 |
| 22 | 4-CH=CHCH($CH_3)_2$ | 43 | 244 | 391 | 2218 |
| 23 | 4-E-CH=CHCH($CH_3)_2$ | 41 | 629 | 315 | 4838 |
| 26 | 4-E-CH=CH$C_3H_7$ | 48 | 206 | 343 | 1471 |
| 27 | 4-CH=CH$C_4H_9$ | 85 | 244 | 250 | 718 |
| 39 | 4-C≡CH | 288 | 704 | 436 | 661 |
| 44 | 4-$C_6H_5$ | 64 | 881 | 58 | 800 |
| 48 | 4-(3-PYRIDYL) | 85 | 341 | 152 | 609 |
| 49 | 4-(2-FURANYL) | 19 | 360 | 53 | 1000 |
| 50 | 4-(2-THIENYL) | 28 | 381 | 56 | 762 |
| 51 | 4-(2-BENZOFURANYL) | 112 | 745 | 200 | 1330 |
| 53 | 5-[{4-C[NH]$NH_2$}Ph]FUR-2-YL | 4.1 | 47 | 45 | 511 |
| 56 | 4-$CH_2$OH | 563 | 67% | 640 | ≧1500 |
| 58 | 4-S$CH_3$ | 231 | 534 | 413 | 954 |
| 63 | 4-CH=CH$C_6H_5$ | 12 | 175 | 86 | 1250 |
| 65 | 4-CH=CH—$C_6H_3$-3,4-$OCH_2$O— | 25 | 630 | 568 | 14320 |

TABLE 4-continued

| Ex# | SUBSTITUENT | tPA | PLASMIN | tPA/UPA | PLM/uPA |
|---|---|---|---|---|---|
| 66 | 4-CH=CH—$C_6H_3$-3,4-$OC_2H_4O$— | 15 | 174 | 395 | 4580 |
| 67 | 4-CH=CH-2-FURYL | 26 | 195 | 133 | 1000 |
| 73 | 4-CH=CH-4-BT-2-C(NH)$NH_2$ | 2.7 | 25 | 15.9 | 147 |
| 75 | 4-C≡C-2-FURANYL | 33 | 288 | 194 | 1694 |
| 77 | 4-C≡C—$C_6H_3$-3,4-$OCH_2O$— | 8.4 | ≈250 | 142 | ≈4240 |
| 78 | 4-(5-Ph-FURAN-2-YL) | 26 | ≈250 | 53 | ≈500 |
| 103 | 5-Br | 63% | 98% | ≧400 | ≧4000 |
| 104 | 5-I | 63% | 96% | ≧500 | ≧5000 |
| 114 | 5-CH=$CH_2$ | 37 | 288 | 23 | 180 |
| 121 | 5-CH=CH-c-$C_3H_5$ | 175 | 1050 | 313 | 1875 |
| 122 | 5-CH=CH—$C_6H_4$-p-C=$NHNH_2$ | 1.45 | 360 | 1.48 | 367 |
| 124 | 5-$C_6H_5$ | 258 | 90% | 215 | ≧10000 |
| 126 | 5-(2-FURANYL) | 140 | 534 | 200 | 763 |
| 201 | 4-$SCH_3$-5-CH=$CH_2$ | 20 | 43 | 30 | 65 |
| 204 | 4-Br-5-$OCH_3$ | 427 | 69% | 251 | ≧750 |
| 208 | 4,5b-THIEN-5-$CH_2$OAllyl | 57 | 273 | 190 | 910 |
| 312 | 5,6-BENZO | >>100 | >>100 | >>50 | >>50 |
| 321 | 2-Thieno[2,3-b]thienylC(NH)NH2 | 74% | 88% | ≧500 | ≧1000 |

EXAMPLE 5
REVERSIBLE COMPETITIVE INHIBITION BY UROKINASE INHIBITORS

Figure 2:
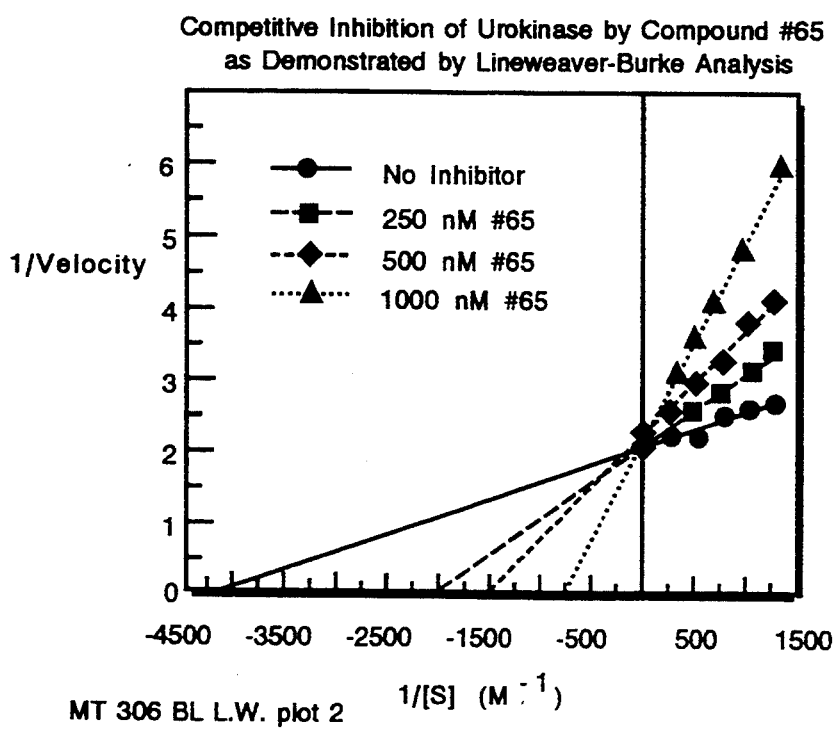
FIG. 2 shows competitive inhibition of urokinase by a compound of the invention.

The compounds according to the invention exhibit competitive, reversible inhibition of urokinase. This is illustrated in FIG. 2 by a Lineweaver-Burke analysis of the unusually potent compound, Compound #65. Note the common positive y-intercept point of all lines, a characteristic of competitive, reversible inhibitors.

EXAMPLE 6
INHIBITION OF CELL-ASSOCIATED UROKINASE

Figure 3:
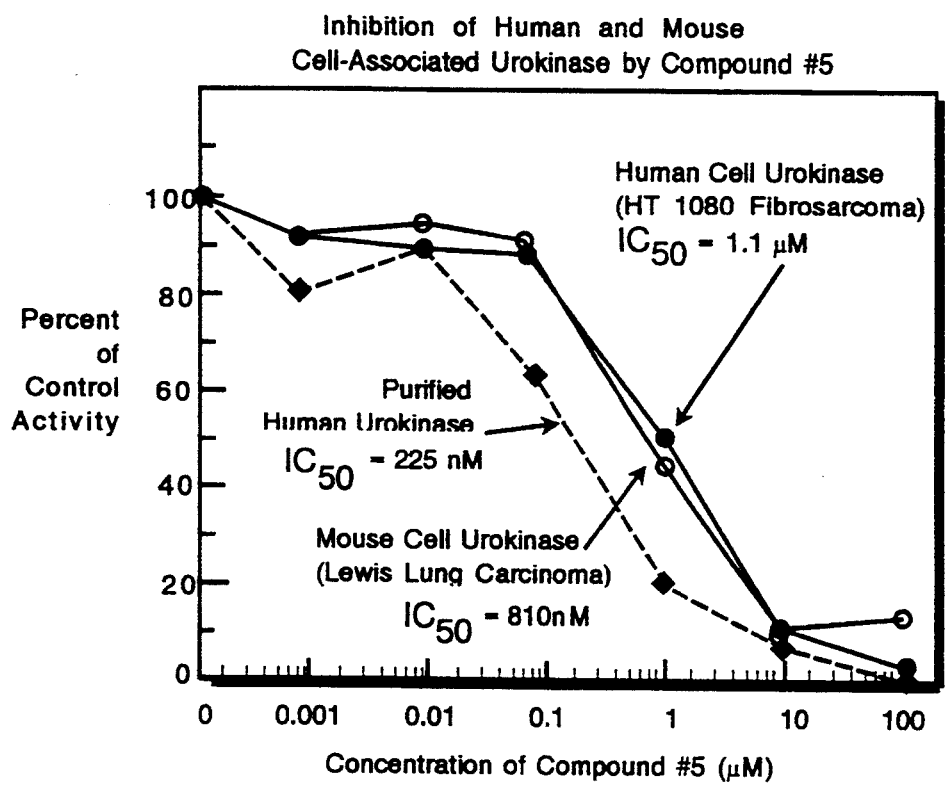
FIG. 3 shows inhibition of human and mouse cell-associated urokinase by a compound of the invention.

Since it is cell surface, receptor-bound urokinase, and not free urokinase, which mediates most if not all cellular invasive events, compounds according to the invention were tested for their ability to inhibit urokinase in this form. As demonstrated in the plasminogen-linked Cell Surface Urokinase Inhibition Assay (supra) in which whole living HT1080 human fibrosarcoma or mouse Lewis lung carcinoma cells are used as a urokinase source, compound #5 is a highly effective inhibitor of cell surface, receptor-bound urokinase in both the human and mouse system, although there is some loss of potency relative to the purified enzyme (FIG. 3).

EXAMPLE 7
INHIBITION OF UROKINASE-MEDIATED FIBRONECTIN DEGRADATION

Figure 4:
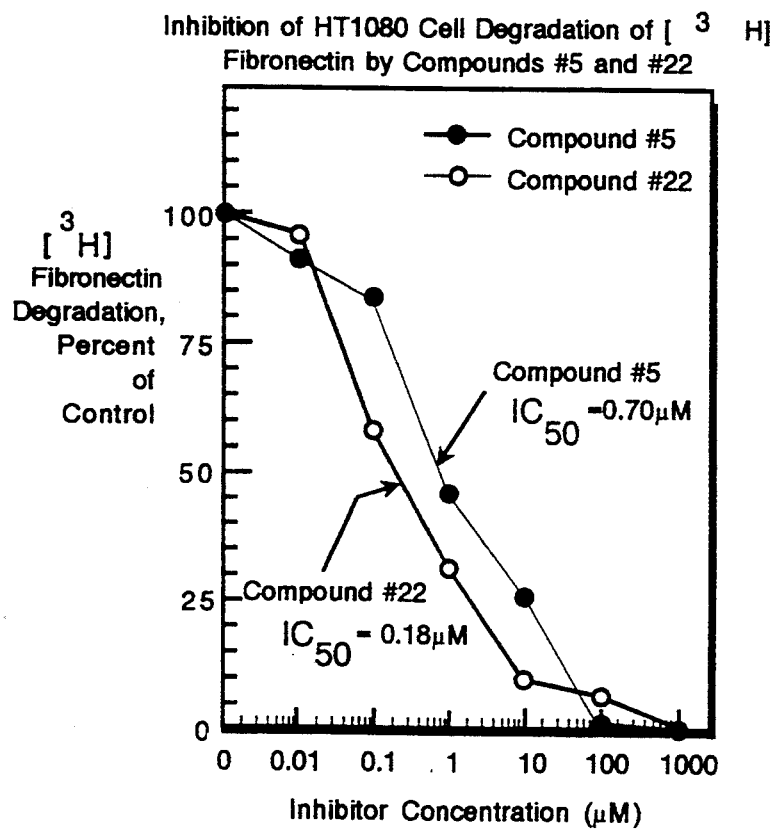
FIG. 4 shows inhibition of urokinase-mediated cellular degradation of fibronectin by compounds of the invention.

To test whether the compounds of the invention were capable of demonstrably inhibiting urokinase-mediated cellular functions, they were assayed using the Cell Based [$^3$H]Fibronectin Degradation Assay (supra). As shown in FIG. 4, compounds #5 and #22 were effective inhibitors of cellular degradation of [$^3$H]fibronectin. Degradation in this system is dependent on the presence of plasminogen (i.e., plasminogen activator-dependent [$^3$H]fibronectin degradation), and all inhibitory activity is blocked by anti-urokinase antibodies (but not by antitPA antibodies), demonstrating that the observed inhibition is in fact due to inhibition of urokinase, and not inhibition of tPA or plasmin.

EXAMPLE 8
INHIBITORY ACTIVITY AGAINST OTHER SERINE PROTEASES

There are a large number of serine proteases with active sites similar to the catalytic triad of urokinase. To determine whether compounds according to the invention similarly inhibited these proteases, Compound 5 was chosen as a sample compound and assayed using the Chymotrypsin Assay, the Elastase Assay, the Kallikrein Assay, the Thrombin Assay, and the Trypsin Assay (supra). These results are shown in Table 5.

TABLE 5

| Compound # | Chymotrypsin | Elastase | Kallikrein | Thrombin | Trypsin |
|---|---|---|---|---|---|
| 5 | >1 mM | >1 mM | 8.4 µM | 741 µM | 2.8 µM |

EXAMPLE 9
INHIBITORY EFFECT OF COMPOUND 5 ON LL/2-M1 SUBCUTANEOUS TUMOR GROWTH IN C57BL/6 MICE

Two groups of 20 C57BL/6 mice were tested at approximately 8 weeks of age. Oral dosing (0.5 mg/ml compound 5 in drinking water; plain water for controls) began 5 days before subcutaneous (s.c.) injection of $1 \times 10^6$ LL/2-M1 cells (subline of LL/2 Lewis lung carcinoma cells generated by applicants). One day prior to cell injection, intraperitoneal (i.p.) dosing was superimposed on oral dosing, and consisted of single daily i.p. injections at 30 mg/kg Compound 5 in 200 ml 5% glucose, or 200 ml 5% glucose for controls. Injections were performed daily Monday-Friday only. By day 13, 100% of control mice and 95% of experimental mice had developed measurable s.c. tumors.

Length and width measurements of the tumors were taken twice weekly with calipers. Measurements were averaged to preclude orientational bias, generating an idealized tumor diameter. Half of this value was taken as an idealized radius, and the volume of a semi-sphere having this radius was calculated. A wet weight of 1 g/ml was assumed. Calculations of tumor wet weight in living animals is based on literature procedures.

To minimize discomfort to mice and to prevent spontaneous death due to tumor burden, 4 criteria were used to determine if and when an animal should be euthanized: (i) ulcerated tumors; (ii) tumors judged likely to ulcerate during the next 24 hours; (iii) tumors in excess of 10% of body weight; and (iv) lethargy or obvious discomfort. Thus, "survival" in this experiment should be viewed as lack of euthanasia based on the above criteria.

Following euthanasia, lungs were removed and stained with India ink using the procedures of Wexler (Wexler, H. *J. Natl. Can. Inst.* 36:641–645, 1966). Metastases (i.e., "Mets") were then scored manually using a dissecting microscope.

Figure 5:
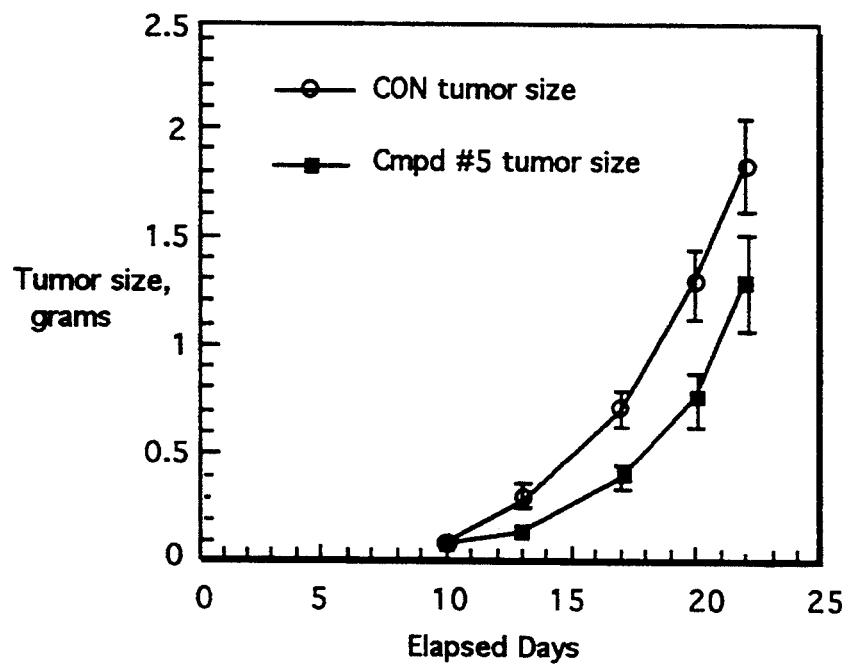
FIG. 5 shows the inhibitory effect of a compound of the invention on primary tumor growth in mice.
Figure 6:
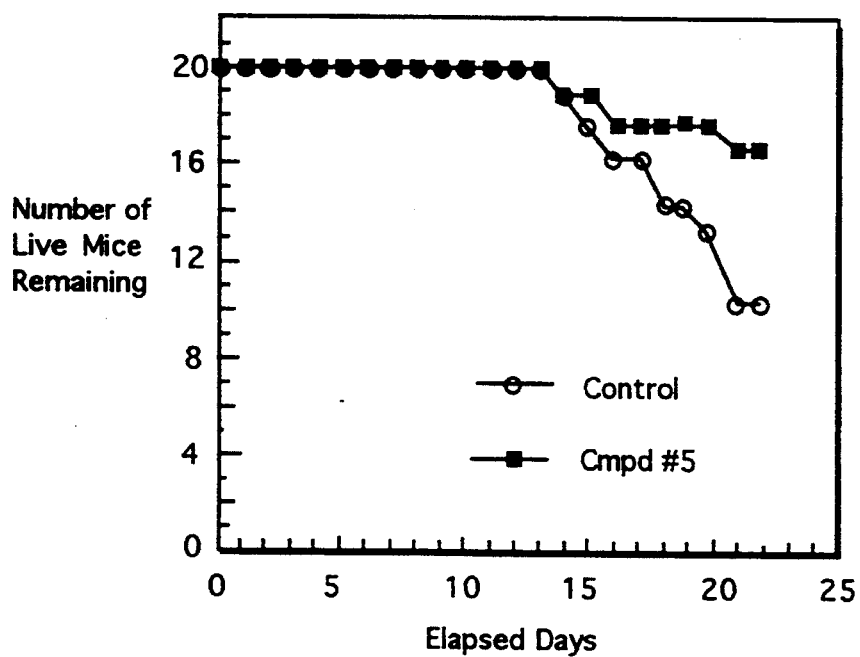
FIG. 6 shows the protective effect of a compound of the invention on the survival of tumor-bearing mice.

Data from the above experiments are shown in FIGS. 5 and 6 and in Table 6. As shown in FIG. 5, Compound 5 inhibited subcutaneous LL/2-M1 tumor growth in C57BL/6 mice. As shown in FIG. 6, Compound 5 increased survival time in tumor bearing mice. Differences in lung metastasis number in these mice were not statistically significant (Table 6; SE: Standard Error; Range: Difference between the highest and the lowest number of mets/mouse; N: Number of Mice Tested). The slight increase in the Compound 5 group relative to control probably reflected the fact that proportionately more control animals bearing the largest tumors had been euthanized by day 21. These control animals would probably would have had higher numbers of lung metastases had they survived to day 21.

TABLE 6

| Group | Mean lung mets/mouse | SE | Range | N |
|---|---|---|---|---|
| Control | 13.4 | 2.5 | 3–28 | 11 |
| Compound 5 | 17.5 | 2.3 | 1–37 | 15 |

THERAPY

The compounds described herein provide useful therapeutics for the treatment or prevention of any urokinase-mediated disorder. Such disorders include, without limitation, infiltration of immune cells into inflammatory sites, fibrosis, local invasion of tumors into adjacent areas, metastatic spread of tumor cells from primary to secondary sites, and tissue destruction in arthritis. Because urokinase is also involved in embryo implantation in the uterus, ovulation, and migration of sperm during spermatogenesis, the urokinase inhibitors described herein may also be formulated as effective contraceptives.

The urokinase inhibitor is typically administered in a physiologically-acceptable carrier, e.g., dissolved in physiological saline. Administration is by any appropriate route, but ordinarily it will be administered intravenously (e.g., by intravenous injection or transfusion) or, preferably, orally. When used for cancer treatment, the urokinase inhibitor may beused by itself, or administered prior to or following surgery and/or as a co-therapy with radiation, chemotherapy or immunological treatment. Urokinase inhibitors are administered in dosages which provide suitable inhibition for urokinase-mediated cellular invasiveness, but which minimize any residual inhibition of tPA or plasmin. Generally, these dosages are between 0.01–100 mg/kg/day.

What is claimed is:

1. A compound of the formula:

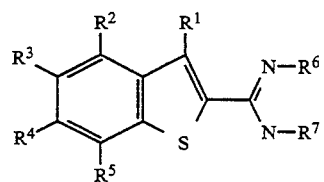

wherein
a) $R^1$ is H, $NH_2$, or a halogen;
b)
  i: each $R^2$–$R^5$, independently, is a H; a halogen; a hydroxy; a nitro;
  a straight chain alkyl group of between 5 and 10 carbons;
  a straight chain alkenyl of between 1 and 10 carbons;
  a straight chain alkynyl of between 1 and 10 carbons;
  an alkyl of between 1 and 10 carbons, wherein said alkyl is substituted with an $R^8$ group, and wherein, when said alkyl is of less than 5 carbons, $R^8$ is not a halogen;
  an alkoxy of between 1 and 10 carbons, wherein said alkoxy is substituted with an $R^8$ group, and wherein, when said alkoxy is of less than 5 carbons, $R^8$ is not a halogen;
  a straight chain alkenyl group of between 2 and 10 carbons with an E or Z double bond substituted with at least one $R^8$ group;
  a straight chain alkynyl group of between 2 and 10 carbons substituted with at least one $R^8$ group;
  a cycloalkyl group of between 3 and 10 carbons;
  a cycloalkenyl group of between 3 and 10 carbons;
  a bicycloalkyl group of between 6 and 12 carbons;
  a bicycloalkenyl group of between 7 and 12 carbons;
  a cycloalkyl-alkyl group of between 4 and 20 carbons;
  a cycloalkyl-alkenyl group of between 5 and 20 carbons;
  a cycloalkyl-alkynyl group of between 5 and 20 carbons;
  a cycloalkenyl-alkyl group of between 4 and 20 carbons;
  a cycloalkenyl-alkenyl group of between 5 and 20 carbons;
  a cycloalkenyl-alkynyl group of between 5 and 20 carbons;
  a thio/sulfinyl/sulfonylalkyl group of between 1 and 10 carbons;
  a thio/sulfinyl/sulfonylalkyl group of between 1 and 10 carbons substituted with at least one $R^8$ group;
  a thio/sulfinyl/sulfonylalkenyl group of between 1 and 10 carbons;
  a thio/sulfinyl/sulfonylalkenyl group of between 1 and 10 carbons substituted with at least one $R^8$ group;
  a thio/sulfinyl/sulfonylcycloalkyl group of between 3 and 6 carbons;
  a thio/sulfinyl/sulfonylcycloalkenyl group of between 3 and 6 carbons;
  a phenyl group;

a phenyl group substituted with at least one $R^9$ group;

a 2- or 3-furanyl group; a 2- or 3-thienyl group; a 2- or 3- or 4-pyridyl group; a pyrimidyl group; an oxazolo group; an isoxazolo group; a thiazolo group; an isothiazolo group; a pyrazolo group; an imidazolo group; a pyrazino group; a pyridazino group;

a bicyclic aromatic group chosen from a naphthyl group, a benzothienyl group, an indolyl group, a benzofuranyl group, a naphthyridinyl group, a quinoxalinyl group, a quinazolinyl group, a quinolinyl group, an isoquinolinyl group, a benzimidazoyl group, a benzoxazoyl group, or a benzothiozoyl group, or any of said bicyclic aromatic groups substituted with at least one $R^9$ group;

a biaryl group consisting of two aromatic groups, the same or different, linked directly together or at least one of the aromatic groups substituted with at least one $R^9$ group;

a tetrahydrofuranyl group;

a cycloalkoxy group of between 3 and 8 carbons;

a cycloalkenoxy group of between 3 and 8 carbons;

an oxy(heteroaryl)aryl group; an oxy(heteroaryl)aryl group substituted with at least one $R^9$ group;

a thio/sulfinyl/sulfonyl(heteroaryl)aryl group; a thio/sulfinyl/sulfonyl(heteroaryl)aryl group substituted with at least one $R^9$ group;

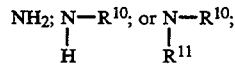

ii: $R^2$ and $R^3$, taken together, form an aryl ring chosen from a phenyl group, a 2- or 3-furanyl group, a 2- or 3-thienyl group, a 2- or 3- or 4-pyridyl group, a pyrimidyl group, an oxazolo group, an isoxazolo group, a thiazolo group, an isothiazolo group, a pyrazolo group, an imidazolo group, a pyrazino group, a pyridazino group, or any of said aryl ring groups substituted with at least one $R^9$ group or with at least one $R^{12}$ group; or iii: $R^4$, taken with $R^3$ or $R^5$, forms an aryl ring chosen from a phenyl group, a 2- or 3-furanyl group, a 2- or 3-thienyl group, a 2- or 3- or 4-pyridyl group, a pyrimidyl group, an oxazolo group, an isoxazolo group, a thiazolo group, an isothiazolo group, a pyrazolo group, an imidazolo group, a pyrazino group, a pyridazino group, or any of said aryl ring groups substituted with at least one $R^9$ group or with at least one $R^{12}$ group;

c) wherein each $R^8$, independently, is:
a straight chain alkyl group of between 1 and 6 carbons;
a cycloalkyl ring of between 3 and 6 carbons;
an alkoxy group of between 1 and 6 carbons;
an alkylthio group of between 1 and 6 carbons; an alkylthio group of between 1 and 6 carbons with the S oxidized;
a hydroxy group; a halogen group; a phenyl group;
a phenyl group substituted with at least one $R^9$ group;
a 2- or 3-furanyl group; a 2- or 3-thienyl group; a 2- or 3- or 4-pyridyl group; a pyrimidyl group; an oxazolo group; an isoxazolo group; a thiazolo group; an isothiazolo group; a pyrazolo group; an imidazolo group; a pyrazino group; a pyridazino group;

a bicyclic aromatic group chosen from a naphthyl group, a benzothienyl group, an indolyl group, a benzofuranyl group, a naphthyridinyl group, a quinoxalinyl group, a quinazolinyl group, a quinolinyl group, an isoquinolinyl group, a benzimidazoyl group, a benzoxazoyl group, or a benzothiazoyl group, or any of said bicyclic aromatic groups substituted with at least one $R^9$ group;

tetrahydrofuranyl; or tetrahydrothiofuranyl;

d) wherein each $R^9$, independently, is:
a straight chain alkyl group of between 1 and 6 carbons; an alkoxy group of between 1 and 6 carbons; an acyloxy group of between 1 and 6 carbons; a methylenedioxy group; an ethylenedioxy group; a hydroxymethyl group; an alkoxymethyl group of between 1 and 6 carbons; a halo group; a hydroxy group; a nitro group; a cyano group; an acyl group of between 1 and 6 carbons; an alkylthio group of between 1 and 6 carbons; an alkylthio group of between 1 and 6 carbons with an oxidized S; a carboxylic acid group; a carboxylate ester group; or a carboxamidino group, a carboxamido group, or an amino group, wherein the nitrogen group is

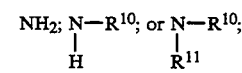

e)
i: wherein each $R^{10}$ and $R^{11}$ is:
a straight chain alkyl group of between 3 and 6 carbons; a cycloalkyl group of between 3 and 6 carbons; a phenyl group; or a phenyl group substituted with at least one $R^9$ group; or ii: wherein $R^{10}$ and $R^{11}$, taken together, form a pyrrolidinyl, a piperidinyl, a morpholino, or an N-substituted piperazino ring; and f) wherein each $R^{12}$, independently, is:
an alkenoxymethyl group of between 1 and 6 carbons;
an alkynoxymethyl group of between 1 and 6 carbons;
an arylalkenyl group;
an arylalkenyl group, wherein said aryl is phenyl, 2- or 3-furanyl, 2- or 3-thienyl, 2- or 3- or 4-pyridyl, pyrimidyl, oxazolo, isoxazolo, thiazolo, isothiazolo, pyrazolo, imidazolo, pyrazino, or pyradazino, or any of said aryl groups substituted with at least one $R^9$ group;
an arylalkynyl group; or
an arylalkynyl group, wherein said aryl is phenyl, 2- or 3-furanyl, 2- or 3-thienyl, 2- or 3- or 4-pyridyl, pyrimidyl, oxazolo, isoxazolo, thiazolo, isothiazolo, pyrazolo, imidazolo, pyrazino, or pyradazino, or any of said aryl groups substituted with at least one $R^9$ group;, provided that at least one $R^2$–$R^5$ contains a sulfur atom, an unsaturated carbon group, or a cyclic group; and each $R^6$ and $R^7$, independently, is H or a straight chain alkyl group of between 1 and 6 carbons.

2. The compound of claim 1, wherein $R^1$ is H.

3. The compound of claim 1, wherein $R^1$ is $NH_2$.

4. The compound of claim 1, wherein $R^2$ contains less than or equal to 40 carbon atoms.

5. The compound of claim 1, wherein $R^2$ is planar.

6. The compound of claim 1, wherein $R^2$ is a saturated alkyl chain or is an unsaturated alkyl chain having one of its double or triple bonds located at the 1 position.

7. The compound of claim 6, having an E double bond at the 1 position.

8. The compound of claim 6, wherein said carbon chain terminates in an aromatic ring group.

9. The compound of claim 1, wherein $R^2$ is an aromatic or biaryl compound.

10. The compound of claim 1, wherein $R^3$, $R^4$, or $R^5$ contains less than or equal to 20 carbon atoms.

11. The compound of claim 1, wherein each of $R^4$–$R^7$ is H.

12. The compound of claim 1, formulated as a hydrochloride salt.

13. A therapeutic composition essentially comprising a compound according to claim 1, said compound being formulated in a physiologically-acceptable carrier.

14. A method for treating urokinase-mediated cellular invasion in a mammal, comprising administering to said mammal a urokinase-inhibiting amount of a compound of formula:

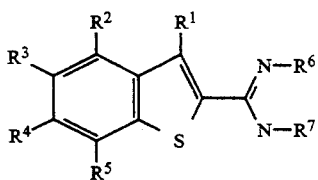

wherein a) $R^1$ is H, $NH_2$, or a halogen;

b)
  i: each $R^2$–$R^5$, independently, is a H; a halogen; a hydroxy; a nitro; an alkyl group of between 5 and 10 carbons, an alkenyl of between 1 and 10 carbons; an alkynyl of between 1 and 10 carbons;

an alkyl of between 1 and 10 carbons, wherein said alkyl is substituted with an $R^8$ group, and wherein, when said alkyl is of less than 5 carbons, $R^8$ is not a halogen;

an alkoxy of 1–10 carbons inclusive, wherein said alkoxy is substituted with an $R^8$ group, and wherein, when said alkoxy is of less than 5 carbons, $R^8$ is not a halogen;

a straight chain alkenyl group of between 2 and 10 carbons with an E or Z double bond substituted with at least one $R^8$ group;

a straight chain alkynyl group of between 2 and 10 carbons substituted with at least one $R^8$ group;

a cycloalkyl group of between 3 and 10 carbons;

a cycloalkenyl group of between 3 and 10 carbons;

a bicycloalkyl group of between 6 and 12 carbons;

a bicycloalkenyl group of between 7 and 12 carbons;

a cycloalkyl-alkyl group of between 4 and 20 carbons;

a cycloalkyl-alkenyl group of between 5 and 20 carbons;

a cycloalkyl-alkynyl group of between 5 and 20 carbons;

a cycloalkenyl-alkyl group of between 4 and 20 carbons;

a cycloalkenyl-alkenyl group of between 5 and 20 carbons;

a cycloalkenyl-alkynyl group of between 5 and 20 carbons;

a thio/sulfinyl/sulfonylalkyl group of between 1 and 10 carbons;

a thio/sulfinyl/sulfonylalkyl group of between 1 and 10 carbons substituted with at least one $R^8$ group;

a thio/sulfinyl/sulfonylalkenyl group of between 1 and 10 carbons;

a thio/sulfinyl/sulfonylalkenyl group of between 1 and 10 carbons substituted with at least one $R^8$ group;

a thio/sulfinyl/sulfonylcycloalkyl group of between 3 and 6 carbons;

a thio/sulfinyl/sulfonylcycloakenyl group of between 3 and 6 carbons;

a phenyl group;

a phenyl group substituted with at least one $R^9$ group;

a 2- or 3-furanyl group; a 2- or 3-thienyl group; a 2- or 3- or 4-pyridyl group; a pyrimidyl group; an oxazolo group; an isoxazolo group; a thiazolo group; an isothiazolo group; a pyrazolo group; an imidazolo group; a pyrazino group; a pyridazino group;

a bicyclic aromatic group chosen from a naphthyl group, a benzothienyl group, an indolyl group, a benzofuranyl group, a naphthyridinyl group, a quinoxalinyl group, a quinazolinyl group, a quinolinyl group, an isoquinolinyl group, a benzimidazoyl group, a benzoxazoyl group, or a benzothiozoyl group, or any of said bicyclic aromatic groups substituted with at least one $R^9$ group;

a biaryl group consisting of two aromatic groups, the same or different, linked directly together or at least one of the aromatic groups substituted with at least one $R^9$ group;

a tetrahydrofuranyl group;

a cycloalkoxy group of between 3 and 8 carbons;

a cycloalkenoxy group of between 3 and 8 carbons;

an oxy(heteroaryl)aryl group; an oxy(heteroaryl)aryl group substituted with at least one $R^9$ group;

a thio/sulfinyl/sulfonyl(heteroaryl)aryl group; a thio/sulfinyl/sulfonyl(heteroaryl)aryl group substituted with at least one $R^9$ group;

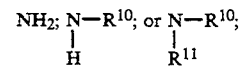

ii: $R^2$ and $R^3$, taken together, form an aryl ring chosen from a phenyl group, a 2- or 3-furanyl group, a 2- or 3-thienyl group, a 2- or 3- or 4-pyridyl group, a pyrimidyl group, an oxazolo group, an isoxazolo group, a thiazolo group, an isothiazolo group, a pyrazolo group, an imidazolo group, a pyrazino group, a pyridazino group, or any of said aryl ring groups substituted with at least one $R^9$ group or with at least one $R^{12}$ group; or iii: $R^4$, taken with $R^3$ or $R^5$, forms an aryl ring chosen from a phenyl group, a 2- or 3-furanyl group, a 2- or 3-thienyl group, a 2- or 3- or 4- pyridyl group, a pyrimidyl group, an oxazolo group, an isoxazolo group, a thiazolo group, an isothiazolo group, a pyrazolo group, an imidazolo group, a pyrazino group, a pyridazino group, or any of said aryl ring groups substituted with at least one $R^9$ group or with at least one $R^{12}$ group; and c) wherein each $R^8$, independently, is:
a straight chain alkyl group of between 1 and 6 carbons;
a cycloalkyl ring of between 3 and 6 carbons;
an alkoxy group of between 1 and 6 carbons;
an alkylthio group of between 1 and 6 carbons; an alkylthio group of between 1 and 6 carbons with the S oxidized;
a hydroxy group; a halogen group; a phenyl group; a phenyl group substituted with at least one $R^9$ group;
a 2- or 3-furanyl group; a 2- or 3-thienyl group; a 2- or 3- or 4-pyridyl group; a pyrimidyl group; an oxazolo group; an isoxazolo group; a thiazolo group; an isothiazolo group; a pyrazolo group; an imidazolo group; a pyrazino group; a pyridazino group;
a bicyclic aromatic group chosen from a naphthyl group, a benzothienyl group, an indolyl group, a benzofuranyl group, a naphthyridinyl group, a quinoxalinyl group, a quinazolinyl group, a quinolinyl group, an isoquinolinyl group, a benzimidazoyl group, a benzoxazoyl group, or a benzothiazoyl group, or any of said bicyclic aromatic groups substituted with at least one $R^9$ group;
tetrahydrofuranyl; or tetrahydrothiofuranyl;

d) wherein each $R^9$, independently, is:
a straight chain alkyl group of between 1 and 6 carbons; an alkoxy group of between 1 and 6 carbons; an acyloxy group of between 1 and 6 carbons; a methylenedioxy group; an ethylenedioxy group; a hydroxymethyl group; an alkoxymethyl group of between 1 and 6 carbons; a halo group; a hydroxy group; a nitro group; a cyano group; an acyl group of between 1 and 6 carbons; an alkylthio group of between 1 and 6 carbons; an alkylthio group of between 1 and 6 carbons with an oxidized S; a carboxylic acid group; a carboxylate ester group; or a carboxamidino group, a carboxamido group, or an amino group, wherein the nitrogen group is

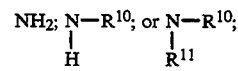

e)
i: wherein each $R^{10}$ and $R^{11}$ is:
a straight chain alkyl group of between 1 and 6 carbons; a cycloalkyl group of between 3 and 6 carbons; a phenyl group; or a phenyl group substituted with at least one $R^9$ group; or
ii: wherein $R^{10}$ and $R^{11}$, taken together, form a pyrrolidinyl, a piperidinyl, a morpholino, or an N-substituted piperazino ring; and f) wherein each $R^{12}$, independently, is:
an alkenoxymethyl group of between 1 and 6 carbons;
an alkynoxymethyl group of between 1 and 6 carbons;
an arylalkenyl group;
an arylalkenyl group, wherein said aryl is phenyl, 2- or 3-furanyl, 2- or 3-thienyl, 2- or 3- or 4-pyridyl, pyrimidyl, oxazolo, isoxazolo, thiazolo, isothiazolo, pyrazolo, imidazolo, pyrazino, or pyradazino, or any of said aryl groups substituted with at least one $R^9$ group;
an arylalkynyl group; or
an arylalkynyl group, wherein said aryl is phenyl, 2- or 3-furanyl, 2- or 3-thienyl, 2- or 3- or 4-pyridyl, pyrimidyl, oxazolo, isoxazolo, thiazolo, isothiazolo, pyrazolo, imidazolo, pyrazino, or pyradazino, or any of said aryl groups substituted with at least one $R^9$ group;
each $R^6$ and $R^7$, independently, is H or a straight chain alkyl group of between 1 and 6 carbons.

15. The method of claim 14, wherein at least one $R^2$–$R^5$ contains 5 carbons or greater, a sulfur atom or hydroxy, an unsaturated carbon group, or a cyclic group.

* * * * *

UNITED STATES PATENT AND TRADEMARK OFFICE
CERTIFICATE OF CORRECTION

PATENT NO. : 5,340,833
DATED : August 23, 1994
INVENTOR(S) : Alexander Bridges, et. al.

It is certified that error appears in the above-indentified patent and that said Letters Patent is hereby corrected as shown below:

Col. 1, line 27, replace "Anderson" with --Andreasen--;

Col. 5, line 11, delete "one" (second occurrence);

Col. 9, line 34, after "are", insert --each H groups;--;

Col. 17, line 61, delete "the" (second occurrence);

Col. 18, line 52, replace "7.31", with --7.38--;

Col. 19, line 52, replace "celite" with --Celite--;

Col. 20, line 4, replace "iltration" with --filtration--;

Col. 26, line 31, replace "1H,d,J=7.6 Hz" with --1H,t,J=7.6 Hz--;

Col. 27, line 58, replace "TFBA" with --TBAF--;

Col. 28, line 7, replace "disslolved" with --dissolved--;

Col. 30, line 49, replace "transfered" with --transferred--;

Col. 41, line 18, replace "3.25" with --32.5--;

UNITED STATES PATENT AND TRADEMARK OFFICE
CERTIFICATE OF CORRECTION

PATENT NO. : 5,340,833
DATED : August 23, 1994
INVENTOR(S) : Alexander Bridges, et. al.

It is certified that error appears in the above-indentified patent and that said Letters Patent is hereby corrected as shown below:

Col. 44, line 12, replace "aqueousd" with --aqueous--;

Col. 70, line 8, after "7.89", insert the following: --(4H, sl br s), 7.84--;

Col. 74, line 7, replace "rigourously" with --rigorously--;

Col. 75, line 67, replace "snd" with --and--;

Col. 77, line 51, replace "recrystalised" with --recrystallized--;

Col. 78, line 31, replace "rigourously" with --rigorously--;

Col. 79, line 45, replace "rigourously" with --rigorously--;

Col. 82, line 39, replace "qas" with --was--;

Col. 93, line 58, replace "beused" with --be used--;

UNITED STATES PATENT AND TRADEMARK OFFICE
CERTIFICATE OF CORRECTION

PATENT NO. : 5,340,833
DATED : August 23, 1994
INVENTOR(S) : Alexander Bridges, et. al.

It is certified that error appears in the above-indentified patent and that said Letters Patent is hereby corrected as shown below:

Col. 96, line 37, claim 1, replace "alkyl group of between 3 and 6" with -- alkyl group of between 1 and 6--.

Signed and Sealed this

Thirteenth Day of December, 1994

Attest:

BRUCE LEHMAN

*Attesting Officer*     *Commissioner of Patents and Trademarks*